United States Patent
Daigle et al.

(10) Patent No.: US 9,968,885 B2
(45) Date of Patent: May 15, 2018

(54) **TECHNIQUES FOR CO₂ CAPTURE USING *SULFURIHYDROGENIBIUM* SP. CARBONIC ANHYDRASE**

(71) Applicant: CO2 SOLUTIONS INC., Québec (CA)

(72) Inventors: Richard Daigle, Lévis (CA); Éric Madore, Québec (CA); Sylvie Fradette, Lévis (CA)

(73) Assignee: CO2 Solutions Inc., Quebec (CA)

( * ) Notice: Subject to any disclaimer, the term of this patent is extended or adjusted under 35 U.S.C. 154(b) by 135 days.

(21) Appl. No.: 14/439,218

(22) PCT Filed: Oct. 29, 2013

(86) PCT No.: PCT/CA2013/050818
§ 371 (c)(1),
(2) Date: Apr. 28, 2015

(87) PCT Pub. No.: WO2014/066999
PCT Pub. Date: May 8, 2014

(65) Prior Publication Data
US 2015/0283502 A1    Oct. 8, 2015

Related U.S. Application Data

(60) Provisional application No. 61/719,710, filed on Oct. 29, 2012.

(51) Int. Cl.
*C12N 9/88* (2006.01)
*B01D 53/84* (2006.01)
(Continued)

(52) U.S. Cl.
CPC ........ *B01D 53/84* (2013.01); *B01D 53/1475* (2013.01); *B01D 53/1493* (2013.01);
(Continued)

(58) Field of Classification Search
None
See application file for complete search history.

(56) References Cited

U.S. PATENT DOCUMENTS 6,908,507 B2   6/2005   LaLande et al.
6,946,288 B2   9/2005   Blais et al.
(Continued)

FOREIGN PATENT DOCUMENTS

CA   2291785   10/1998
CA   2329113   6/2002
(Continued)

OTHER PUBLICATIONS

GenBank Accession No. ACD66216.1, published May 21, 2008.*
(Continued)

*Primary Examiner* — Richard C Ekstrom
(74) *Attorney, Agent, or Firm* — Knobbe, Martens, Olson & Bear, LLP

(57) ABSTRACT

Use of *Sulfurihydrogenibium* sp. carbonic anhydrase (SspCA) or mutants thereof for catalyzing the hydration reaction of $CO_2$ into bicarbonate and hydrogen ions or catalyzing the desorption reaction to produce a $CO_2$ gas is provided.

20 Claims, 12 Drawing Sheets

(51) Int. Cl.
  *B01D 53/14* (2006.01)
  *C12M 1/40* (2006.01)
  *C12M 1/00* (2006.01)
(52) U.S. Cl.
  CPC ............ *C12M 21/18* (2013.01); *C12M 29/20* (2013.01); *C12N 9/88* (2013.01); *B01D 2252/20494* (2013.01); *B01D 2252/602* (2013.01); *B01D 2255/804* (2013.01); *C12Y 402/01001* (2013.01); *Y02C 10/04* (2013.01); *Y02C 10/06* (2013.01); *Y02P 20/59* (2015.11)

(56) References Cited

U.S. PATENT DOCUMENTS

| | | | |
|---|---|---|---|
| 7,514,056 | B2 | 4/2009 | Fradette et al. |
| 7,521,217 | B2 | 4/2009 | Daigle et al. |
| 7,596,952 | B2 | 10/2009 | Fradette et al. |
| 7,740,689 | B2 | 6/2010 | Fradette et al. |
| 8,066,965 | B2 | 11/2011 | Fradette et al. |
| 8,263,383 | B2 | 9/2012 | Daigle et al. |
| 8,277,769 | B2 | 10/2012 | Fradette et al. |
| 8,722,391 | B2 | 5/2014 | Fradette et al. |
| 8,846,377 | B2 | 9/2014 | Fradette et al. |
| 2007/0048856 | A1 | 3/2007 | Parent et al. |
| 2011/0097781 | A1 | 4/2011 | Parent et al. |
| 2012/0122195 | A1 | 5/2012 | Fradette et al. |
| 2012/0129236 | A1 | 5/2012 | Fradette et al. |
| 2013/0052720 | A1 | 2/2013 | Fradette et al. |
| 2013/0203155 | A1 | 8/2013 | Penders et al. |

FOREIGN PATENT DOCUMENTS

| | | |
|---|---|---|
| CA | 2443222 | 10/2002 |
| CA | 2393016 | 1/2003 |
| CA | 2554395 | 1/2007 |
| CA | 2738061 | 2/2011 |
| CA | 2769771 | 2/2011 |
| CA | 2714304 | 1/2013 |
| EP | 1377531 | 7/2007 |
| WO | WO 2012103653 | 8/2012 |
| WO | WO 2013064195 | 5/2013 |
| WO | WO 2014066999 | 5/2014 |
| WO | WO 2015056858 | 4/2015 |

OTHER PUBLICATIONS

GenBank Accession No. ACN99362.1, published Mar. 25, 2009.*
Extended European Search Report dated Sep. 19, 2016 in European Application No. EP20130850207, filed Oct. 29, 2013.
GenBank Accession No. ACN99362.1, [Online] Mar. 26, 2009. Retrieved on Nov. 17, 2016 from; EBI accession No. EMBL: ACN99362.1 https://www.ncbi.nlm.nih.gov/protein/225644312?sat=18&satkey=1856400.
"Carbonate dehydratase [*Sulfurihydrogenibium* sp. Y03A0P1] ", GENKBANK database under ACD 66216.1 (D1), downloaded Jan. 9, 2014.
Allen, John P. "An Enzymic Concept for CO2 Control in Closed Environmental Control Systems", Technical Report AFFDL-TR-65-48, Aug. 1965, 56 pages, Air Force Flight Dynamics Laboratory, Research Technology Division, Air Force Systems Command, Wright-Patterson Air Force Base, Ohio, USA.
Allen, John P. "Investigation of the Enhancement of Carbon Dioxide Absorption by Amines With the Enzyme Carbonic Anhydrase", Technical Report AFFDL-TR-66-23, May 1966, 42 pages, Air Force Flight Dynamics Laboratory, Research Technology Division, Air Force Systems Command, Wright-Patterson Air Force Base, Ohio, USA.
Bhatt et al. "Proton Transfer in a Thr200His Mutant of Human Carbonic Anhydrase II", Proteins, 2005, pp. 239-245, vol. 61.
Broun et al. "Catalytic plasticity of fatty acid modification enzymes underlying chemical diversity of plant lipids", Science, 1998, pp. 1315-1317, vol. 282.
Capasso et al. "Biochemical properties of a novel and highly thermostable bacterial α-carbonic anhydrase from *Sulfurihydrogenibium yellowstonense* Y03A0P1", Journal of Enzyme Inhibition and Medicinal Chemistry, Dec. 2012, pp. 892-897, vol. 27(6).
Chica et al. "Semi-rational approaches to engineering enzyme activity: combining the benefits of directed evolution and rational design", Curr. Opi. Biotechnol., 2005, pp. 378-384, vol. 16.
Chirica et al. "The complete sequence expression in *Escherichia coli*, purification and some properties of carbonic anhydrase from Neisseria gonorrhoeae", European Journal of Biochemistry, 1997, pp. 755-760, vol. 244(3).
Dean et al. "Batch Absorption of CO2 by Free and Microencapsulated Carbonic Anhydrase", Ind. Eng. Chem., Fundam., 1977, pp. 452-458, vol. 16(4).
Devos et al. "Practical limits of function prediction", Proteins, 2000, pp. 98-107, vol. 41.
Di Fiore et al. "X-ray structure of the first 'extremo-α-carbonic anhydrase', a dimeric enzyme from the thermophilic bacterium *Sulfurihydrogenibium* yellowstonense Y03A0P1", Acta Cryst., Jun. 2013, pp. 1150-1159, Section D(69).
Donaldson and Quinn. "Kinetic Constants Determined from Membrane Transport Measurements: Carbonic Anhydrase Activity at High Concentrations", Proc. Nat. Acad. Sci. USA, Dec. 1974, pp. 4995-4999, vol. 71(12).
Ferrell et al. "Amino acid sequence of rabbit carbonic anhydrase II", Biochim. Biophys. Acta., 1978, pp. 1-11, vol. 533.
Fisher et al. "Structural and kinetic characterization of active-site histidine as a proton shuttle in catalysis by human carbonic anhydrase II", Biochem., 2005, pp. 1097-1105, vol. 44(4).
Fisher et al. "Speeding Up Proton Transfer in a Fast Enzyme: Kinetic and Crystallographic Studies on the Effect of Hydrophobic Amino Acid Substitutions in the Active Site of Human Carbonic Anhydrase II", Biochem., 2007, pp. 3803-3813, vol. 46(12).
Genis et al. "Design of a Carbonic Anhydrase IX Active-Site Mimic to Screen Inhibitors for Possible Anti-Cancer Properties", Biochem., 2009, pp. 1322-1331, vol. 48(6).
Giovannelli et al. "Complete genome sequence of *Thermovibrio ammonificans* HB-1(T), a thermophilic, chemolithoautotrophic bacterium isolated from a deep-sea hydrothermal vent", Standards in Genomic Science, 2012, pp. 82-90, vol. 7.
Graf, George. "Regenerative Control of CO2 in Air by Carbonic Anhydrase", Technical Report AFFDL-TR-66-62, May 1966, 182 pages, Air Force Flight Dynamics Laboratory, Research Technology Division, Air Force Systems Command, Wright-Patterson Air Force Base, Ohio, USA.
Gribskov, M. and R. R. Burgess, "Sigma factors from *E. coli*, *B. subtilis*, phage SP01, and phage T4 are homologous proteins", Nucl. Acids Res., 1986, pp. 6745-6763, vol. 14(6).
Guo et al. "Protein tolerance to random amino acid change", Proc.Nat. Acad. Sci., 2004, pp. 9205-9210, vol. 101(25).
Haakansson et al. "Wild-type and E106Q mutant carbonic anhydrase complexed with acetate", Acta Cryst., 1994, pp. 101-104, Section D(50).
Hammarstrom et al. "Pyrene excimer fluorescence as a proximity probe for investigation of residual structure in the unfolded state of human carbonic anhydrase II", FEBS Lett., 1997, pp. 63-68, vol. 420.
Hammarstrom et al. "Structural mapping of an aggregation nucleation site in a molten globule intermediate", J. Biol. Chem., Nov. 1999, pp. 32897-32903, vol. 274(46).
Hammarstrom et al. "Protein compactness measured by fluorescence resonance energy transfer. Human carbonic anhydrase II is considerably expanded by the interaction of GroEL", J. Biol. Chem., Jun. 2001, pp. 21765-21775, vol. 276(24).
Henikoff and Henikoff. "Amino Acid Substitution Matrices from Protein Blocks", Proc. Natl. Acad. Sci. USA, 1992, pp. 10915-10919, vol. 89.
Hunt et al. "Selection of Carbonic Anhydrase Variants Displayed on Phage. Aromatic Residues in Zinc Binding Site Enhance Metal Affinity and Equilibration Kinetics", The Journal of Biological Chemistry, 1997, pp. 20364-20372, vol. 272(33).

(56) References Cited

OTHER PUBLICATIONS

Jackman et al. "Disruption of the Active Site Solvent Network in Carbonic Anhydrase II Decreases the Efficiency of Proton Transfer", Biochem., 1996, pp. 16421-16428, vol. 35(51).
James et al. "The structure of a tetrameric α-carbonic anhydrase from Thermovibrio ammonificans reveals a core formed around intermolecular disulfides that contribute to its thermostability", Acta Cryst., 2014, pp. 2607-2618, Section D(70).
Jo et al. "Bacterial extremo-α-carbonic anhydrases from deep-sea hydrothermal vents as potential biocatalysts for CO2 sequestration", Journal of Molecular Catalysis B: Enzymatic, 2014, pp. 31-39, vol. 109.
Kimchi-Sarfaty et al. "A 'Silent' polymorphism in the MDR1 gene changes substrate specificity", Science, 2007, pp. 525-528, vol. 315.
Krebs et al. "Conformational mobility of His-64 in the Thr-200→Ser mutant of human carbonic anhydrase II", Biochem., 1991, pp. 9153-9160, vol. 30(38).
Krebs et al. "Kinetic and Spectroscopic Studies of Hydrophilic Amino Acid Substitutions in the Hydrophobic Pocket of Human Carbonic Anhydrase II", Biochem., 1993, pp. 4496-4505, vol. 32(17).
Krebs and Fierke. "Determinants of Catalytic Activity and Stability of Carbonic Anhydrase II as Revealed by Random Mutagenesis", J. Bio. Chem., 1993, pp. 948-954, vol. 268 (2).
Martensson et al. "Characterization of Folding Intermediates of Human Carbonic Anhydrase II: Probing Substructure by Chemical Labeling of SH Groups Introduced by Site-Directed Mutagenesis", Biochem., 1993, pp. 224-231, vol. 32(1).
Migliardini et al. "Biomimetic CO2 capture using a highly thermostable bacterial α-carbonic anhydrase immobilized on a polyurethane foam", Journal of Enzyme Inhibition and Medicinal Chemistry, Feb. 2013, pp. 1-6, online edition.
Nackley et al. "Human Caechol-O-Methytransferase haplotypes modulate protein expression by altering mRNA secondary structure", SCIENCE, 2006, pp. 1930-1933, vol. 314.
Nair and Christianson. "Structural consequences of hydrophilic amino acid substitutions in the hydrophobic pocket of human carbonic anhydrase II", Biochem., 1993, pp. 4506-4514, vol. 32(17).
Nakagawa et al. "*Sulfurihydrogenibium yellowstonense* sp. nov., an extremely thermophilic, facultatively heterotrophic, sulfur-oxidizing bacterium from Yellowstone National Park, and emended descriptions of the genus *Sulfurihydrogenibium*, *Sulfurihydrogenibium subterraneum* and *Sulfurihydrogenibium azorense*", International Journal of Systematic and Evolutionary Microbiology, Nov. 2005, pp. 2263-2268, vol. 55(6).
Needleman and Wunsch. "A General Method Applicable to the Search for Similarities in the Amino Acid Sequence of Two Proteins", J. Mol. Biol., 1970, pp. 443-453, vol. 48.
Ng and Henikoff. "Predicting Deleterious Amino Acid Substitutions", Genome Res., 2001, pp. 863-874, vol. 11.
Penders et al. "Kinetics of absorption of carbon dioxide in aqueous MDEA solutions with carbonic anhydrase at 298K", International Journal of Greenhouse Gas Control, 2012, pp. 385-392, vol. 9.
Russo et al. "Kinetic Assessment of Thermostable Carbonic Anhydrase for CO2 Capture Proceses", Chemical Engineering Transactions, Jun. 2012, pp. 181-186, vol. 27.
Russo et al. "Post-combustion carbon capture mediated by carbonic anhydrase", Separation and Purification Technology, Apr. 2013, pp. 331-339, vol. 107.
Sauna et al. "Silent polymorhisms speak: How they affect pharmacogenomics and the treatment of cancer", Cancer Res., 2007, pp. 9609-9612, vol. 67(20).
Scolnick and Christianson. "X-Ray Crystallographic Studies of Alanine-65 Variants of Carbonic Anhydrase II Reveal the Structural Basis of Compromised Proton Transfer in Catalysis", Biochem., Dec. 1996, pp. 16429-16434, vol. 35(51).
Seffernick et al. "Melamine deaminase and Atrazine chlorohydrolase: 98 percent identical but functionally different", J. Bacteriol., 2001, pp. 2405-2410, vol. 183(8).
Sen et al. "Developments in directed evolution for improving enzyme functions", Appl. Biochem. Biotechnol., 2007, pp. 212-223, vol. 143.
Smith and Waterman, "Comparison of Biosequences", Advances in Applied Mathematics, 1981, pp. 482-489, vol. 2.
Stolle et al. "Nucleotide sequence of a cDNA encoding rat brain carbonic anhydrase II and its deduced amino acid sequence", Gene, 1991, pp. 265-267, vol. 109.
Strausberg et al. "Generation and initial analysis of more than 15,000 full-length human and mouse cDNA sequences", PNAS, 2002, pp. 16899-16903, vol. 199(26).
Svensson et al. "Mapping the Folding Intermediate of Human Carbonic Anhydrase II. Probing Substructure by Chemical Reactivity and Spin and Fluorescence Labeling of Engineered Cysteine Residues", Biochem., 1995, pp. 8606-8620, vol. 34(27).
Tu et al. "Kinetic analysis of multiple proton shuttles in the active site of human carbonic anhydrase", J. Biol. Chem., Oct. 2002, pp. 38870-38876, vol. 277(41).
Tweedy et al. "Structure and energetics of a non-proline cis-peptidyl linkage in a proline-202→alanine carbonic anhydrase II variant", Biochem., 1993, pp. 10944-10949, vol. 32(41).
Whisstock et al. "Prediction of protein function from protein sequence", Q. Rev. Biophysics., 2003, pp. 307-340, vol. 36(3).
Witkowski et al. "Conversion of β-ketoacyl synthase to a malonyl decarboxylase by replacement of the active-site cysteine with glutamine", Biochem., 1999, pp. 11643-11650, vol. 38(36).
Xue et al. "Structural analysis of the zinc hydroxide-Thr-199-Glu-106 hydrogen-bond network in human carbonic anhydrase II", Proteins, 1993, pp. 93-106, vol. 17.
Xue et al. "Crystallographic Analysis of Thr-200→ His human carbonic anhydrase II and its complex with the substrate, HCO3", Proteins, 1993, pp. 80-87, vol. 15.
International Search Report dated Jan. 22, 2014 for PCT/CA2013/050818.
Zhang and Cremer. "Chemistry of Hofmeister Anions and Osmolytes", Annu. Rev. Phys. Chem., 2010, pp. 63-83, vol. 61.
Dayhoff, M. O. "Atlas of Protein Sequences and Structure", 1978, pp. 353-358, Ed. 5. Suppl. 3, National Biomedical Research Foundation, Washington D.C., USA.

\* cited by examiner

```
  1  ATGAGAAAAATACTA ATTTCTGCAGTTTTA GTATTATCAAGCATT TCTATATCTTTTGCT
 61  GAGCATGAATGGAGT TATGAAGGTGAAAAG GGACCGGAGCATTGG GCGCAGTTAAAACCT
121  GAATTCTTTTGGTGT AAATTAAAAAATCAA TCTCCTATAAACATT GATAAAAAATATAAA
181  GTTAAAGCAAACCTG CCAAAGTTAAACTTG TACTACAAAACTGCA AAAGAATCAGAAGTA
241  GTAAACAATGGTCAT ACTATTCAGATAAAT ATAAAAGAAGATAAC ACTTTAAACTACCTT
301  GGAGAAAAGTATCAG CTTAAACAGTTTCAT TTCCACACACCAAGT GAACATACAATAGAG
361  AAAAAATCTTATCCG TTGGAAATTCACTTT GTTCATAAAACAGAA GATGGTAAGATTTTG
421  GTCGTTGGTGTAATG GCTAAACTTGGGAAA ACTAATAAAGAGTTA GATAAAATTTTAAAC
481  GTTGCTCCTGCTGAA GAAGGAGAAAAAATT CTTGATAAGAATTTA AATTAAACAATCTT
541  ATACCAAAAGATAAG AGATATATGACATAC TCAGGCTCATTAACC ACTCCACCATGCACT
601  GAAGGTGTAAGATGG ATTGTCTTGAAAAAA CCTATTTCTATATCT AAGCAGCAACTTGAA
661  AAGTTAAAAATCTGTT ATGGTGAATCCTAAC AACAGACCTGTTCAA GAGATTAATTCAAGA
721  TGGATAATTGAAGGA TTTTAA
```

SEQ ID 1

SEQ ID 2

```
  1  M R K I L H S A V L V G P L S S H S I S F A
 21  E H E W S Y E G K E Q P H E W A Q L K P
 41  E F F W C K L K N Q S P I N K E K K Y K
 61  V K A N L P K Y Q L N Y H I K E S E Y V
 81  V N G H T I Q H F V T E N D L H T N Y L
101  G Y K S Q L A K E F H K D G D L H E I E
121  K V P V M E L A K G K T K E D K I K N L
141  V A E K L E A G L V E K L N K L N N P T
161  I P R D W Y M K I Y K G S I N K I P P Q
181  E K W V K R Y L K P H I S S T K Q Q L
201  K S V K T S P N R P V Q E I N S
221  W V G M F *
```

| Accession | Description | Query coverage | Max ident |
|---|---|---|---|
| YP_001930770.1 | Carbonate dehydratase [Sulfurihydrogenibium sp. YO3AOP1] | 100% | 100% |
| YP_002728532.1 | carbonic anhydrase [Sulfurihydrogenibium azorense Az-Fu1] | 99% | 58% |
| YP_002891597.1 | Carbonate dehydratase [Tolumonas auensis DSM 9187] | 98% | 50% |
| ZP_10223335.1 | carbonate dehydratase [Pantoea agglomerans IG1] | 97% | 45% |
| ZP_09513857.1 | carbonic anhydrase [Pantoea sp. SL1_M5] | 97% | 45% |
| ZP_10104441.1 | carbonic anhydrase [Thiothrix nivea DSM 5205] | 99% | 44% |
| YP_003931216.1 | Carbonic anhydrase [Pantoea vagans C9-1] | 97% | 44% |
| ZP_08521545.1 | carbonic anhydrase [Aeromonas caviae Ae398] | 99% | 44% |
| YP_004391460.1 | carbonic anhydrase [Aeromonas veronii B565] | 99% | 47% |
| EKB17868.1 | hypothetical protein HMPREF1168_04095 [Aeromonas veronii AMC34] | 99% | 47% |
| YP_004152175.1 | Carbonate dehydratase [Thermovibrio ammonificans HB-1] | 89% | 49% |
| EKB16017.1 | hypothetical protein HMPREF1167_01111 [Aeromonas veronii AER39] | 99% | 47% |
| EKB29771.1 | hypothetical protein HMPREF1171_00062 [Aeromonas hydrophila SSU] | 99% | 44% |
| ZP_04619781.1 | Carbonic anhydrase [Yersinia aldovae ATCC 35236] | 98% | 47% |
| ZP_04637859.1 | Carbonic anhydrase [Yersinia intermedia ATCC 29909] | 99% | 44% |
| ZP_11085464.1 | hypothetical protein HMPREF1170_03672 [Aeromonas veronii AMC35] | 99% | 46% |
| ZP_10553831.1 | carbonic anhydrase [Pantoea sp. YR343] | 89% | 52% |
| YP_002731211.1 | carbonic anhydrase [Persephonella marina EX-H1] | 99% | 46% |
| YP_003610599.1 | Carbonic anhydrase [Enterobacter cloacae subsp. cloacae ATCC 13047] | 99% | 43% |
| BAL26450.1 | carbonic anhydrase [Azoarcus sp. KH32C] | 89% | 45% |
| YP_004298902.1 | Carbonic anhydrase [Yersinia enterocolitica subsp. palearctica 105.5R(r)] | 99% | 43% |
| ZP_04630767.1 | Carbonate dehydratase [Yersinia frederiksenii ATCC 33641] | 99% | 43% |
| YP_001178406.1 | Carbonate dehydratase [Enterobacter sp. 638] | 96% | 46% |
| YP_003208690.1 | Carbonic anhydrase [Cronobacter turicensis z3032] | 98% | 47% |
| YP_006475540.1 | carbonic anhydrase [Enterobacter cloacae subsp. dissolvens SDM] | 99% | 43% |
| ZP_09039677.1 | carbonic anhydrase [Enterobacter mori LMG 25706] | 96% | 45% |

Figure 2

| Accession | Description | Query coverage | Max ident |
|---|---|---|---|
| ZP_01871701.1 | Carbonic anhydrase [Caminibacter mediatlanticus TB-2] | 99% | 47% |
| ZP_09011677.1 | Carbonic anhydrase [Commensalibacter intestini A911] | 97% | 46% |
| EHI51562.1 | carbonic anhydrase [Aeromonas salmonicida subsp. salmonicida 01-B526] | 93% | 44% |
| YP_857893.1 | carbonic anhydrase [Aeromonas hydrophila subsp. hydrophila ATCC 7966] | 89% | 45% |
| YP_001140784.1 | carbonic anhydrase [Aeromonas salmonicida subsp. salmonicida A449] | 93% | 44% |
| YP_004502929.1 | carbonate dehydratase [Serratia sp. AS12] | 99% | 43% |
| ZP_04642235.1 | Carbonic anhydrase [Yersinia mollaretii ATCC 43969] | 98% | 42% |
| ZP_10101737.1 | carbonic anhydrase [Thiothrix nivea DSM 5205] | 98% | 43% |
| YP_001358482.1 | carbonate dehydratase [Sulfurovum sp. NBC37-1] | 97% | 47% |
| ZP_08823260.1 | Carbonate dehydratase [Thiorhodococcus drewsii AZ1] | 99% | 41% |
| YP_003712986.1 | carbonic anhydrase [Xenorhabdus nematophila ATCC 19061] | 95% | 46% |
| YP_004830445.1 | carbonic anhydrase [Enterobacter asburiae LF7a] | 96% | 45% |
| ZP_10810310.1 | Cah Protein [Enterobacter sp. SST3] | 96% | 46% |
| ZP_06191569.1 | carbonic anhydrase precursor [Serratia odorifera 4Rx13] | 97% | 42% |
| ZP_01221338.1 | putative carbonic anhydrase [Photobacterium profundum 3TCK] | 98% | 46% |
| YP_004953917.1 | carbonic anhydrase [Enterobacter cloacae EcWSU1] | 96% | 45% |
| YP_004214739.1 | carbonate dehydratase [Rahnella sp. Y9602] | 96% | 42% |
| YP_005026081.1 | carbonic anhydrase [Vibrio sp. EJY3] | 98% | 45% |
| YP_002156472.1 | carbonic anhydrase [Vibrio fischeri MJ11] | 97% | 47% |
| YP_131463.1 | carbonic anhydrase [Photobacterium profundum SS9] | 98% | 44% |
| ZP_08830636.1 | extracellular solute-binding protein, family 1 [endosymbiont of Riftia pachyptila] | 98% | 41% |
| YP_942895.1 | carbonate dehydratase [Psychromonas ingrahamii 37] | 98% | 41% |
| EHS91946.1 | carbonic anhydrase [Klebsiella oxytoca 10-5243] | 96% | 46% |
| YP_003443975.1 | carbonic anhydrase [Allochromatium vinosum DSM 180] | 97% | 42% |
| YP_205034.1 | carbonic anhydrase [Vibrio fischeri ES114] | 98% | 46% |
| EGF40970.1 | carbonic anhydrase [Vibrio parahaemolyticus 10329] | 98% | 44% |

Figure 2 (continued)

| Accession | Description | Query coverage | Max ident |
|---|---|---|---|
| EHN70090.1 | carbonic anhydrase [Vibrio fischeri SR5] | 98% | 46% |
| YP_006580462.1 | carbonic anhydrase [Enterobacter cloacae subsp. cloacae ENHKU01] | 96% | 46% |
| EHS90795.1 | carbonic anhydrase [Klebsiella oxytoca 10-5245] | 96% | 46% |
| ZP_05919314.1 | carbonic anhydrase [Pasteurella dagmatis ATCC 43325] | 96% | 45% |
| YP_005202036.1 | carbonic anhydrase [Rahnella aquatilis] | 89% | 44% |
| YP_006413853.1 | carbonic anhydrase [Thiocystis violascens DSM 198] | 99% | 39% |
| YP_06179499.1 | carbonic anhydrase [Vibrio alginolyticus 40B] | 98% | 43% |
| EGF40239.1 | carbonic anhydrase [Vibrio parahaemolyticus 10329] | 98% | 44% |
| EKD34132.1 | hypothetical protein ACD_75CO2456G0005 [uncultured bacterium] | 89% | 44% |
| ZP_08246907.1 | carbonic anhydrase [Neisseria bacilliformis ATCC BAA-1200] | 97% | 44% |
| ZP_05909537.1 | carbonate dehydratase [Vibrio parahaemolyticus AQ4037] | 98% | 44% |
| CBK86838.1 | Carbonic anhydrase [Enterobacter cloacae subsp. cloacae NCTC 9394] | 96% | 43% |
| YP_207719.1 | Cah [Neisseria gonorrhoeae FA 1090] | 97% | 45% |
| ZP_01259505.1 | carbonic anhydrase [Vibrio alginolyticus 12G01] | 98% | 44% |
| ZP_08824124.1 | Carbonate dehydratase [Thiorhodococcus drewsii AZ1] | 99% | 40% |
| ZP_08499859.1 | carbonic anhydrase [Enterobacter hormaechei ATCC 49162] | 96% | 44% |
| YP_393749.1 | carbonate dehydratase [Sulfurimonas denitrificans DSM 1251] | 96% | 44% |
| ZP_08771888.1 | Carbonate dehydratase [Thiocapsa marina 5811] | 97% | 39% |
| EIM35499.1 | carbonic anhydrase [Enterobacter cloacae subsp. cloacae GS1] | 96% | 43% |
| ZP_01258509.1 | carbonic anhydrase [Vibrio alginolyticus 12G01] | 98% | 43% |
| YP_001355839.1 | carbonate dehydratase [Nitratiruptor sp. SB155-2] | 99% | 44% |
| ZP_05029585.1 | carbonic anhydrase [Microcoleus chthonoplastes PCC 7420] | 97% | 44% |
| YP_294256.1 | carbonate dehydratase [Ralstonia eutropha JMP134] | 98% | 40% |
| YP_005016803.1 | carbonate dehydratase [Klebsiella oxytoca KCTC 1686] | 96% | 45% |
| ZP_06179713.1 | carbonic anhydrase [Vibrio alginolyticus 40B] | 98% | 44% |
| YP_001480644.1 | carbonate dehydratase [Serratia proteamaculans 568] | 91% | 42% |

Figure 2 (continued)

SspCA    (SEQ ID# 7)

```
  1  ATGGAACACGAATGGAGCTACGAAGGTGAGAAGGGTCCTGAGCATTGGGCGCAGTTGAAA        60
 61  CCGGAGTTCTTTTGGTGCAAGCTGAAGAATCAATCTCCGATCAACATTGACAAGAAGTAC       120
121  AAAGTCAAAGCGAATCTGCCGAAGCTGAATCTGTATTACAAAACCGCAAAAGAGAGCGAG       180
181  GTTGTGAACAATGGCCACACACTATTCAAATCAACATTAAAGAGGATAACACCCTGAATTAT     240
241  CTGGGTGAAAAGTATCAACTGAAGCAGTTTCATTTTCACACGCCGAGCGAGCATACCATC      300
301  GAGAAGAAGTCGTACCCGTTGGAAATCCACTTCGTTCACAAAACCGAGGATGGTAAAATC      360
361  TTGGTCGTGGGTGTGATGGCCAAACTGGGTAAGACGAATAAAGAGCTGGACAAGATTCTG      420
421  AACGTGGCTCCGGCGGAAGAAGGTGAAAAGATCCTGGACAAAAACCTGAACCTGAACAAC      480
481  CTGATTCCGAAAGATAAACGTTATATGACGTACAGCGGCAGCCTGACCACCCCACCGTGT      540
541  ACGGAAGGCGTTCGTTGGATCGTTCTGAAGAAGCCGATCAGCATTAGCAAACAGCAGTTG     600
601  GAGAAACTGAAAAGCGTCATGTGTCAACCCGAATAATCGCCCGGTTCAAGAAATCAATTCC     660
661  CGTTGGATTATTGAGGGCTTCTAA                                           684
```

Figure 7

SspCA (SEQ ID# 8)

Variant M6X Enzyme (SEQ ID NO: 197)

| | | | | | | | | | | | | | | | | | | | | | |
|---|---|---|---|---|---|---|---|---|---|---|---|---|---|---|---|---|---|---|---|---|---|
| 1 | M | S | H | H | W | G | Y | G | K | H | N | G | P | E | H | W | H | K | D | F | 20 |
| 21 | P | I | A | K | G | E | R | Q | S | P | V | D | I | D | T | H | T | A | K | Y | 40 |
| 41 | D | P | S | L | K | P | L | S | V | S | Y | D | Q | A | T | S | L | R | I | L | 60 |
| 61 | N | N | G | H | T | F | N | V | E | F | D | D | S | Q | D | K | A | V | L | K | 80 |
| 81 | G | G | P | L | D | G | T | Y | R | L | I | Q | F | H | F | H | W | G | S | H | 100 |
| 101 | D | G | Q | G | S | E | H | T | V | D | K | K | K | Y | A | A | E | L | H | L | 120 |
| 121 | V | H | W | N | T | K | Y | G | D | F | G | K | A | V | Q | Q | P | D | G | L | 140 |
| 141 | A | V | L | G | I | F | L | K | V | G | S | A | L | P | G | L | Q | K | V | V | 160 |
| 161 | D | V | L | D | S | I | K | T | K | G | K | S | A | D | F | T | N | F | D | P | 180 |
| 181 | R | G | L | L | P | E | S | L | D | Y | W | T | Y | P | G | S | L | T | T | P | 200 |
| 201 | P | L | L | E | C | V | T | W | I | V | L | K | E | P | I | S | V | S | S | E | 220 |
| 221 | Q | V | S | K | F | R | K | L | N | F | N | G | E | G | E | P | E | E | P | M | 240 |
| 241 | V | D | N | W | R | P | T | Q | P | L | K | N | R | Q | I | K | A | S | F | K | 260 |

Figure 9

```
#=======================================
# Aligned_sequences: 2
# 1: SspCA
# 2: M6X
# Matrix: EBLOSUM62
# Gap_penalty: 10.0
# Extend_penalty: 0.5

# Length: 266
# Identity:      91/266 (34.2%)
# Similarity:   132/266 (49.6%)
# Gaps:          45/266 (16.9%)
# Score: 371.5
#=======================================
SspCA    1 MEHEWSYEGEKGPEHWAQLKPEFFWCKLKNQSPINID-KKYKVKANLPKL     49
           |.|.|.|....|||||.:   :|...|.:.|||::||  ...|...:|..|
M6X      1 MSHHWGYGKHNGPEHWHK---DFPIAKGERQSPVDIDTHTAKYDPSLKPL     47

SspCA   50 NLYYKTAKESEVVNNGHTIQINIKEDNTLNY-------LGEKYQLKQFHF     92
           ::.|...|.....::|||||  .|::.|::.:.      |....|:|.||||
M6X     48 SVSYDQATSLRILNNGHT--FNVEFDDSQDKAVLKGGPLDGTYRLIQFHF     95

SspCA   93 H------TPSEHTIEKKSYPLEIHFVH------------KTEDGKILVVG    124
           |       ..||||::||.|...|:|.||             :..||  :.|:|
M6X     96 HWGSHDGQGSEHTVDKKKYAAELHLVHWNTKYGDFGKAVQQPDG-LAVLG    144

SspCA  125 VMAKLGKTNKELDKILNVAPA--EEGEKILDKNLNLNNLIPKDKRYMTYS    172
           :..|:|.....|.|:::|...   .:|......|.:....|:|:...|.||.
M6X    145 IFLKVGSALPGLQKVVDVLDSIKTKGKSADFTNFDPRGLLPESLDYWTYP    194

SspCA  173 GSLTTPPCTEGVRWIVLKKPISISKQQLEKLKSVMVN----------PNN    212
           ||||||||..|.|.|||||:|||:|.:|:.|.:.:...|            .|.
M6X    195 GSLTTPPLLECVTWIVLKEPISVSSEQVSKFRKLNFNGEGEPEEPMVDNW    244

SspCA        213 RPVQEINSRWIIEGF-    227
                 ||.|..:.:|.|...|
M6X          245 RPTQPLKNRQIKASFK    260

TECHNIQUES FOR $CO_2$ CAPTURE USING *SULFURIHYDROGENIBIUM* SP. CARBONIC ANHYDRASE

CROSS REFERENCE TO RELATED APPLICATIONS

This application is the U.S. National Phase of International Application No. PCT/CA2013/050818, filed Oct. 29, 2013, designating the U.S. and published in English as WO 2014/066999 A1 on May 8, 2014 which claims the benefit of U.S. Provisional Patent Application No. 61/719,710, filed Oct. 29, 2012. Any and all applications for which a foreign or domestic priority claim is identified in the Application Data Sheet as filed with the present application are hereby incorporated by reference under 37 CFR 1.57.

TECHNICAL FIELD

The technical field relates to $CO_2$ capture and the use of *Sulfurihydrogenibium* sp. carbonic anhydrase (SspCA) and mutants for catalyzing the hydration reaction of $CO_2$ into bicarbonate and hydrogen ions or catalyzing the desorption reaction to produce a $CO_2$ gas.

BACKGROUND

Increasingly dire warnings of the dangers of climate change by the world's scientific community combined with greater public awareness and concern over the issue has prompted increased momentum towards global regulation aimed at reducing man-made greenhouse gas (GHGs) emissions, most notably carbon dioxide. Ultimately, a significant cut in North American and global $CO_2$ emissions will require reductions from the electricity production sector, the single largest source of $CO_2$ worldwide. According to the International Energy Agency's (IEA) GHG Program, as of 2006 there were nearly 5,000 fossil fuel power plants worldwide generating nearly 11 billion tons of $CO_2$, representing nearly 40% of total global anthropogenic $CO_2$ emissions. Of these emissions from the power generation sector, 61% were from coal fired plants. Although the long-term agenda advocated by governments is replacement of fossil fuel generation by renewables, growing energy demand, combined to the enormous dependence on fossil generation in the near term dictates that this fossil base remain operational. Thus, to implement an effective GHG reduction system will require that the $CO_2$ emissions generated by this sector be mitigated, with carbon capture and storage (CCS) providing one of the best known solutions.

The CCS process removes $CO_2$ from a $CO_2$ containing gas and involves the production of a highly concentrated $CO_2$ gas stream which is compressed and transported to a geologic sequestration site. This site may be a depleted oil field, a saline aquifer or any suitable storage site. Sequestration in oceans and mineral carbonation are two alternate ways to sequester $CO_2$ that are in the research phase. Captured $CO_2$ can also be used for enhanced oil recovery or for carbonation of alkaline waste streams for sequestration as mineral solids.

Conventional technologies for $CO_2$ capture are based primarily on the use of aqueous amine (e.g. alkanolamines) which is circulated through two main distinct units: an absorption unit coupled to a desorption (or stripping) unit. However in the context of low $CO_2$ partial pressures encountered in gases from combustion, these conventional technologies give rise to processes with high energy penalty and thus high operational expenditure, as it is the case with monoethanolamine (MEA), or processes with high capital expenditure, as for the case of kinetically limited absorption solutions resulting in large equipment such as with methydiethanolamine (MDEA) for example. Higher pressure $CO_2$ separation from process streams seen in $H_2$ production or gasification is typically usually easier to achieve due to the higher pressures in such processes.

Carbonic anhydrase is an enzyme that has been used for $CO_2$ absorption applications. Carbonic anhydrase is not just a single enzyme form, but a broad group of metalloproteins that exists in genetically unrelated families of isoforms, α, β, γ, δ and ε. Different classes, isoforms and variants of carbonic anhydrase have been used in order to catalyze the hydration reaction of $CO_2$ into bicarbonate and hydrogen ions and the bicarbonate dehydration reaction into $CO_2$ and water, as follows:

$$CO_2 + H_2O \leftrightarrow H^+ + HCO_3^- \quad \text{(Reaction 1)}$$

Under optimum conditions, the catalyzed turnover rate of the hydration reaction can reach $1 \times 10^6$ molecules/second.

However, there are several challenges related to the use of carbonic anhydrase in $CO_2$ capture operations. For instance, the temperature stability in time, the chemical resistance and the activity of the carbonic anhydrase under process conditions are factors that have an impact on process design, process performance and operating costs.

There is thus a need to overcome at least some of the challenges related to the use of carbonic anhydrase for $CO_2$ capture.

SUMMARY

The present invention provides a recombinant carbonic anhydrase polypeptide comprising an amino acid sequence having at least 65% identity with SEQ ID NO: 8, or a functional derivative thereof.

The present invention provides a recombinant carbonic anhydrase polypeptide comprising an amino acid sequence having at least 65% identity with SEQ ID NO: 8 and comprising at least one amino acid difference relative to SEQ ID NO: 8 at a position selected from the group consisting of X18; X20; X38; X52; X57; X82; X100; X130; X150 and X181, wherein X represents an amino acid, or a functional derivative thereof.

The recombinant carbonic anhydrase polypeptide described therein, comprising an amino acid sequence having at least 65% identity of SEQ ID NO: 8 and comprising at least two amino acid differences relative to SEQ ID NO: 8 at positions selected from the group consisting of X18; X20; X38; X52; X57; X82; X100; X130; X150 and X181, or a functional derivative thereof.

The recombinant carbonic anhydrase polypeptide described therein, comprising an amino acid sequence having at least 65% identity with SEQ ID NO: 8 and comprising at least three amino acid differences relative to SEQ ID NO: 8 at positions selected from the group consisting of X18; X20; X38; X52; X57; X82; X100; X130; X150 and X181, or a functional derivative thereof.

The recombinant carbonic anhydrase polypeptide described therein comprising an amino acid sequence having at least 65% identity with SEQ ID NO: 8 and comprising at least four amino acid differences relative to SEQ ID NO: 8 at positions selected from the group consisting of X18; X20; X38; X52; X57; X82; X100; X130; X150 and X181, or a functional derivative thereof.

The recombinant carbonic anhydrase polypeptide described therein, comprising an amino acid sequence having at least 65% identity with SEQ ID NO: 8 and comprising at least five amino acid differences relative to SEQ ID NO: 8 at positions selected from the group consisting of X18; X20; X38; X52; X57; X82; X100; X130; X150 and X181, or a functional derivative thereof.

The recombinant carbonic anhydrase polypeptide described therein, comprising an amino acid sequence having at least 65% identity with SEQ ID NO: 8 and comprising at least six amino acid differences relative to SEQ ID NO: 8 at positions selected from the group consisting of X18; X20; X38; X52; X57; X82; X100; X130; X150 and X181, or a functional derivative thereof.

The recombinant carbonic anhydrase polypeptide described therein, comprising an amino acid sequence having at least 65% identity with SEQ ID NO: 8 and comprising at least seven amino acid differences relative to SEQ ID NO: 8 at positions selected from the group consisting of X18; X20; X38; X52; X57; X82; X100; X130; X150 and X181, or a functional derivative thereof.

The recombinant carbonic anhydrase polypeptide described therein, comprising an amino acid sequence having at least 65% identity with SEQ ID NO: 8 and comprising at least eight amino acid differences relative to SEQ ID NO: 8 at positions selected from the group consisting of X18; X20; X38; X52; X57; X82; X100; X130; X150 and X181, or a functional derivative thereof.

The recombinant carbonic anhydrase polypeptide described therein, comprising an amino acid sequence having at least 65% identity with SEQ ID NO: 8 and comprising at least nine amino acid differences relative to SEQ ID NO: 8 at positions selected from the group consisting of X18; X20; X38; X52; X57; X82; X100; X130; X150 and X181, or a functional derivative thereof.

The recombinant carbonic anhydrase polypeptide described therein, comprising an amino acid sequence having at least 65% identity with SEQ ID NO: 8 and comprising at least ten amino acid differences relative to SEQ ID NO: 8 at positions selected from the group consisting of X18; X20; X38; X52; X57; X82; X100; X130; X150 and X181, or a functional derivative thereof.

The recombinant carbonic anhydrase polypeptide described therein, comprising an amino acid sequence having at least 65% identity with SEQ ID NO: 8 and comprising amino acid differences relative to SEQ ID NO: 8 selected from the group consisting of Q18X; K20X; K38X; Y52X; K57X; G82X; I100X; G130X; K150X and T181X, wherein Q, K, G, I, Y and T are known amino acids and X is any amino acid, or a functional derivative thereof.

The recombinant carbonic anhydrase polypeptide described therein, comprising an amino acid sequence having at least 65% identity with SEQ ID NO: 8 and comprising amino acid differences relative to SEQ ID NO: 8 selected from the group consisting of X18A; X18C, X18F, X18L; X18R; X18S, X18T, X18W; X20A; X20G; X20L; X20N; X20R; X20S, X20T, X20W; X38A; X38D; X38G; X38L; X38N; X38P; X38R, X38S, X38W; X52C; X52E; X52G; X52P; X52T; X57A, X57G; X57L, X57N; X57P; X57R; X57S; X57V; X82C; X82E; X100A; X100E, X100N; X100S, X100V; X100Y; X130A; X130Q; X130L; X150A; X150I; X150N; X150S; X181Q; X181L; X181M; X181R, wherein A, F, L, R, S, G, N, T, D, P, C, E, S, V, W, Y, I, Q and M are known amino acids, or a functional derivative thereof.

The recombinant carbonic anhydrase polypeptide described therein, comprising an amino acid sequence having at least 65% identity with SEQ ID NO: 8 and comprising amino acid differences relative to SEQ ID NO: 8 selected from the group consisting of Q18A; Q18C, Q18F, Q18L; Q18R; Q18S, Q18T, Q18W; K20A; K20G; K20L; K20N; K20R; K20S; K20T, K20W; K38A; K38D; K38G; K38L; K38N; K38P; K38R, K38S, K38W; Y52C; Y52E; Y52G; Y52P; Y52T; K57A, K57G; K57L, K57N; K57P; K57R; K57S; K57V; G82C; G82E; I100A; I100E, I100N; I100S; I100V, I100Y; G130A; G130C; G130L; K150A; K150I; K150N; K150S; T181Q; T181L; T181M; T181R, wherein Q, K, G, Y, I and T are known amino acids, or a functional derivative thereof.

The recombinant carbonic anhydrase polypeptide described therein, comprising an amino acid sequence having at least 70% identity with SEQ ID NO: 8, or a functional derivative thereof.

The recombinant carbonic anhydrase polypeptide described therein, comprising an amino acid sequence having at least 75% identity with SEQ ID NO: 8, or a functional derivative thereof.

The recombinant carbonic anhydrase polypeptide described therein, comprising an amino acid sequence having at least 80% identity with SEQ ID NO: 8, or a functional derivative thereof.

The recombinant carbonic anhydrase polypeptide described therein, comprising an amino acid sequence having at least 85% identity with SEQ ID NO: 8, or a functional derivative thereof.

The recombinant carbonic anhydrase polypeptide described therein, comprising an amino acid sequence having at least 90% identity with SEQ ID NO: 8, or a functional derivative thereof.

The recombinant carbonic anhydrase polypeptide described therein, comprising an amino acid sequence having at least 91% identity with SEQ ID NO: 8, or a functional derivative thereof.

The recombinant carbonic anhydrase polypeptide described therein, comprising an amino acid sequence having at least 92% identity with SEQ ID NO: 8, or a functional derivative thereof.

The recombinant carbonic anhydrase polypeptide described therein, comprising an amino acid sequence having at least 93% identity with SEQ ID NO: 8, or a functional derivative thereof.

The recombinant carbonic anhydrase polypeptide described therein, comprising an amino acid sequence having at least 94% identity with SEQ ID NO: 8, or a functional derivative thereof.

The recombinant carbonic anhydrase polypeptide described therein, comprising an amino acid sequence having at least 95% identity with SEQ ID NO: 8, or a functional derivative thereof.

The recombinant carbonic anhydrase polypeptide described therein, comprising an amino acid sequence having at least 96% identity with SEQ ID NO: 8, or a functional derivative thereof.

The recombinant carbonic anhydrase polypeptide described therein, comprising an amino acid sequence having at least 97% identity with SEQ ID NO: 8, or a functional derivative thereof.

The recombinant carbonic anhydrase polypeptide described therein, comprising an amino acid sequence having at least 98% identity with SEQ ID NO: 8, or a functional derivative thereof.

The recombinant carbonic anhydrase polypeptide described therein, comprising an amino acid sequence having at least 99% identity with SEQ ID NO: 8, or a functional derivative thereof.

The recombinant carbonic anhydrase polypeptide described therein, comprising an amino acid sequence having at least 99.5% identity with SEQ ID NO: 8, or a functional derivative thereof.

The recombinant carbonic anhydrase polypeptide described therein, comprising additional neutral mutations, or a functional derivative thereof.

The recombinant carbonic anhydrase polypeptide described therein, which further comprises at least one amino acid difference relative to SEQ ID NO: 8 selected from the group consisting of E14D; G65S; K88E; K114I; E116D; V122I; M126L; G148A; N155I and S205C, or a functional derivative thereof.

The invention provides a carbonic anhydrase polypeptide comprising the sequence as set forth in SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162, SEQ ID NO: 164, SEQ ID NO: 166, SEQ ID NO: 168, SEQ ID NO: 170, SEQ ID NO: 172, SEQ ID NO: 174, SEQ ID NO: 176, SEQ ID NO: 178, SEQ ID NO: 180, SEQ ID NO: 182, SEQ ID NO: 184, SEQ ID NO: 186, SEQ ID NO: 188, SEQ ID NO: 190, SEQ ID NO: 192, SEQ ID NO: 194, SEQ ID NO: 196, SEQ ID NO: 200, SEQ ID NO: 202, SEQ ID NO: 204, SEQ ID NO: 206, SEQ ID NO: 208 or a functional derivative thereof comprising an amino acid sequence having at least 60%, 65%, 70%, 75%, 80%, 85%, 86%, 87%, 88%, 89%, 90%, 91%, 92%, 93%, 94%, 95%, 96%, 97%, 98%, 99% or 99.5% identity with the sequence as set forth in SEQ ID NO: 8.

The functional derivative thereof may include an amino acid sequence having at least 60%, 65%, 70%, 75%, 80%, 85%, 86%, 87%, 88%, 89%, 90%, 91%, 92%, 93%, 94%, 95%, 96%, 97%, 98% 99% or 99.5% identity with the sequence as set forth in SEQ ID NO:1 or SEQ ID NO: 8.

The functional derivative thereof may include an amino acid sequence having at least 60%, 65%, 70%, 75%, 80%, 85%, 86%, 87%, 88%, 89%, 90%, 91%, 92%, 93%, 94%, 95%, 96%, 97%, 98%, 99 or 99.5% identity with the sequence as set forth in SEQ ID NO: 8.

In some aspects, the carbonic anhydrase polypeptide of the invention is neither SEQ ID NO:1 nor SEQ ID No. 8.

In some aspects, the recombinant carbonic anhydrase polypeptide described therein is different from SEQ ID NO: 2 or SEQ ID NO: 8.

In some aspects, the recombinant polypeptide of the invention has an improved property relative to the same property of the polypeptide of SEQ ID NO: 8; selected from one or more of:
a. Improved stability and or activity and or solubility in presence of sodium ion;
b. Improved stability and or activity and or solubility in presence of potassium ion
c. Improved stability and or activity and or solubility in presence of carbonate ion;
d. Improved stability and or activity and or solubility under high pH conditions;
e. Improved stability and or activity and or solubility under high temperature conditions and
f. Improved pH-activity profile.

In some aspects, there is provided a recombinant polypeptide of the invention, wherein the SspCA, within its lifetime, transforms at least $4.3 \times 10^7$ mmole·m$^{-2}$·bar$^{-1}$ of $CO_2$.

The present invention provides a polynucleotide comprising a nucleotide sequence encoding the carbonic anhydrase polypeptide of the invention.

The present invention provides a polynucleotide comprising a nucleotide sequence encoding the carbonic anhydrase polypeptide of the invention, such as SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, SEQ ID NO: 169, SEQ ID NO: 171, SEQ ID NO: 173, SEQ ID NO: 175, SEQ ID NO: 177, SEQ ID NO: 179, SEQ ID NO: 181, SEQ ID NO: 183, SEQ ID NO: 185, SEQ ID NO: 187, SEQ ID NO: 189, SEQ ID NO: 191, SEQ ID NO: 193, SEQ ID NO: 195, SEQ ID NO: 199, SEQ ID NO: 201, SEQ ID NO: 203, SEQ ID NO: 205, or SEQ ID NO: 207.

In some aspects, there is an expression or cloning vector comprising a nucleotide sequence encoding the carbonic anhydrase polypeptide as defined therein.

In some aspects, there is a transgenic cell comprising the expression or cloning vector as defined therein.

The present invention provides various techniques related to the use of the carbonic anhydrase polypeptide as defined therein for removing $CO_2$ from a $CO_2$-containing effluent.

The present invention provides various techniques related to the use of Ssp carbonic anhydrase (SspCA) for $CO_2$ capture and/or catalyzing the absorption of $CO_2$ from a gas into a liquid phase.

In some aspects, there is a use of the carbonic anhydrase polypeptide as defined therein for removing $CO_2$ from a $CO_2$-containing effluent.

In some aspects, there is a use of the carbonic anhydrase polypeptide comprising the sequence as set forth in SEQ ID NO: 2, or functional derivative thereof.

In some aspects, there is a use of the carbonic anhydrase polypeptide comprising the sequence as set forth in SEQ ID NO: 8, or functional derivative thereof.

In some aspects, there is a method for absorbing $CO_2$ from a $CO_2$-containing gas, comprising: contacting the $CO_2$-containing gas with an aqueous absorption solution to dissolve the $CO_2$ into the aqueous absorption solution; providing a *Sulfurihydrogenibium* sp. carbonic anhydrase (SspCA) or functional derivative thereof to catalyze the hydration reaction of the dissolved $CO_2$ into bicarbonate and hydrogen ions; and providing operating conditions such that the SspCA displays enhanced stability and/or activity.

In some aspects, there is a method for absorbing $CO_2$ from a $CO_2$-containing gas, comprising:
contacting the $CO_2$-containing gas with an aqueous absorption solution to dissolve the $CO_2$ into the aqueous absorption solution; and
providing the *Sulfurihydrogenibium* sp. carbonic anhydrase (SspCA) described therein to catalyze the hydration reaction of the dissolved $CO_2$ into bicarbonate and hydrogen ions.

In some aspects, the method of the invention for absorbing $CO_2$ from a $CO_2$-containing gas, comprises the use of SspCA of SEQ ID NO: 2 or SEQ ID NO: 8.

In some aspects, the SspCA displays enhanced stability and/or activity compared to the activity of SspCA of SEQ ID NO: 8.

In some aspects, the SspCA provides an enhanced $CO_2$ flux of at least 8.5 or 22 times a corresponding $CO_2$ flux with no enzyme.

In some aspects, the SspCA provides an enhanced $CO_2$ flux of up to 22 times a corresponding $CO_2$ flux with no enzyme.

In some aspects, the invention provides a method described therein, wherein the at least one absorption compound comprises a primary amine, a secondary amine, a tertiary amine, a primary alkanolamine, a secondary alkanolamine, a tertiary alkanolamine, a primary amino acid, a secondary amino acid, a tertiary amino acid, dialkylether of polyalkylene glycols, dialkylether or dimethylether of polyethylene glycol, amino acid or a derivative thereof, monoethanolamine (MEA), 2-amino-2-methyl-1-propanol (AMP), 2-(2-aminoethylamino)ethanol (AEE), 2-amino-2-hydroxymethyl-1,3-propanediol (Tris or AHPD), N-methyldiethanolamine (MDEA), dimethylmonoethanolamine (DMMEA), diethylmonoethanolamine (DEMEA), triisopropanolamine (TIPA), triethanolamine (TEA), DEA, DIPA, MMEA, TIA, TBEE, HEP, AHPD, hindered diamine (HDA), bis-(tertiarybutylaminoethoxy)-ethane (BTEE), ethoxyethoxyethanol-tertiarybutylamine (EEETB), bis-(tertiarybutylaminoethyl)ether, 1,2-bis-(tertiarybutylaminoethoxy)ethane and/or bis-(2-isopropylaminopropyl)ether, or a combination thereof.

In some aspects, the invention provides a method described therein, wherein the at least one absorption compound comprises a primary amine, a secondary amine, a tertiary amine, a primary alkanolamine, a secondary alkanolamine, a tertiary alkanolamine, a primary amino acid, a secondary amino acid, a tertiary amino acid or a combination thereof.

In some aspects, the invention provides a method described therein, wherein the at least one absorption compound comprises dialkylether of polyalkylene glycols, dialkylether or dimethylether of polyethylene glycol, amino acid or derivative thereof or a combination thereof.

In some aspects, the invention provides a method described therein, wherein the at least one absorption compound comprises piperazine or derivatives thereof.

In some aspects, the invention provides a method described therein, wherein the piperazine or derivatives thereof are substituted by at least one of alkanol group.

In some aspects, the invention provides a method described therein, wherein the at least one absorption compound comprises monoethanolamine (MEA), 2-amino-2-methyl-1-propanol (AMP), 2-(2-aminoethylamino)ethanol (AEE), 2-amino-2-hydroxymethyl-1,3-propanediol (Tris or AHPD), N-methyldiethanolamine (MDEA), dimethylmonoethanolamine (DMMEA), diethylmonoethanolamine (DEMEA), triisopropanolamine (TIPA), triethanolamine (TEA), DEA, DIPA, MMEA, TIA, TBEE, HEP, AHPD, hindered diamine (HDA), bis-(tertiarybutylaminoethoxy)-ethane (BTEE), ethoxyethoxyethanol-tertiarybutylamine (EEETB), bis-(tertiarybutylaminoethyl)ether, 1,2-bis-(tertiarybutylaminoethoxy)ethane and/or bis-(2-isopropylaminopropyl)ether.

In some aspects, the invention provides a method described therein, wherein the at least one absorption compound comprises an amino acid or derivative thereof.

In some aspects, the invention provides a method described therein, wherein the amino acid or derivative thereof comprises glycine, proline, arginine, histidine, lysine, aspartic acid, glutamic acid, methionine, serine, threonine, glutamine, cysteine, asparagine, valine, leucine, isoleucine, alanine, tyrosine, tryptophan, phenylalanine, taurine, N,cyclohexyl 1,3-propanediamine, N-secondary butyl glycine, N-methyl N-secondary butyl glycine, diethylglycine, dimethylglycine, sarcosine, methyl taurine, methyl-$\alpha$-aminopropionicacid, N-($\beta$-ethoxy)taurine, N-($\beta$-aminoethyl)taurine, N-methyl alanine, 6-aminohexanoic acid, potassium or sodium salt of the amino acid or a combination thereof.

In some aspects, the invention provides a method described therein, wherein the absorption compound comprises a carbonate compound.

In some aspects, the invention provides a method described therein, wherein the absorption compound comprises sodium carbonate, potassium carbonate or MDEA.

In some aspects, the invention provides a method described therein, wherein the absorption compound comprises sodium carbonate.

In some aspects, the invention provides a method described therein, wherein the absorption compound comprises potassium carbonate.

In some aspects, the invention provides a method described therein, wherein the temperature of the absorption solution is at least 10° C.

In some aspects, the invention provides a method described therein, wherein the temperature of the absorption solution is at least 25° C.

In some aspects, the step of contacting is performed at a temperature between about 10° C. and about 98° C., between about 35° C. and about 80° C., between about 40° C. and about 70° C., or between about 60° C. and about 65° C., optionally at 10° C., 20° C., 30° C., 40° C., 50° C., 60°

C., 70° C., 80° C. or 98° C. or any other value in between. The absorption solution may include an absorption compound, which may include sodium or potassium carbonate.

In some aspects, the concentration of the SspCA or functional derivative is between about 0.1 g/L and about 50 g/L, optionally between about 0.3 g/L and about 10 g/L in the absorption solution.

In some aspects, the pH of the absorption solution is between about 8 and about 11.

In some aspects, the $CO_2$ loading is between about 0.05 and about 1 mol $CO_2$/mol amine or mol $CO_2$/mol cation.

In some aspects, the method described therein further comprises subjecting the ion-rich solution to desorption to produce a regenerated absorption solution and a $CO_2$ gas stream.

In some aspects, at least a portion of the SspCA is a component of the absorption solution and the ion-rich solution and catalyzes the desorption reaction.

In some aspects, the absorption is operated at a temperature between about 10° C. and about 98° C., optionally between about 35° C. and about 80° C., between about 40° C. and about 70° C., or between about 60° C. and about 65° C., optionally at 10° C., 20° C., 30° C., 40° C., 50° C., 60° C., 70° C., 80° C. or 98° C. or any other value in between.

In some aspects, the desorption is operated at a temperature between about 30° C. and about 110° C., optionally between about 40° C. and about 100° C. or between about 45° C. and about 95° C. Desorption operation can be operated under a wide range of pressure from 0.05 bar up to 50 bars.

In some aspects, the absorption solution includes at least one absorption compound. The at least one absorption compound may include a primary amine, a secondary amine, a tertiary amine, a primary alkanolamine, a secondary alkanolamine, a tertiary alkanolamine, a primary amino acid, a secondary amino acid, a tertiary amino acid, a carbonate or a combination thereof. The at least one absorption compound may include dialkylether of polyalkylene glycols, dialkylether or dimethylether of polyethylene glycol, amino acid or derivative thereof or a combination thereof. The at least one absorption compound may include piperazine or derivative thereof, which may be substituted by at least one of alkanol group. The at least one absorption compound may include monoethanolamine (MEA), 2-amino-2-methyl-1-propanol (AMP), 2-(2-aminoethyl-amino)ethanol (AEE), 2-amino-2-hydroxymethyl-1,3-propanediol (Tris), N-methyldiethanolamine (MDEA), dimethylmonoethanolamine (DMMEA), diethylmonoethanolamine (DEMEA), triisopropanolamine (TIPA), triethanolamine (TEA), DEA, DIPA, methyl monoethanolamine (MMEA), TIA, TBEE, HEP, AHPD, hindered diamine (HDA), bis-(tertiarybutylaminoethoxy)-ethane (BTEE), ethoxyethoxyethanol-tertiarybutylamine (EEETB), bis-(tertiarybutylaminoethyl)ether, 1,2-bis-(tertiarybutylaminoethoxy)ethane and/or bis-(2-isopropylaminopropyl)ether. The at least one absorption compound may include an amino acid or derivative thereof, which may include glycine, proline, arginine, histidine, lysine, aspartic acid, glutamic acid, methionine, serine, threonine, glutamine, cysteine, asparagine, valine, leucine, isoleucine, alanine, tyrosine, tryptophan, phenylalanine, taurine, N,cyclohexyl 1,3-propanediamine, N-secondary butyl glycine, N-methyl N-secondary butyl glycine, diethylglycine, dimethylglycine, sarcosine, methyl taurine, methyl-α-amino-propionicacid, N-(β-ethoxy)taurine, N-(β-aminoethyl)taurine, N-methyl alanine, 6-aminohexanoic acid, potassium or sodium salt of the amino acid, sodium carbonate, potassium carbonate or a combination thereof.

In some aspects, the method further includes subjecting the ion-rich solution to desorption to produce a regenerated absorption solution and a $CO_2$ gas stream. At least a portion of the SspCA may be a component of the absorption solution and the ion-rich solution and catalyzes the desorption reaction.

In some aspects, there may be a method for $CO_2$ capture, including:
  in an absorption stage:
    contacting a $CO_2$-containing gas with an aqueous absorption solution to dissolve the $CO_2$ into the aqueous absorption solution;
    providing *Sulfurihydrogenibium* sp. carbonic anhydrase (SspCA) or functional derivative thereof in the absorption solution to catalyze the hydration reaction of the dissolved $CO_2$ into bicarbonate and hydrogen ions, thereby producing an ion-rich solution comprising at least some of the SspCA and a $CO_2$-depleted gas; and/or
  in a desorption stage:
    providing conditions for treating the ion-rich solution comprising at least some of the SspCA, or functional derivative thereof so as to catalyze the desorption of $CO_2$ gas from the ion-rich solution, thereby producing a regenerated absorption solution and a $CO_2$ gas stream.

In some aspects, there may be a method for $CO_2$ capture, including:
  in an absorption stage:
    contacting a $CO_2$-containing gas with an aqueous absorption solution to dissolve the $CO_2$ into the aqueous absorption solution;
    providing *Sulfurihydrogenibium* sp. carbonic anhydrase (SspCA) of the invention or functional derivative thereof in the absorption solution to catalyze the hydration reaction of the dissolved $CO_2$ into bicarbonate and hydrogen ions, thereby producing an ion-rich solution comprising at least some of the SspCA and a $CO_2$-depleted gas; and/or
  in a desorption stage:
    providing conditions for treating the ion-rich solution comprising at least some of the SspCA of the invention, or functional derivative thereof so as to catalyze the desorption of $CO_2$ gas from the ion-rich solution, thereby producing a regenerated absorption solution and a $CO_2$ gas stream.

In some aspects, the absorption stage may be operated with at least one of the following absorption operating parameters:
  absorption temperature in between about 10° C. and about 98° C.;
  concentration of an absorption compound in the absorption solution between about 0.1M and about 5M;
  pH of the absorption solution in between about 8 and about 11; and/or
  $CO_2$ loading in between about 0.05 and about 1 mol $CO_2$/mol amine or mol $CO_2$/mol cation.

In some aspects, the desorption stage is operated with the following desorption operating parameter: desorption temperature in between about 30° C. and about 110° C.

The absorption stage and desorption stage may be operated within an overall operating temperature zone wherein the SspCA or functional derivative thereof displays enhanced temperature stability and/or activity and/or an overall enhancement of the use of the enzyme.

The absorption stage and desorption stage are operated within an overall operating temperature zone wherein the SspCA or functional derivative thereof displays enhanced temperature stability.

In some aspects, there is a method for desorption of $CO_2$ from a solution comprising bicarbonate and hydrogen ions, comprising providing conditions for desorption of the $CO_2$ in the presence of a *Sulfurihydrogenibium* sp. carbonic anhydrase (SspCA) or functional derivative thereof, so as to catalyze the desorption of $CO_2$ gas from the solution, thereby producing an ion-depleted solution and a $CO_2$ gas stream.

In some aspects, there is a method for stripping $CO_2$ from a bicarbonate-containing aqueous absorption solution, comprising: contacting the bicarbonate-containing solution with a $CO_2$ free gas to transform the bicarbonate ion back into $CO_2$ in the absorption solution and desorb it so it is transferred into the gas; providing a *Sulfurihydrogenibium* sp. carbonic anhydrase (SspCA) or functional derivative thereof to catalyze the dehydration reaction of the bicarbonate and hydrogen ions into $CO_2$ and water; and providing operating conditions such that the SspCA or functional derivative displays enhanced stability and/or activity.

In some aspects, there is a system for absorbing $CO_2$ from a $CO_2$-containing gas, comprising:
an absorption unit comprising:
  a gas inlet for receiving the $CO_2$-containing gas;
  a liquid inlet for receiving an aqueous absorption solution;
  a reaction chamber for contacting the $CO_2$-containing gas with the aqueous absorption solution to dissolve the $CO_2$ into the aqueous absorption solution, wherein *Sulfurihydrogenibium* sp. carbonic anhydrase (SspCA) or functional derivative thereof is present for catalyzing the hydration reaction of the dissolved $CO_2$ into bicarbonate and hydrogen ions, thereby producing an ion-rich solution and a $CO_2$-depleted gas;
  a liquid outlet for releasing the ion-rich solution; and
  a gas outlet for releasing the $CO_2$-depleted gas.

In some aspects, there is a system for absorbing $CO_2$ from a $CO_2$-containing gas, comprising:
an absorption unit comprising:
  a gas inlet for receiving the $CO_2$-containing gas;
  a liquid inlet for receiving an aqueous absorption solution;
  a reaction chamber for contacting the $CO_2$-containing gas with the aqueous absorption solution to dissolve the $CO_2$ into the aqueous absorption solution, wherein *Sulfurihydrogenibium* sp. carbonic anhydrase (SspCA) of the invention or functional derivative thereof is present for catalyzing the hydration reaction of the dissolved $CO_2$ into bicarbonate and hydrogen ions, thereby producing an ion-rich solution and a $CO_2$-depleted gas;
  a liquid outlet for releasing the ion-rich solution; and
  a gas outlet for releasing the $CO_2$-depleted gas.

The system may further include a regeneration stage for regenerating the ion-rich solution. The regeneration stage may include a desorption unit and/or a mineralization unit.

The system may also include a temperature regulator for regulating the temperature of the absorption unit to promote enhanced stability and/or activity of the SspCA or functional derivative thereof.

In some aspects, the invention provides the system, method or use described therein, wherein the operating conditions are provided such that the combined stability and activity of the SspCA or functional derivative thereof provide enhanced overall $CO_2$ capture over time per given enzyme utilization.

In some aspects, the invention provides the system, method or use described therein, wherein the operating conditions and SspCA are provided such that the SspCA or functional derivative thereof, within its lifetime, transforms at least $4.3 \times 10^7$ mmole·m$^{-2}$·bar$^{-1}$ of $CO_2$.

BRIEF DESCRIPTION OF THE DRAWINGS

FIG. 1 shows an amino acid sequence SEQ ID NO: 2 of SspCA and its nucleic acid encoding sequence SEQ ID NO: 1. The cleaved signal peptide is underscored and may be replaced with a methionine.

FIG. 2 shows sequence similarities between SspCA and the most similar proteins in GenBank, which were located by performing a protein Blast against known sequences in GenBank.

FIG. 7 shows a polynucleotide sequence SEQ ID NO: 7 encoding SspCA without its signal peptide. The ATG codon, encoding methionine, replaced the signal peptide encoding sequence.

FIG. 8 shows a polypeptide sequence SEQ ID NO: 8 corresponding to SspCA without its signal peptide. A methionine replaces the signal peptide.

FIG. 9 shows the polypeptide sequence SEQ ID NO: 197 of M6X Enzyme.

FIG. 10 shows a sequence alignment between SspCA (SEQ ID NO: 8) and M6X enzyme (SEQ ID NO: 197).

DETAILED DESCRIPTION

Various techniques are provided herein for $CO_2$ capture using SspCA for catalysis, leveraging the stability and activity of the SspCA for operating conditions of the $CO_2$ capture process.

Referring to FIG. 1, an amino acid sequence of an SspCA is illustrated. The cleaved signal peptide is underscored and may be replaced with a methionine. Various SspCA variants and functional derivatives may also be used in the $CO_2$ capture techniques described herein. SspCA is a carbonic anhydrase that catalyzes the interconversion of $CO_2$ and water to bicarbonate and hydrogen ions or vice versa. SspCA is obtained or derived from the thermophilic bacteria *Sulfurihydrogenibium* sp. Y03A0P1 (SspCA) (Russo et al. Chemical Engineering Transactions, vol 27, 2012, p. 181-186 ISSN: 1974-9791), which was first isolated in hot springs of Yellowstone park and includes the amino acid sequence as set forth in SEQ ID NO:1 (GenBank under ACD 66216.1), belonging to the alpha class of carbonic anhydrases. Methods for isolating/obtaining an enzyme from bacteria are known, such as immunoprecipitation, ultracentrifugation or chromatographic methods. Further details and definitions related to SspCA may be found in the Definitions section below.

Referring now to FIG. 2, the listed carbonic anhydrase enzymes may also be used in $CO_2$ capture techniques described herein. In particular, the carbonic anhydrases that are derived from thermophilic organisms may be preferably used. In addition, among the thermophiles, those that belong to the Aquificales order, such as *Sulfurihydrogenobium azorense* and *Thermovibrio ammonificans*, may be particularly preferred for certain $CO_2$ capture techniques. The carbonic anhydrases from the *Nitratiruptor* genus, such as *Nitratiruptor* sp SB155-2, may also be preferably used.

Figure 5:
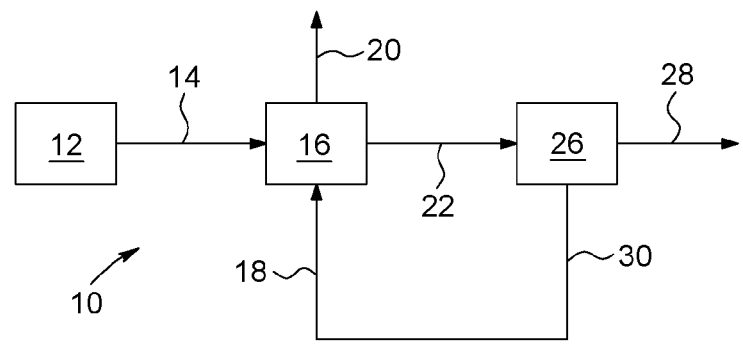
FIG. 5 is a process flow diagram illustrating one embodiment of the present invention, using a $CO_2$ capture system.

Referring now to FIG. 5, an example of the overall $CO_2$ capture system 10 includes a source 12 of $CO_2$ containing gas 14. The source may be a power plant, an aluminum smelter, refinery or another type of $CO_2$ producing operation at high or atmospheric pressure, or may also be ambient air for some specific applications such as air fractionation or air cleaning. The $CO_2$ containing gas 14 is supplied to an absorption unit 16, which is also fed with an aqueous absorption solution 18 for contacting the $CO_2$ containing gas 14. In some implementations, the aqueous absorption solution 18 includes carbonic anhydrase including SspCA or a functional derivative thereof and an absorption compound. The carbonic anhydrase may be free in the aqueous absorption solution 18 as dissolved enzyme or aggregates or particles of enzymes. The carbonic anhydrase may be on or in particles that are present in the aqueous absorption solution 18 and flow with it through the absorption unit 16. The carbonic anhydrase may be immobilized with respect to the particles using any method while keeping at least some of its activity. Some immobilization techniques include covalent bonding, entrapment, and so on. The carbonic anhydrase may be immobilized with respect to supports, which may be various structures such as packing material, within the absorption unit 16 so as to remain within the absorption unit 16 as the aqueous absorption solution 18 flows through it.

The $CO_2$ containing gas 14 may be a $CO_2$-containing effluent from various sources that includes a proportion of $CO_2$ and other gases. For example the gas may include from about 0.03% to 60% (v/v) of $CO_2$ although the $CO_2$ concentration may be greater. The $CO_2$-containing gas may also be a gas having high $CO_2$ content up to 100%, which may be useful for the production of compounds such as sodium bicarbonate from $CO_2$ gas as one of the starting materials.

The absorption unit 16 may be of various types, such as a packed reactor, a spray reactor, a bubble column type reactor, and so on. There may be one or more reactors that may be provided in series or in parallel. In the absorption unit 16, the SspCA catalyses the hydration reaction of $CO_2$ into bicarbonate and hydrogen ions and thus a $CO_2$ depleted gas 20 and an ion rich solution 22 are produced.

The ion rich solution 22 is then supplied to a desorption unit 26 to produce a $CO_2$ stream 28 and an ion depleted solution 30. SspCA may also be present to catalyse the dehydration reaction of bicarbonate ions into $CO_2$ and thus a $CO_2$ depleted gas 20 and an ion lean solution 22 is produced. Alternatively, the ion rich solution 22 may be supplied to another type of regeneration step such as mineral carbonation and the like.

Figure 6:
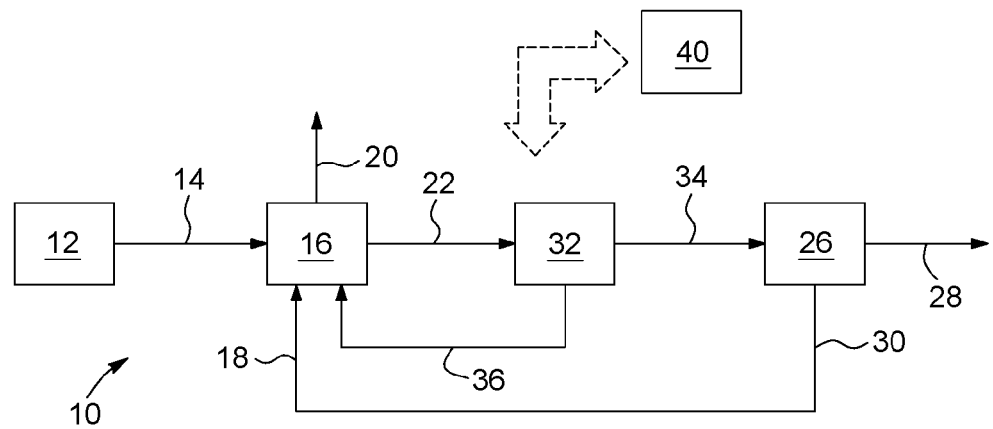
FIG. 6 is another process flow diagram illustrating one embodiment of the present invention, using a $CO_2$ capture system including a separation unit.

Referring now to FIG. 6, the system 10 may also include a separation unit 32 arranged in between the absorption unit 16 and the desorption unit 26, for removing at least some and possibly all of the SspCA in the event the enzyme is flowing with the ion rich solution 22, e.g. when the enzyme is free in solution or immobilized with respect to particles. The separation unit 32 produces an enzyme depleted stream 34 that may be supplied to the desorption unit 26 and an enzyme rich stream 36 that may be recycled, in whole or in part, to the absorption unit 16. The separation unit may also include one or more separators in series or parallel. The separators may be filters or other types of separators, depending on the removal characteristics for the enzymes and the form of the enzymes or particles.

The system may also include various other treatment units for preparing the ion rich solution for the desorption unit and/or for preparing the ion deplete unit for recycling into the absorption unit. There may be pH adjustment units or various monitoring units.

In some implementations, at least some SspCA is provided in the desorption unit. The SspCA may be provided within the input ion rich solution or added separately. The SspCA may be tailored, designed, immobilised or otherwise delivered in order to withstand the conditions in the desorption unit. SspCA may catalyze the conversion of bicarbonate ion to $CO_2$ as described in Reaction 1 (reverse reaction).

Referring still to FIG. 6, the system may also include a measurement device 40 for monitoring properties of various streams and adjusting operation of the absorption unit 16 to achieve desired properties. Adjusting could be done by various methods including modifying the liquid and/or gas flow rates, for example, or adjusting other operating conditions.

In some implementations, the absorption unit may be operated at conditions so as to leverage the activity and/or stability of the SspCA used to catalyze the $CO_2$ hydration reaction. For example, it has been found that SspCA can present high residual activity over a range of elevated temperatures in aqueous absorption solution including sodium carbonate or potassium carbonate. SspCA also presents high activity at lower ambient temperature to provide elevated $CO_2$ flux in aqueous absorption solutions including sodium carbonate, potassium carbonate or MDEA. The operating conditions may include an operating temperature and at least one operating absorption compound within the absorption solution. The operating conditions may further include pH, $CO_2$ loading, gas and liquid flow rates and compositions, and so on.

In some implementations, the operating conditions are coordinated for maximum leverage of the SspCA functionality in $CO_2$ capture.

In some implementations, the operating conditions may include temperature conditions that, depending on various other parameters of the $CO_2$ capture operation, may provide an absorption temperature higher than 10° C. and lower than 98° C., such as 15° C., 20° C., 25° C., 30° C., 35° C., 40° C., 45° C., 50° C., 55° C., 60° C., 65° C., 70° C., 75° C., 80° C., 85° C., 90° C., 95° C., 98° C., or any temperature in between. It should also be understood that the temperature conditions in the absorption unit may vary within a certain temperature range, since the operating temperatures at different locations within the absorption unit will be different. In addition, the temperature of the absorption solution can substantially fluctuate throughout absorption and desorption stages that can be used in some $CO_2$ capture operations.

In some implementations, the operating conditions may include temperature conditions that, depending on various other parameters of the $CO_2$ capture operation, may provide a desorption temperature higher than 10° C. and lower than 110° C., such as 15° C., 20° C., 25° C., 30° C., 35° C., 40° C., 45° C., 50° C., 55° C., 60° C., 65° C., 70° C., 75° C., 80°

C., 85° C., 90° C., 95° C., 100° C., 105° C., 110° C. or any temperature in between. It should also be understood that the temperature conditions in the desorption unit may vary within a certain temperature range, since the operating temperatures at different locations within the desorption unit will be different. In addition, the temperature of the absorption solution can substantially fluctuate throughout absorption and desorption stages that can be used in some $CO_2$ capture operations.

In some implementations, the operating conditions may include an aqueous absorption solution including an absorption compound, which will be further discussed below.

The enzyme is preferably used in combination with an absorption solution that will supply the $CO_2$ carrying capacity for the process. The solution may have a composition allowing acceleration of the enzyme catalytic rate by capturing the hydrogen ion released during the hydration reaction. Using SspCA allows the $CO_2$ capture operation to be accelerated, reducing the size of the required capture vessels and associated capital costs. In addition, by taking advantage of this accelerative mechanism, energetically favorable absorption compounds such as tertiary and hindered amines, carbonate/bicarbonate solutions and amino acids/amino acid salts can be employed to reduce associated process energy consumption, where these absorption compounds would normally be too slow to be used efficiently without enzymatic catalysis.

The aqueous absorption solution may include at least one absorption compound that aids in the absorption of $CO_2$. The absorption compound may include potassium carbonate, sodium carbonate, ammonium carbonate, at least one amine, which may be a primary amine, a secondary amine, a tertiary amine, a primary alkanolamine, a secondary alkanolamine, a tertiary alkanolamine, and/or an amino acid with primary, secondary or tertiary amino group(s) or a combination thereof. Combinations of absorption compounds include a carbonate and at least one of the amines and/or amino acids mentioned therein or herein, to produce a promoted carbonate absorption solution.

In some scenarios, the absorption compound may be monoethanolamine (MEA), 2-amino-2-methyl-1-propanol (AMP), 2-(2-aminoethylamino)ethanol (AEE), 2-amino-2-hydroxymethyl-1,3-propanediol (Tris or AHPD), N-methyldiethanolamine (MDEA), dimethylmonoethanolamine (DMMEA), diethylmonoethanolamine (DEMEA), triisopropanolamine (TIPA), triethanolamine (TEA), DEA, DIPA, MMEA, TIA, TBEE, HEP, AHPD, hindered diamine (HDA), bis-(tertiarybutylaminoethoxy)-ethane (BTEE), ethoxyethoxyethanol-tertiarybutylamine (EEETB), bis-(tertiarybutylaminoethyl)ether, 1,2-bis-(tertiarybutylaminoethoxy)ethane and/or bis-(2-isopropylaminopropyl)ether, and the like.

In some scenarios, the absorption compound may be piperidine, piperazine, derivatives of piperidine, piperazine which are substituted by at least one alkanol group, dialkylether of polyalkylene glycols, dialkylether or dimethylether of polyethylene glycol, amino acids comprising glycine, proline, arginine, histidine, lysine, aspartic acid, glutamic acid, methionine, serine, threonine, glutamine, cysteine, asparagine, valine, leucine, isoleucine, alanine, tyrosine, tryptophan, phenylalanine, and derivatives such as taurine, N,cyclohexyl 1,3-propanediamine, N-secondary butyl glycine, N-methyl N-secondary butyl glycine, diethylglycine, dimethylglycine, sarcosine, methyl taurine, methyl-$\alpha$-aminopropionicacid, N-($\beta$-ethoxy)taurine, N-($\beta$-aminoethyl)taurine, N-methyl alanine, 6-aminohexanoic acid, potassium or sodium salt of the amino acid or a combination thereof.

The absorption compound used to make up the aqueous absorption solution may be at least one of the example compounds, i.e. potassium carbonate, sodium carbonate and/or MDEA. In some scenarios, the concentration of the absorption compound in the solution may be between about 0.1 M and about 10 M, depending on various factors. When the absorption compound is amine-based, the concentration of the amine-based solution may be between about 0.1M and 8M and when the absorption compound is amino acid-based, the concentration of the amino acid-based solution may be between about 0.1M and 6M.

The pH of the absorption solution may be between about 8 and about 12, depending for example on the absorption compound and on the $CO_2$ loading of the solution.

The SspCA may be dissolved in the absorption solution. The concentration of the SspCA or functional derivative thereof may be between about 0.1 and about 50 g/L, between about 0.1 and about 10 g/L or between about 0.1 and about 5 g/L. When the SspCA is not dissolved in the solution but is rather immobilized on mobile particles or fixed packing material, the amount of immobilized SspCA may be similar so as to provide a similar activity as the therein mentioned concentrations of dissolved SspCA.

As noted above, the SspCA or functional derivative thereof may be provided free or dissolved in the solvent, immobilized or entrapped or otherwise attached to particles that are in the absorption solution or to packing material or other structures that are fixed within the reaction chamber.

In the case where the SspCA or functional derivative thereof is immobilized with respect to a support material, this may be accomplished by an immobilization technique selected from adsorption, covalent bonding, entrapment, copolymerization, cross-linking, and encapsulation, or combination thereof.

In one scenario, the SspCA or functional derivative thereof may be immobilized on a support that is in the form of particles, beads or packing. Such supports may be solid or porous with or without coating(s) on their surface. The SspCA or functional derivative thereof may be covalently attached to the support and/or the coating of the support, or entrapped inside the support or the coating. The coating may be a porous material that entraps the SspCA or functional derivative thereof within pores and/or immobilizes the SspCA by covalent bonding to the surfaces of the support. The support material may be made from a compound different than the SspCA or functional derivative thereof. The support material may include nylon, cellulose, silica, silica gel, chitosan, polyacrylamide, polyurethane, alginate, polystyrene, polymethylmetacrylate, magnetic material, sepharose, titanium dioxide, zirconium dioxide and/or alumina, respective derivatives thereof, and/or other materials. The support material may have a density between about 0.6 g/ml and about 5 g/ml such as a density above 1 g/ml, a density above 2 g/mL, a density above 3 g/mL or a density of about 4 g/m L.

In some scenarios, the SspCA or functional derivative thereof may be provided as cross-linked enzyme aggregates (CLEAs) and/or as cross-linked enzyme crystals (CLECs).

In the case of using enzymatic SspCA particles, including CLEAs or CLECs, the particles may be sized to have a diameter at or below about 17 μm, optionally about 10 μm, about 5 μm, about 4 μm, about 3 μm, about 2 μm, about 1 μm, about 0.9 μm, about 0.8 μm, about 0.7 μm, about 0.6 μm, about 0.5 μm, about 0.4 μm, about 0.3 μm, about 0.2 μm, about 0.1 μm, about 0.05 μm, or about 0.025 μm. The particles may also have a distribution of different sizes.

The SspCA used in connection with the techniques described herein may be an isolated and/or substantially pure form.

There is also provided a carbonic anhydrase polypeptide or functional derivatives thereof, which is stable and active at a broad range of temperatures.

In one aspect, the invention provides a carbonic anhydrase polypeptide comprising the sequence as set forth in SEQ ID NO: 2 or functional derivative thereof, an expression or cloning vector comprising a nucleotide sequence encoding such carbonic anhydrase, and a transgenic cell comprising such expression or cloning vector.

The SspCA or the derivative thereof can be used in various processes and scenarios such as those described in the following patent references that are hereby incorporated herein by reference: CA 2.291.785; CA 2.329.113, CA 2.393.016, CA 2,443,222, U.S. Pat. No. 6,908,507; EU 1 377 531, U.S. Pat. No. 7,514,056, U.S. Pat. No. 7,596,952; U.S. Pat. No. 8,066,965, U.S. Pat. No. 8,277,769, U.S. Pat. No. 6,946,288, U.S. Pat. No. 7,740,689, PCT/CA2012/050063, U.S. Ser. No. 13/503,808, U.S. Ser. No. 12/984,852, U.S. Ser. No. 13/388,854, U.S. Ser. No. 13/264,294, U.S. Ser. No. 13/388,871, U.S. Ser. No. 13/508,246, U.S. Ser. No. 11/460,402.

Definitions

In order to further appreciate some of the terms used herein, the following definitions and discussion are provided.

The expression "polypeptide" refers to any peptide or protein comprising two or more amino acids joined to each other by peptide bonds or modified peptide bonds. "Polypeptide(s)" refers to both short chains, commonly referred to as peptides, oligopeptides and oligomers, and to longer chains generally referred to as proteins. Polypeptides may contain amino acids other than the 20 gene-encoded amino acids, optionally polypeptides may contain glycine, proline, arginine, histidine, lysine, aspartic acid, glutamic acid, methionine, serine, threonine, glutamine, cysteine, asparagine, valine, leucine, isoleucine, alanine, tyrosine, tryptophan, phenylalanine, selenocysteine, selenomethionine, pyrrolysine. "Polypeptide(s)" include those modified either by natural processes, such as processing and other post-translational modifications, but also by chemical modification techniques. Such modifications are well described in basic texts and in more detailed monographs, as well as in a voluminous research literature and they are well known to those of skill in the art. It will be appreciated that the same type of modification may be present in the same or varying degree at several sites in a given polypeptide.

The expression "functional derivative" refers to a protein/peptide/polypeptide sequence that possesses a functional biological activity that is substantially similar to the biological activity of the original protein/peptide/polypeptide sequence. In other words, it refers to a polypeptide of the carbonic anhydrase as defined herein that substantially retain(s) the capacity of catalyzing the hydration of carbon dioxide. A functional derivative of the carbonic anhydrase protein/peptide as defined herein may or may not contain post-translational modifications such as covalently linked carbohydrates, if such modifications are not necessary for the performance of a specific function. The "functional derivative" may also comprise nucleic acid sequence variants. These variants may result from the degeneracy of the genetic code or from a mutation, substitution, addition or deletion. Further, the carbonic anhydrase as defined herein may comprise a Tag such as a histidine Tag. The term "functional derivative" is meant to encompass the "variants", the "mutants", the "fragments" or the "chemical derivatives" of a carbonic anhydrase protein/peptide. Methods for measuring carbonic anhydrase activity are known such as stirred cell reactor assay or the method described by Chirica et al. (Chirica et al. European Journal of Biochemistry, 1997, 244, 755-60). These functional derivatives have at least 60%, 65%, 70%, 75%, 80%, 85%, 86%, 87%, 88%, 89%, 90%, 91%, 92%, 93%, 94%, 95%, 96%, 97%, 98% 99% or 99.5% identity with the sequence as set forth in SEQ ID NO: 8, optionally over the entire length of the sequence or on a partial alignment of the sequences.

The term "polynucleotide fragment", as used herein, refers to a polynucleotide whose sequence (e.g., cDNA) is an isolated portion of the subject nucleic acid constructed artificially (e.g., by chemical synthesis) or by cleaving a natural product into multiple pieces, using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art.

The term "polypeptide or fragments thereof" as used herein refers to peptides, oligopeptides and proteins. This term also does not exclude post-expression modification of polypeptides. For example, polypeptides that include the covalent attachment of glycosyl groups, acetyl groups, lipid groups and the like are encompassed by the term polypeptide.

Techniques for determining nucleic acid and amino acid "sequence identity" are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). Another method of establishing percent identity which can be used in the context of the present invention is the MPSRCH package of programs copyrighted by the University of Edinburgh, developed by John F. Collins and Shane S. Sturrok, and distributed by IntelliGenetics, Inc. (Mountain View, Calif.).

From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix BLOSUM62; Descriptions=50 sequences; sort by=HIGH SCORE; Databases=non-redundant, GenBank+EMBL+DDBJ+PDB+GenBank CDS translations+Swiss protein+Spupdate+PIR.

By "substantially identical" when referring to a polypeptide, it will be understood that the polypeptide of the present invention preferably has an amino acid sequence having at least about 60%, 65%, 70%, 75%, 80%, 81%, 82%, 83%, 84% 85%, 86%, 87%, 88%, 89%, 90%, 91%, 92%, 93%, 94%, 95%, 96%, 97%, 98%, 99%, 99.5% or any other value in between to SEQ ID NO: 2 or SEQ ID NO: 8, or functional derivatives thereof, optionally over the entire length of the peptide.

One can use a program such as the CLUSTAL program to compare amino acid sequences. This program compares amino acid sequences and finds the optimal alignment by inserting spaces in either sequence as appropriate. It is possible to calculate amino acid identity or homology for an optimal alignment. A program like BLASTp will align the longest stretch of similar sequences and assign a value to the fit. It is thus possible to obtain a comparison where several regions of similarity are found, each having a different score. Both types of identity analysis are contemplated for the present invention.

With respect to protein or polypeptide, the term "isolated polypeptide" or "isolated and purified polypeptide" is sometimes used herein. This term refers primarily to a protein produced by expression of an isolated and modified polynucleotide molecule contemplated by the invention. Alternatively, this term may refer to a protein which has been sufficiently separated from other proteins with which it would naturally be associated, so as to exist in "substantially pure" form.

The term "substantially pure" refers to a preparation comprising at least 50% by weight of the carbonic anhydrase polypeptide or derivative thereof on total protein content. More preferably, the preparation comprises at least 75% by weight, and most preferably 90-99% by weight, of the carbonic anhydrase polypeptide or derivative thereof.

Purity is measured by methods appropriate for the carbonic anhydrase polypeptide or derivative thereof as described herein (e.g. chromatographic methods, agarose or polyacrylamide gel electrophoresis, HPLC analysis, and the like).

The SspCA polypeptide or functional derivative thereof may also comprise amino acids substitution such that the carbonic anhydrase or functional derivative thereof retains catalytic activity (i.e. the interconversion of $CO_2$ with $HCO_3^-$ and $H^+$). The term "substituted amino acid" is intended to include natural amino acids and non-natural amino acids. Non-natural amino acids include amino acid derivatives, analogues and mimetics. As used herein, a "derivative" of an amino acid refers to a form of the amino acid in which one or more reactive groups on the compound have been derivatized with a substituent group. As used herein an "analogue" of an amino acid refers to a compound that retains chemical structures of the amino acid necessary for functional activity of the amino acid yet also contains certain chemical structures that differ from the amino acid. As used herein, a "mimetic" of an amino acid refers to a compound in that mimics the chemical conformation of the amino acid.

As used herein, the term "polynucleotide(s)" generally refers to any polyribonucleotide or poly-deoxyribonucleotide, which may be unmodified RNA or DNA or modified RNA or DNA. This definition includes, without limitation, single- and double-stranded DNA, DNA that is a mixture of single- and double-stranded regions or single-, double- and triple-stranded regions, cDNA, single- and double-stranded RNA, and RNA that is a mixture of single- and double-stranded regions, hybrid molecules comprising DNA and RNA that may be single-stranded or, more typically, double-stranded, or triple-stranded regions, or a mixture of single- and double-stranded regions. The term "polynucleotide(s)" also embraces short nucleotides or fragments, often referred to as "oligonucleotides", that due to mutagenesis are not 100% identical but nevertheless code for the same amino acid sequence.

By "substantially identical" when referring to a polynucleotide, it will be understood that the polynucleotide of the invention has a nucleic acid sequence which encodes a polypeptide which is at least about 60%, 65%, 70%, 75%, 80%, 81%, 82%, 83%, 84% 85%, 86%, 87%, 88%, 89%, 90%, 91%, 92%, 93%, 94%, 95%, 96%, 97%, 98%, 99%, 99.5% or any other value between 60 and 99.5% identical to SEQ ID NO 1 or SEQ ID NO: 8 or functional derivative thereof.

By "substantially identical" when referring to a polynucleotide, it will be understood that the polynucleotide of the invention has a nucleic acid sequence which is at least about 60%, 65%, 70%, 75%, 80%, 81%, 82%, 83%, 84% 85%, 86%, 87%, 88%, 89%, 90%, 91%, 92%, 93%, 94%, 95%, 96%, 97%, 98%, 99%, 99.5% or any other value between 60 and 99.5% identical to SEQ ID NO 7 or functional derivative thereof.

With reference to polynucleotides of the invention, the term "isolated polynucleotide" is sometimes used. This term, when applied to DNA, refers to a DNA molecule that is separated from sequences with which it is immediately contiguous to (in the 5' and 3' directions) in the naturally occurring genome of the organism from which it was derived. For example, the "isolated polynucleotide" may comprise a DNA molecule inserted into a vector, such as a plasmid or virus vector, or integrated into the genomic DNA of a procaryote or eucaryote. An "isolated polynucleotide molecule" may also comprise a cDNA molecule.

As used herein, the term "vector" refers to a polynucleotide construct designed for transduction/transfection of one or more cell types. Vectors may be, for example, cloning vectors which are designed for isolation, propagation and replication of inserted nucleotides, expression vectors which are designed for transcription of a nucleotide sequence in a host cell, or a viral vector which is designed to result in the production of a recombinant virus or virus-like particle, or shuttle vectors, which comprise the attributes of more than one type of vector. A number of vectors suitable for stable transfection of cells and bacteria are available to the public (e.g. plasmids, adenoviruses, baculoviruses, yeast baculoviruses, plant viruses, adeno-associated viruses, retroviruses, Herpes Simplex Viruses, Alphaviruses, Lentiviruses), as are methods for constructing such cell lines. It will be understood that the present invention encompasses any type of vector comprising any of the polynucleotide molecules of the invention.

The term "transgenic cell" refers to a genetically engineered cell. Methods for genetically engineering a cell are known such as molecular cloning and gene targeting. These methods can include chemical-based transfection, non chemical method, particle-based method or viral method. The host cell may be any type of cell such as a transiently-transfected or stably-transfected mammalian cell line, an isolated primary cell, an insect cell, a yeast (Saccharomyces cerevisiae or Pichia pastoris), a plant cell, a microorganism, or a bacterium (such as E. coli).

The expressions "naturally occurring" or "wild-type" refer to material in the form as it occurs in nature. For example, a naturally occurring or wild-type polypeptide or polynucleotide sequence is a sequence present in an organism that is isolated from a source in nature and which has not been intentionally modified by human manipulation. The expressions "Recombinant", "engineered" or "non-naturally occurring": it do not appears in nature, it is an artificial construct. e.g., a cell, nucleic acid, or polypeptide, refers to a material that either has been modified in a manner that would not otherwise be found in nature, or is identical thereto but produced or derived from synthetic materials and/or by manipulation using recombinant techniques.

The expression "Reference sequence" refers to a defined sequence to which another sequence is compared. In one aspect of the invention, the reference sequence is SEQ ID NO: 2 and preferably SEQ ID NO: 8.

The expression "Coding sequence" refers to the nucleic acid sequence(s) that would yield the amino acid sequence of a given protein.

The expressions "Amino acid", "Residue", "Amino acid residue" refer to the specific monomer at a sequence position of a polypeptide (e.g., G82 indicates that the "amino acid" or "residue" at position 82 of SEQ ID NO: XX is a glycine (G). The amino acid may be alanine (3 letter code: ala or one letter code: A), arginine (arg or R), asparagine (asn or N), aspartic acid (asp or D), cysteine (cys or C), glutamine (gln or Q), glutamic acid (glu or E), glycine (gly or G), histidine (his or H), Isoleucine (ile or I), leucine (leu or L), lysine (lys or K), methionine (met or M), phenylalanine (phe or F), proline (pro or P), serine (ser or S), threonine (thr or T), tryptophan (trp or W), tyrosine (tyr or Y), valine (vat or V)

The expression "Amino acid difference" refers to an amino acid at a given position in a protein sequence that is different from the one in the reference sequence. It refers to a change in the amino acid residue at a position of a polypeptide sequence relative to the amino acid residue at a corresponding position in a reference sequence. The positions of amino acid differences generally are referred to herein as "Xn," where n refers to the corresponding position in the reference sequence upon which the residue difference is based. For example, a "residue difference at position X82 as compared to SEQ ID NO: 8" refers to a change of the amino acid residue at the polypeptide position corresponding to position 82 of SEQ ID NO: 8. Thus, if the reference polypeptide of SEQ ID NO: 8 has a glycine at position 82, then a "residue difference at position X82 as compared to SEQ ID NO: 8" an amino acid substitution of any residue other than glycine at the position of the polypeptide corresponding to position 82 of SEQ ID NO: 8. In most instances herein, the specific amino acid residue difference at a position is indicated as "XnY" where "Xn" specifies the corresponding position as described therein, and "Y" is the single letter identifier of the amino acid found in the engineered polypeptide (i.e., the different residue than in the reference polypeptide). In some instances, the present disclosure also provides specific amino acid differences denoted by the conventional notation "AnB", where A is the single letter identifier of the residue in the reference sequence, "n" is the number of the residue position in the reference sequence, and B is the single letter identifier of the residue substitution in the sequence of the engineered polypeptide. For example, "G82C" would refer to the substitution of the amino acid residue, glycine (G) at position 82 of reference sequence with the amino acid cystein (C). In some instances, a polypeptide of the present disclosure can include one or more amino acid residue differences relative to a reference sequence, which is indicated by a list of the specified positions where changes are made relative to the reference sequence. The present disclosure includes engineered polypeptide sequences comprising one or more amino acid differences that include either/or both conservative and non-conservative amino acid substitutions.

The term "Conservative amino acid substitution" refers to an amino acid at a given position in a protein sequence, that is different but similar from the one in the reference sequence. The similarity can be evaluated by using the scoring matrix developed by Dayhoff, Atlas of Protein Sequences and Structure, M. O. Dayhoff ed., 5 suppl. 3:353-358, National Biomedical Research Foundation, Washington, D.C., USA.

The term "Non-conservative substitution refers to an amino acid, at a given position in a protein sequence that is different and not similar from the one in the reference sequence.

The term "Deletion" refers to one or several amino acid(s) at a given position in a protein sequence, that is or are absent when compared to the reference sequence.

The term "Insertion" refers to one or several amino acid(s) at a given position in a protein sequence, that is or are in excess when compared to the reference sequence.

The term "Improved enzyme property" refers to a property that is better in one enzyme when compared to the reference one. It can be an increase in stability toward some denaturing agent, an increase in thermostability, an increase in solvent stability, an increase in pH stability, an increase in enzyme activity, reduced inhibition by products (eg. bicarbonate and/or carbonate ions), improved stability in presence of the sodium cation, improved stability in presence of the potassium cation, improved solvent solubility, or a combination thereof.

The term "Stability in presence of" refers to the capacity of the enzyme to remain active over a period of time when in the presence of a denaturing compound. It is usually described as a percentage of remaining activity over time.

The term "Thermostability" refers to the capacity of the enzyme to remain active over a period of time when exposed to a given temperature. It is usually described as a percentage of remaining activity over time.

The term "Solvent stability" refers to the capacity of the enzyme to remain active over a period of time when exposed to a given solvent. It is usually described as a percentage of remaining activity over time.

The term "pH stability" refers to the capacity of the enzyme to remain active over a period of time when exposed to a given pH, such as a higher pH. It is usually described as a percentage of remaining activity over time.

The term "Increased enzyme activity" refers to the capacity of an enzyme to catalyze more reaction, such as hydration of $CO_2$ and/or dehydration of the $HCO_3^-$ ion, per time unit than the reference enzyme in some given conditions, such as higher Temperature, higher pH (improved pH activity profile).

By "about", it is meant that the relevant value (e.g. of temperature, concentration, pH, etc.) can vary within a certain range depending on the margin of error of the method or apparatus used to evaluate such value. For instance, the margin of error of the temperature may range between ±0.5° C. to ±1° C., the margin of error of the pH may be ±0.1 and the margin of error of the concentration may be ±20%.

Various aspects of the present invention will be more readily understood by referring to the following examples. These examples are illustrative of the wide range of applicability of the present invention and are not intended to limit its scope. Modifications and variations can be made therein without departing from the spirit and scope of the invention. Although any methods and materials similar or equivalent to those described herein can be used in the practice for testing of the present invention, the preferred methods and materials are described.

The scope of the claims should not be limited by the aspects, scenarios, implementations, examples or embodiments set forth in the examples and the description, but should be given the broadest interpretation consistent with the description as a whole.

The issued patents, published patent applications, and references that are mentioned herein are hereby incorporated by reference. In the case of inconsistencies, the present disclosure will prevail.

EXAMPLES

Example 1: Materials, Methods and Producing of SspCA Having a Polypeptide Sequence Described in SEQ ID NO: 8

An SspCA enzyme was produced without the signal peptide: the first 20 amino acids were replaced by a single methionine. The first 20 amino acids (signal peptide) are underlined in FIG. 1. The enzyme was purified and characterized in a stirred cell reactor and a micro stirred cell reactor. The resulting coding nucleotide sequence is shown in FIG. 7 and the encoded SspCA amino acid sequence is shown at FIG. 8. Amino acid residue numbering will follow that of FIG. 8.

The stirred cell reactor (SCR) assay was similar to the one described in Penders N. J. M. C. et al. entitled *Kinetics of absorption of carbon dioxide in aqueous MDEA solutions with carbonic anhydrase at 298K* (International Journal of Greenhouse Gas Control, (2012) 9:385-392). In brief, the pressure drop in the gas phase over the absorbing solution is monitored. This $CO_2$ pressure drop over time is translated into $CO_2$ absorption flux.

The micro stirred cell assays were performed using 2 ml cells in the appropriate solvent under 1 atmosphere of 100% $CO_2$ at 22° C. The pH changes were monitored using a pH indicator present in the solution and a spectrophotometer. The pH could then be correlated to an absorbed $CO_2$ concentration using a standard curve of optical density versus $CO_2$ loading and then a $CO_2$ absorption flux is obtained.

Comparative tests were performed to compare the stability and activity of SspCA with other carbonic anhydrases. SspCA was compared with the following other carbonic anhydrases:

(i) A thermostable variant of the human carbonic anhydrase type II (HCAII) referred to as "M6X", described in U.S. Pat. No. 7,521,217 and developed by $CO_2$ Solutions Inc. having about 34.2% identity with SEQ ID NO: 8. From scientific literature, HCAII is known as one of the fastest enzymes with a $k_{cat}/K_m$ of about $1 \times 10^8$ (ii) A thermostable enzyme that is a variant of M6X developed by $CO_2$ Solutions Inc. and referred to as "CA_A";

(iii) Two other thermostable beta class carbonic anhydrases referred to as "CAB" and "CA_C" obtained from Codexis Inc. located at 200 Penobscot Drive, Redwood City, Calif.

Example 2: Activity of SspCA and M6X in Various Solvents

The activities of SspCA and various other enzymes were compared. The activity was tested in three different absorption solutions: an aqueous absorption solution including MDEA 2M, an aqueous absorption solution including sodium carbonate ($Na_2CO_3$) 0.3M pH 10 and an aqueous absorption solution including potassium carbonate ($K_2CO_3$) 1.45M pH 10. The tests were performed in a SCR reactor at 25° C. As shown in Table 1 presented below, SspCA has a higher activity (flux) than M6X in all three absorption solutions.

TABLE 1

Activity of SspCA and other carbonic anhydrase enzymes (0.2 g/l) in various absorption solutions

| Enzyme | Solvent | Flux mmole · $min^{-1}$ · $m^{-2}$ · $bar^{-1}$ |
|---|---|---|
| no enzyme | Na Carbonates 0.3M pH = 10 | 65 |
| M6x | Na Carbonates 0.3M pH = 10 | 780 |
| SspCA | Na Carbonates 0.3M pH = 10 | 1420 |
| CA_A | Na Carbonates 0.3M pH = 10 | 945 |
| CA_B | Na Carbonates 0.3M pH = 10 | 1565 |
| CA_C | Na Carbonates 0.3M pH = 10 | 1315 |
| no enzyme | MDEA 2M | 210 |
| M6X | MDEA 2M | 1280 |
| SspCA | MDEA 2M | 1780 |
| CA_A | MDEA 2M | 1090 |
| CA_B | MDEA 2M | 2210 |
| CA_C | MDEA 2M | 1540 |
| no enzyme | $K_2CO_3$ 1.45M pH 10 | 77 |
| M6X | $K_2CO_3$ 1.45M pH 10 | 900 |
| SspCA | $K_2CO_3$ 1.45M pH 10 | 918 |
| CA_A | $K_2CO_3$ 1.45M pH 10 | Not available |
| CA_B | $K_2CO_3$ 1.45M pH 10 | 3830 |
| CA_C | $K_2CO_3$ 1.45M pH 10 | Not available |

From these results, SspCA presents approximately 8.5 to 22 times greater activity compared to no enzyme depending on the absorption compound and conditions that were used. SspCA also presents the same or up to 2 times greater activity compared to the M6X carbonic anhydrase depending on the absorption compound and conditions that were used. From the above tests, SspCA is faster than CA_C and slower than CA_B.

Example 3: Stability of SspCA and M6X in Carbonate Buffer

The stabilities of SspCA and M6X were also compared. The stability was evaluated by exposing the enzymes to an absorption solution including sodium carbonate 0.3M at pH 10, potassium carbonate 1.45M pH 10 and/or potassium carbonate 1.45M pH 10, at 60° C. The tests were performed in a SCR reactor at 25° C. and under 100% $CO_2$ conditions. As shown in Table 2 presented below, SspCA was more stable than M6X. In sodium carbonate, M6X was inactivated after one day whereas SspCA still had about 86% of the initial activity after six days of exposure and 65% after 14 days. The half life of those enzymes could be estimated at <1 day for M6X, 1.7 days for CA_B and 22 days for SspCA. The trend is the same in potassium carbonate.

TABLE 2

Stability of SspCA and M6X (0.2 g/l) in sodium or potassium carbonate at 60° C. (activity measured at 25° C.)

| Enzyme | Days | Solvent | $Flux_c$ mmole · $min^{-1}$ · $m^{-2}$ · $bar^{-1}$ |
|---|---|---|---|
| M6X | 0 | Na Carbonate 0.3M pH = 10 | 720 |
| M6X | 1 | Na Carbonate 0.3M pH = 10 | 0 |
| M6X | 0 | K Carbonate 1.45M pH = 10 | 1100 |
| M6X | 1 | K Carbonate 1.45M pH = 10 | 0 |
| M6X | 0 | K Carbonate 1.45M pH = 12 | 1520 |
| M6X | 1 | K Carbonate 1.45M pH = 12 | 27 |
| SspCA | 0 | Na Carbonate 0.3M pH = 10 | 1360 |
| SspCA | 1 | Na Carbonate 0.3M pH = 10 | 1530 |
| SspCA | 6 | Na Carbonate 0.3M pH = 10 | 1170 |
| SspCA | 14 | Na Carbonate 0.3M pH = 10 | 890 |
| SspCA | 0 | K Carbonate 1.45M pH = 10 | 918 |
| SspCA | 1 | K Carbonate 1.45M pH = 10 | 593 |
| SspCA | 3 | K Carbonate 1.45M pH = 10 | 609 |
| SspCA | 7 | K Carbonate 1.45M pH = 10 | 498 |
| SspCA | 0 | K Carbonate 1.45M pH = 12 | 970 |
| SspCA | 1 | K Carbonate 1.45M pH = 12 | 665 |
| CA_B | 0 | Na Carbonate 0.3M pH = 10 | 1500 |
| CA_B | 1 | Na Carbonate 0.3M pH = 10 | 840 |
| CA_B | 3 | Na Carbonate 0.3M pH = 10 | 607 |

$Flux_c$ = Flux with enzyme – Flux no enzyme

From these results, SspCA presents not only greater initial activity compared to M6X, but maintains elevated activity over a longer period of time and thus shows greater stability. Furthermore, SspCA presents slightly lower initial activity than CA_B but shows a greater stability.

Figure 3:
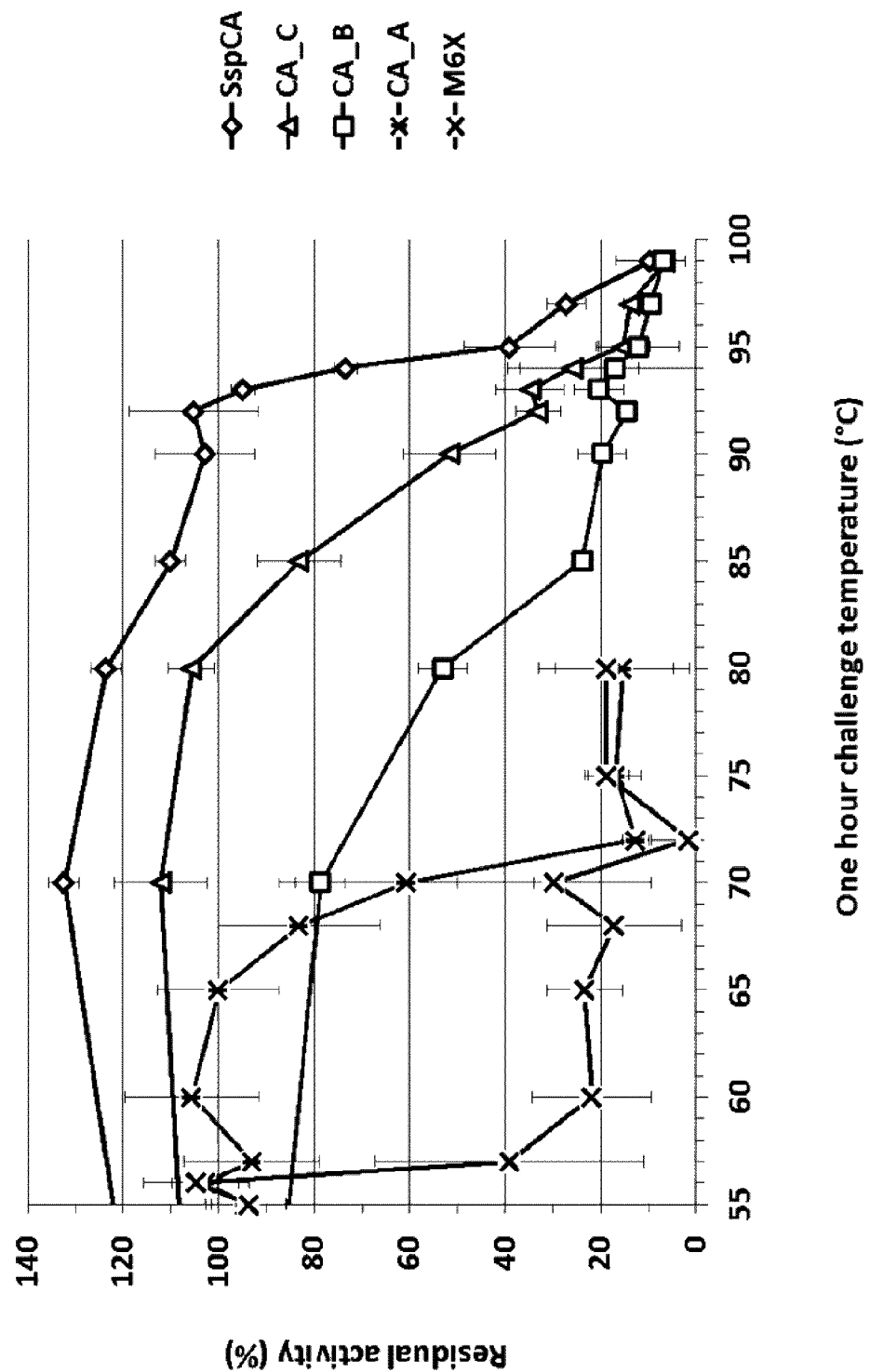
FIG. 3 is a graph of residual activity versus a one hour temperature challenge for various carbonic anhydrases including SspCA in sodium carbonate 0.3M, pH 10, at different temperatures.
Figure 4:
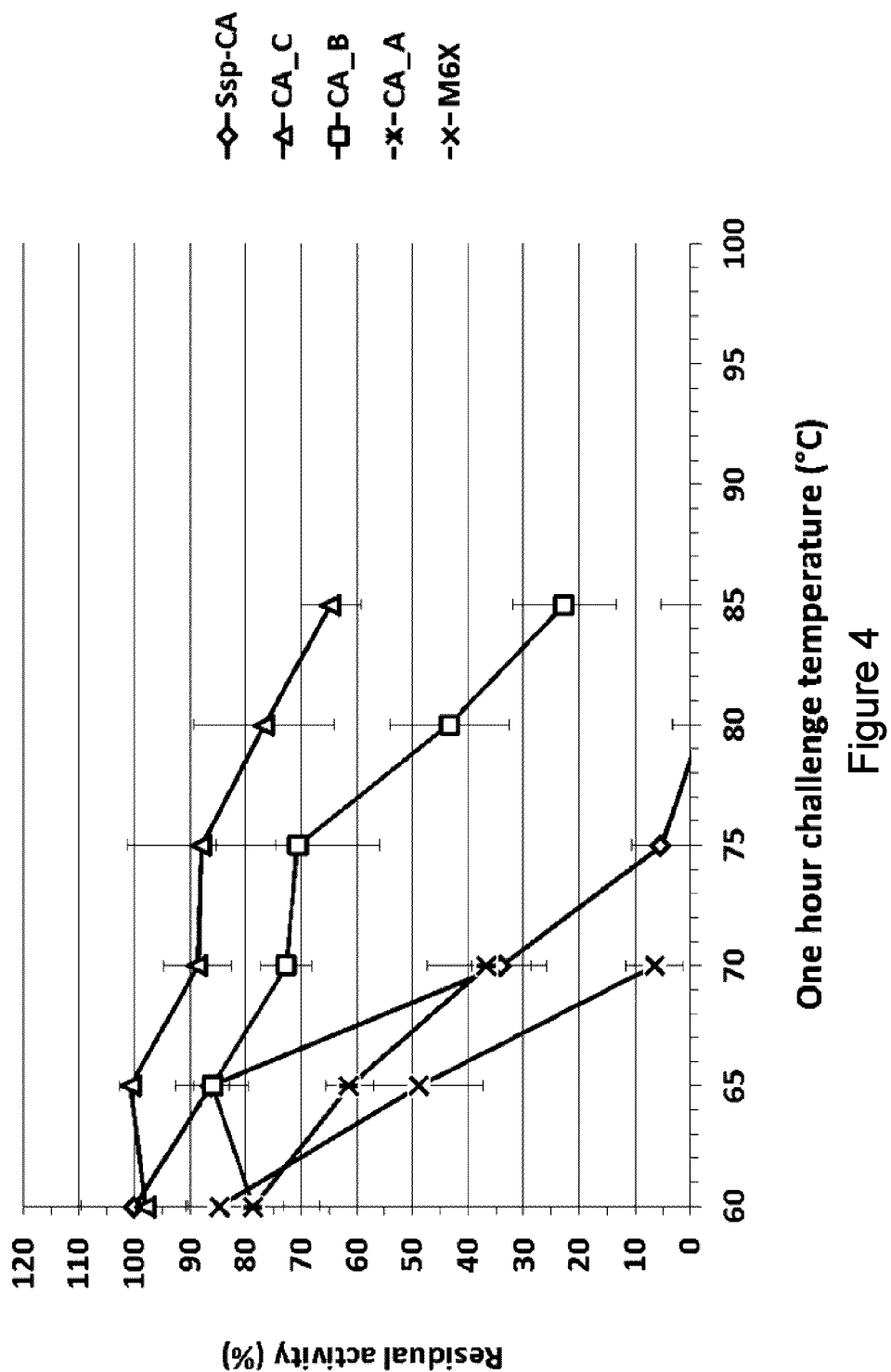
FIG. 4 is a graph of residual activity versus a one hour temperature challenge for various carbonic anhydrases including SspCA in MDEA 4.2M, at pH 11.3, at different temperatures.

Example 4: Residual Activities of SspCA, M6X, CA_a, CA_B and CA_C in Sodium Carbonate or MDEA Solutions The short term stability of M6X, CA_A, CA_B, CA_B and SspCA was compared in two absorption solutions. The first aqueous absorption solution included sodium carbonate 0.3M at pH 10 and the results are illustrated in FIG. 3. The second aqueous absorption solution included MDEA 4.2M (pH 11.3) and the results are illustrated in FIG. 4. All enzymes were provided at a concentration of 0.2 g/l. The test included exposing the absorption solutions including the enzymes to different temperatures for one hour and then the residual activity was measured using micro stirred cell at 22° C.

Referring to FIG. 3, the temperature required to reduce the activity of the enzyme to 50% residual activity was 57° C. for M6X, 70° C. for CA_A, 72° C. for CA_B, 90° C. for CA_C and 95° C. for SspCA, in the sodium carbonate solution. The SspCA showed higher residual activity at all tested temperatures over the range of 55° C. to 100° C. The SspCA showed notably higher residual activity around the temperature range of 85° C. to 95° C. compared to the other enzymes.

Referring to FIG. 4, the temperature required to reduce the activity of the enzyme to 50% residual activity was 65° C. for M6X, 69° C. for SspCA, 68° C. for CA_A, 79° C. for CA_B and >85° C. for CA_C, in the MDEA solution. The SspCA is more stable than M6X (variant from human carbonic anhydrase).

Example 5: Comparison of Amino Acid Sequences Between Carbonic Anhydrase Obtained from *Sulfurihydrogenibium* sp. Y03A0P1 and the Most Similar Protein in GenBank As shown at FIG. 2, the most similar carbonic anhydrase from the carbonic anhydrase obtained from *Sulfurihydrogenibium* sp. Y03A0P1 is from *Sulfurihydrogenibium* azorense Az-Ful with 58% identity, and the nearest one outside the *Sulfurihydrogenibium* genus is the one from *Tolumonas auensis* with 50% identity.

Based on data in Tables 1 and 2 and in FIGS. 3 and 4, SspSCA would have an enhanced impact in $CO_2$ capture in sodium and potassium carbonate solutions because of its highest activity and stability. In a typical $CO_2$ capture process using carbonate based solutions, the experimental data support that SspCA will transform many more $CO_2$ molecules than the other enzymes during its lifetime in the process given its high activity level and higher stability at higher temperature. For instance, from Example 2 above, using the same conditions as in that test, we can expect that a solution with SspCA, within its lifetime, will transform $4.3 \times 10^7$ mmole·$m^{-2}$·$bar^{-1}$ while one with CAB will transform $3.7 \times 10^6$ mmole·$m^{-2}$·$bar^{-1}$. This may be obtained by multiplying initial Flux (Flux at day 0) with half-life. This enhanced transformation of $CO_2$ is significant and can allow improved efficiency and economics of $CO_2$ capture operations. Operating conditions may thus be provided in absorption and/or desorption for leveraging the higher combined stability and activity effect of the SspCA to achieve an overall increase in biocatalytic impact.

Example 6: SspCA's Stability Improvement in Carbonate-Based Buffer

Recombinant (or engineered) carbonic anhydrase (CA) polypeptides having improved properties relative to wild-type SspCA (FIG. 8) were generated. The latter CAs are hereafter referred as improved variants or improved mutants. The improved variants were generated using directed evolution techniques that are well known by those skilled in the art.

The improved properties can be one or a combination of: improved thermostability, improved activity (hydration of $CO_2$ and/or dehydration of the $HCO_3^-$ ion), improved high pH stability (eg. pH 7 to 12), improved pH activity profile, reduced inhibition by products (eg. bicarbonate and/or carbonate ions), improved stability in presence of the sodium cation, improved stability in presence of the potassium cation, improved solvent solubility, or a combination thereof.

The improved variants comprise at least one or more amino acid substitutions in their amino acid sequence relative to that of wild-type SspCA (Seq ID No: 8) that results in CA exhibiting improved properties. An improved variant can have in its amino acid sequence 1 or more substitutions, 2 or more substitutions, 3 or more substitutions, 4 or more substitutions, 5 or more substitutions, 6 or more substitutions, 7 or more substitutions, 8 or more substitutions, 9 or more substitutions, 10 or more substitutions. The improved variant may additionally comprise neutral mutations. The improved variant can be substantially identical to SspCA. By "substantially identical" the sequence of the invention has an amino acid sequence which is at least about 60%, 65%, 70%, 75%, 80%, 81%, 82%, 83%, 84% 85%, 86%, 87%, 88%, 89%, 90%, 91%, 92%, 93%, 94%, 95%, 96%, 97%, 98%, 99% or 99.5% identical to SEQ ID NO 8. The substitutions comprise but are not limited to any mutations at positions listed in Tables 5, 6 and 9 or any functional derivative thereof. The mutation can be conservative or non-conservative. Non-limiting examples of conservative mutations are given in Table 3. Conservative mutations are known to usually provide similar effect to protein structure and function. The functional derivative can comprise substitution, insertion and/or deletion, or combination thereof. The variant can be free or immobilized.

TABLE 3

Possible conservative mutations

| Class | Amino acid | Conservative mutation class |
|---|---|---|
| Non-polar | A, V, L, I | Non-polar |
| | | Other non-polar |
| Other non-polar | G, M | Non-polar |
| Aromatic | H, F, Y, W | Aromatic |
| Polar | Q, N, S, T | Polar > acidic, basic |
| Acidic | D, E | Acidic > polar |
| Basic | K, R | Basic > polar |
| Other | C, P | None |

The functional derivative can have any substitution at surface-exposed residues. It is known by those skilled in the art that most neutral substitutions, i.e. mutations that retain biological and biophysical properties of a given protein, are found at these positions. Mutations tend also to be found at residue not involved in the function of the protein and away from the active site region. Table 4 describes the location and features of every SspCA residue in its 3D-structure (PDB ID 4G7A).

TABLE 4

Features of each Ssp-CA residue

| Position | Structural location/feature |
|---|---|
| X1 | Surface exposed |
| X2 | Surface exposed |
| X3 | Surface exposed |
| X4 | Surface exposed |
| X5 | Surface exposed |
| X6 | Surface exposed |
| X7 | Surface exposed |
| X8 | Surface exposed |
| X9 | Surface exposed |
| X10 | Surface exposed |
| X11 | Surface exposed |
| X12 | Surface exposed |
| X13 | Surface exposed |
| X14 | Surface exposed |
| X15 | Surface exposed |
| X16 | Buried |
| X17 | Surface exposed |
| X18 | Surface exposed |
| X19 | Surface exposed |
| X20 | Surface exposed |
| X21 | Surface exposed |
| X22 | Surface exposed |
| X23 | Surface exposed |
| X24 | Surface exposed |
| X25 | Surface exposed |
| X26 | Buried, disulfide bridge |
| X27 | Surface exposed |
| X28 | Surface exposed |
| X29 | Surface exposed |
| X30 | Surface exposed |
| X31 | Surface exposed |
| X32 | Buried |
| X33 | Surface exposed |
| X34 | Surface exposed |
| X35 | Surface exposed |
| X36 | Buried |
| X37 | Surface exposed |
| X38 | Surface exposed |
| X39 | Surface exposed |
| X40 | Surface exposed |
| X41 | Surface exposed |
| X42 | Surface exposed |
| X43 | Surface exposed |
| X44 | Surface exposed |
| X45 | Surface exposed |
| X46 | Surface exposed |
| X47 | Surface exposed |
| X48 | Surface exposed |
| X49 | Surface exposed |
| X50 | Surface exposed |
| X51 | Surface exposed |
| X52 | Surface exposed |
| X53 | Surface exposed |
| X54 | Surface exposed |
| X55 | Surface exposed |
| X56 | Buried |
| X57 | Surface exposed |
| X58 | Surface exposed |
| X59 | Buried |
| X60 | Surface exposed |
| X61 | Buried |
| X62 | Surface exposed |
| X63 | Surface exposed |
| X64 | Surface exposed |
| X65 | Surface exposed |
| X66 | Surface exposed, proton shuttle |
| X67 | Surface exposed |
| X68 | Buried |
| X69 | Surface exposed |
| X70 | Buried |
| X71 | Surface exposed |
| X72 | Surface exposed |
| X73 | Surface exposed |
| X74 | Surface exposed |
| X75 | Surface exposed |
| X76 | Surface exposed |
| X77 | Surface exposed |
| X78 | Buried |
| X79 | Surface exposed |
| X80 | Surface exposed |
| X81 | Surface exposed |
| X82 | Surface exposed |
| X83 | Surface exposed |
| X84 | Surface exposed |
| X85 | Surface exposed |
| X86 | Surface exposed |
| X87 | Surface exposed |
| X88 | Surface exposed |
| X89 | Surface exposed |
| X90 | Buried |
| X91 | Buried, metal coordinating |
| X92 | Buried |
| X93 | Buried, metal coordinating |
| X94 | Surface exposed |
| X95 | Surface exposed |
| X96 | Surface exposed |
| X97 | Surface exposed |
| X98 | Buried |
| X99 | Surface exposed |
| X100 | Surface exposed |
| X101 | Surface exposed |
| X102 | Surface exposed |
| X103 | Surface exposed |
| X104 | Surface exposed |
| X105 | Surface exposed |

TABLE 4-continued

Features of each Ssp-CA residue

| Position | Structural location/feature |
| --- | --- |
| X106 | Surface exposed |
| X107 | Buried |
| X108 | Buried |
| X109 | Buried |
| X110 | Buried, metal coordinating |
| X111 | Buried |
| X112 | Surface exposed, active site pocket |
| X113 | Buried |
| X114 | Surface exposed |
| X115 | Surface exposed |
| X116 | Surface exposed |
| X117 | Surface exposed |
| X118 | Surface exposed |
| X119 | Surface exposed |
| X120 | Surface exposed |
| X121 | Buried |
| X122 | active site pocket, inner sphere |
| X123 | Buried |
| X124 | Buried |
| X125 | Buried |
| X126 | Buried |
| X127 | Buried |
| X128 | Surface exposed |
| X129 | Surface exposed |
| X130 | Surface exposed |
| X131 | Surface exposed |
| X132 | Surface exposed |
| X133 | Surface exposed |
| X134 | Surface exposed |
| X135 | Surface exposed |
| X136 | Buried |
| X137 | Surface exposed |
| X138 | Surface exposed |
| X139 | Buried |
| X140 | Surface exposed |
| X141 | Surface exposed |
| X142 | Surface exposed |
| X143 | Surface exposed |
| X144 | Surface exposed |
| X145 | Surface exposed |
| X146 | Surface exposed |
| X147 | Surface exposed |
| X148 | Surface exposed |
| X149 | Surface exposed |
| X150 | Surface exposed |
| X151 | Surface exposed |
| X152 | Surface exposed |
| X153 | Surface exposed |
| X154 | Surface exposed |
| X155 | Surface exposed |
| X156 | Surface exposed |
| X157 | Surface exposed |
| X158 | Surface exposed |
| X159 | Surface exposed |
| X160 | Surface exposed |
| X161 | Buried |
| X162 | Surface exposed |
| X163 | Surface exposed |
| X164 | Surface exposed |
| X165 | Surface exposed |
| X166 | Surface exposed |
| X167 | Surface exposed |
| X168 | Surface exposed |
| X169 | Surface exposed |
| X170 | Surface exposed |
| X171 | Surface exposed |
| X172 | Surface exposed |
| X173 | Surface exposed |
| X174 | Buried, active site pocket |
| X175 | Surface exposed, active site pocket |
| X176 | Surface exposed, active site pocket |
| X177 | Surface exposed, active site pocket |
| X178 | Surface exposed, active site pocket |
| X179 | Surface exposed |
| X180 | Surface exposed, disulfide bridge |
| X181 | Surface exposed |
| X182 | Surface exposed |
| X183 | Surface exposed |
| X184 | Surface exposed |
| X185 | Surface exposed |
| X186 | Buried, active site pocket |
| X187 | Buried |
| X188 | Buried |
| X189 | Buried |
| X190 | Surface exposed |
| X191 | Surface exposed |
| X192 | Surface exposed |
| X193 | Surface exposed |
| X194 | Surface exposed |
| X195 | Buried |
| X196 | Surface exposed |
| X197 | Surface exposed |
| X198 | Surface exposed |
| X199 | Surface exposed |
| X200 | Surface exposed |
| X201 | Surface exposed |
| X202 | Surface exposed |
| X203 | Buried |
| X204 | Surface exposed |
| X205 | Surface exposed |
| X206 | Surface exposed |
| X207 | Surface exposed |
| X208 | Surface exposed |
| X209 | Surface exposed |
| X210 | Buried |
| X211 | Surface exposed |
| X212 | Surface exposed |
| X213 | Surface exposed |
| X214 | Surface exposed |
| X215 | Surface exposed |
| X216 | Surface exposed |
| X217 | Surface exposed |
| X218 | Surface exposed |
| X219 | Surface exposed |
| X220 | Surface exposed |
| X221 | Surface exposed |
| X222 | Surface exposed |
| X223 | Buried |
| X224 | Surface exposed |
| X225 | Surface exposed |
| X226 | Surface exposed |
| X227 | Surface exposed |

Following tables 5 and 6 describe the mutations highlighted by the directed evolution works presented herein. To the knowledge of the inventors, none of these mutations were published previously. All of these mutations occur at SspCA surface and they are well distributed. Some mutations are conservative while others are not.

Table 5 provides a description of the amino acid substitutions as reflected in SEQ ID NO, together with the observed activity of the mutated enzyme after 15 min at 92° C. The stability was evaluated by comparison of the residual activity signal level after a 15 min exposure in 0.3M $Na_2CO_3/NaHCO_3$ pH 10.

The legend for Tables 5 and 6 is:
−=Residual activity level about that of wild-type SspCA
+=Residual activity level of about 100% to 200% that of wild-type SspCA
++=Residual activity level of about 200% to 400% that of wild-type SspCA
+++=Residual activity level of about 400% to 800% that of wild-type SspCA
++++=Residual activity level of about 800% to 1600% that of wild-type SspCA
NT=Not tested

TABLE 5

Variants exhibiting improved stability following a 15 min exposure at 92° C. in 0.3M Na$_2$CO$_3$/NaHCO$_3$ pH 10

| Seq ID NO (nt/aa) | Amino acid substitution | Activity after 15 min x 929° C. Challenge † |
|---|---|---|
| 9/10 | Q18A | + |
| 15/16 | Q18L | + |
| 17/18 | Q18R | + |
| 19/20 | Q18S | + |
| 23/24 | K20A | + |
| 25/26 | K20G | + |
| 27/28 | K20L | + |
| 29/30 | K20N | + |
| 31/32 | K20R | + |
| 35/36 | K20T | + |
| 37/38 | K38A | + |
| 41/42 | K38D | + |
| 43/44 | K38G | + |
| 45/46 | K38L | + |
| 47/48 | K38N | + |
| 49/50 | K38P | + |
| 51/52 | K38R | + |
| 57/58 | Y52C | + |
| 59/60 | Y52E | + |
| 61/62 | Y52G | + |
| 63/64 | Y52P | + |
| 65/66 | Y52T | + |
| 69/70 | K57G | + |
| 73/74 | K57N | + |
| 75/76 | K57P | + |
| 77/78 | K57R | + |
| 79/80 | K57S | + |
| 81/82 | K57V | + |
| 83/84 | G82C | ++ |
| 85/86 | G82E | + |
| 87/88 | I100A | + |
| 89/90 | I100E | + |
| 91/92 | I100N | + |
| 93/94 | I100S | + |
| 97/98 | I100Y | + |
| 99/100 | E116D | + |
| 101/102 | G130A | + |
| 103/104 | G130C | + |
| 105/106 | G130L | + |
| 107/108 | K150A | + |
| 109/110 | K150S | + |
| 111/112 | N155I | + |
| 113/114 | T181L | + |
| 115/116 | T181Q | + |
| 117/118 | T181R | + |
| 119/120 | S205C | + |
| 121/122 | Q18T-K20A | + |
| 123/124 | Q18R-K20A | + |
| 125/126 | E2K; T181M; K197I | + |
| 127/128 | E14D; Q18R | + |
| 129/130 | Y52C; V122I; K150N; G226S | + |
| 131/132 | G65S; K150I | + |
| 133/134 | K57R; G130C | + |
| 135/136 | G82C; K88E | + |
| 137/138 | G82C; G148A | + |
| 139/140 | M126L; G130L | + |
| 141/142 | G82C; I100V | ++ |
| 143/144 | K38C; G82C; I100V | +++ |
| 145/146 | K38G; G82C; I100V | +++ |
| 147/148 | K38R; G82C; I100V | +++ |
| 149/150 | K38S; G82C; I100V | +++ |
| 151/152 | K38W; G82C; I100V | +++ |
| 153/154 | K38S; K57A; G82C; I100V | ++++ |
| 155/156 | K38S; K57G; G82C; I100V | ++++ |
| 157/158 | K38S; K57L; G82C; I100V | ++++ |
| 159/160 | K38S; K57S; G82C; I100V | ++++ |
| 161/162 | K38S; K57V; G82C; I100V; | ++++ |
| 163/164 | Q18F; K20G; K38S; K57L; G82C; I100V | +++++ |
| 165/166 | Q18R; K20G; K38S; K57L; G82C; I100V | +++++ |
| 167/168 | Q18W; K20G; K38S; K57L; G82C; I100V | +++++ |
| 169/170 | Q18R; K20W; K38S; K57L; G82C; I100V | +++++ |
| 171/172 | Q18R; K20A; K38S; K57L; G82C; I100V | +++++ |
| 173/174 | Q18R; K20R; K38S; K57L; G82C; I100V | +++++ |
| 175/176 | Q18C; K20S; K38S; K57L; G82C; I100V | +++++ |
| 177/178 | Q18C; K20V; K38S; K57L; G82C; I100V | +++++ |
| 179/180 | Q18A; K20T; K38S; K57L; G82C; I100V | +++++ |
| 195/196 | Q18F; K20R; K38S; K57L; G82C; I100V | +++++ |

† Stability evaluated by comparison of the residual activity signal level after a 15 min exposure in 0.3M Na$_2$CO$_3$/NaHCO$_3$ pH 10.

TABLE 6

Residual activity levels of SSp-CA variants challenged under various conditions

| Seq ID (nt/aa) | Amino acid substitution | Assay 1 0.3M Na$_2$CO$_3$ pH 10 85° C. x 16 h | Assay 2 0.3M Na$_2$CO$_3$ pH 10 96° C. x 1 h | Assay 3 0.3M Na$_2$CO$_3$ pH 10 98° C. x 1 h |
|---|---|---|---|---|
| 193/194 | E14D | NT | − | NT |
| 15/16 | Q18L | + | + | NT |
| 17/18 | Q18R | + | + | NT |
| 29/30 | K20N | + | + | NT |
| 35/36 | K20T | + | + | NT |
| 47/48 | K38N | + | + | NT |
| 57/58 | Y52C | − | + | NT |
| 73/74 | K57N | + | + | NT |
| 181/182 | G65S | NT | − | NT |
| 83/84 | G82C | ++ | ++ | + |
| 93/94 | I100S | NT | + | NT |
| 185/186 | K114I | NT | − | NT |
| 99/100 | E116D | NT | − | NT |
| 189/190 | V122I | NT | − | NT |
| 103/104 | G130C | NT | + | NT |
| 193/194 | G148A | NT | − | NT |
| 107/108 | K150A | NT | − | NT |
| 1019/110 | K150S | NT | − | NT |
| 111/112 | N155I | NT | − | NT |
| 113/114 | T181L | NT | − | NT |
| 115/116 | T181Q | NT | − | NT |
| 117/118 | T181R | NT | + | NT |
| 119/120 | S205C | NT | − | NT |
| 141/142 | G82C; I100V | ++ | ++ | ++ |
| 143/144 | K38C; G82C; I100V | ++ | NT | +++ |
| 145/146 | K38G; G82C; I100V | ++ | NT | +++ |
| 147/148 | K38R; G82C; I100V; | + | NT | ++ |
| 149/150 | K38S; G82C; I100V | +++ | NT | +++ |
| 151/152 | K38W; G82C; I100V | +++ | NT | +++ |
| 153/154 | K38S; K57A; G82C; I100V; | ++ | NT NT | +++ |
| 155/156 | K38S; K57G; G82C; I100V | NT | NT | +++ |
| 157/158 | K38S; K57L; G82C; I100V | NT | NT | +++ |
| 159/160 | K38S; K57S; G82C; I100V; | NT | NT | +++ |

TABLE 6-continued

Residual activity levels of SSp-CA variants challenged under various conditions

| Seq ID (nt/aa) | Amino acid substitution | Assay 1 0.3M Na₂CO₃ pH 10 85° C. × 16 h | Assay 2 0.3M Na₂CO₃ pH 10 96° C. × 1 h | Assay 3 0.3M Na₂CO₃ pH 10 98° C. × 1 h |
|---|---|---|---|---|
| 161/162 | K38S; K57V; G82C; I100V | NT | NT | +++ |
| 195/196 | Q18F; K20R; K38S; K57L; G82C; I100V | ++++ | NT | ++++ |
| 167/168 | Q18W; K20G; K38S; K57L; G82C; I100V | +++ | NT | +++ |
| 165/166 | Q18R; K20G; K38S; K57L; G82C; I100V | +++ | NT | +++ |
| 169/170 | Q18R; K20W; K38S; K57L; G82C; I100V | +++ | NT | +++ |
| 171/172 | Q18R; K20A; K38S; K57L; G82C; I100V | +++ | NT | +++ |
| 173/174 | Q18R; K20R; K38S; K57L; G82C; I100V | +++ | NT | +++ |

Legend:
− = Residual activity about that of wild-type SspCA
+ = Residual activity about 100% to 200% that of wild-type SspCA
++ = Residual activity about 200% to 400% that of wild-type SspCA
+++ = Residual activity about 400% to 800% that of wild-type SspCA
++++ = Residual activity about 800% to 1600% that of wild-type SspCA
NT = Not tested

TABLE 7

Neutral mutations highlighted along the screening process with SEQ ID indicated

| SEQ ID DNA/PROT | Position on SEQ ID No: 8 | Naturally occurring amino acid | Neutral mutation |
|---|---|---|---|
| 193/194 | 14 | Glu | Asp |
| 181/182 | 65 | Gly | Ser |
| 183/184 | 88 | Lys | Glu |
| 185/186 | 114 | Lys | Ile |
| 99/100 | 116 | Glu | Asp |
| 187/188 | 122 | Val | Ile |
| 189/190 | 126 | Met | Leu |
| 191/192 | 148 | Gly | Ala |
| 111/112 | 155 | Asn | Ile |
| 119/120 | 205 | Ser | Cys |

TABLE 8

Neutral peptide insertions

| Position pair between which insertion occurs on SEQ ID NO: 8 | Insertion |
|---|---|
| 12-13 | LSTGRCWCRSSTWCKLKG |
| 12-13 | PEHWAGLLPEFFWCKEKG |
| 53-54 | KLNLH |
| 151-152 | PPAEEAKT |

Table 9 provides the construction of the mutants.

TABLE 9

Mutants DNA and Polypeptide SEQ ID.

| Mutant Description | SEQ ID NO (DNA) | SEQ ID NO (Polypeptide) |
|---|---|---|
| Q18A | 9 | 10 |
| Q18C | 11 | 12 |
| Q18F | 13 | 14 |
| Q18L | 15 | 16 |
| Q18R | 17 | 18 |
| Q18S | 19 | 20 |
| Q18W | 21 | 22 |
| K20A | 23 | 24 |
| K20G | 25 | 26 |
| K20L | 27 | 28 |
| K20N | 29 | 30 |
| K20R | 31 | 32 |
| K20S | 33 | 34 |
| K20T | 35 | 36 |
| K38A | 37 | 38 |
| K38C | 39 | 40 |
| K38D | 41 | 42 |
| K38G | 43 | 44 |
| K38L | 45 | 46 |
| K38N | 47 | 48 |
| K38P | 49 | 50 |
| K38R | 51 | 52 |
| K38S | 53 | 54 |
| K38W | 55 | 56 |
| Y52C | 57 | 58 |
| Y52E | 59 | 60 |
| Y52G | 61 | 62 |
| Y52P | 63 | 64 |
| Y52T | 65 | 66 |
| K57A | 67 | 68 |
| K57G | 69 | 70 |
| K57L | 71 | 72 |
| K57N | 73 | 74 |
| K57P | 75 | 76 |
| K57R | 77 | 78 |
| K57S | 79 | 80 |
| K57V | 81 | 82 |
| G82C | 83 | 84 |
| G82E | 85 | 86 |
| I100A | 87 | 88 |
| I100E | 89 | 90 |
| I100N | 91 | 92 |
| I100S | 93 | 94 |
| I100V | 95 | 96 |
| I100Y | 97 | 98 |
| E116D | 99 | 100 |
| G130A | 101 | 102 |
| G130C | 103 | 104 |
| G130L | 105 | 106 |
| K150A | 107 | 108 |
| K150S | 109 | 110 |
| N155I | 111 | 112 |
| T181L | 113 | 114 |
| T181Q | 115 | 116 |
| T181R | 117 | 118 |
| S205C | 119 | 120 |
| Q18T-K20A | 121 | 122 |
| Q18R-K20A | 123 | 124 |
| E2K-T181M-K197I | 125 | 126 |
| E14D-Q18R | 127 | 128 |

TABLE 9-continued

Mutants DNA and Polypeptide SEQ ID.

| Mutant Description | SEQ ID NO (DNA) | SEQ ID NO (Polypeptide) |
|---|---|---|
| Y520-V122I-K150N-G226S | 129 | 130 |
| G65S-K150I | 131 | 132 |
| K57R-G130C | 133 | 134 |
| G82C-K88E | 135 | 136 |
| G82C-G148A | 137 | 138 |
| M126L-G130L | 139 | 140 |
| G82O-I100V | 141 | 142 |
| K38C-G82C-I100V | 143 | 144 |
| K38G-G82C-I100V | 145 | 146 |
| K38R-G82C-I100V | 147 | 148 |
| K38S-G82C-I100V | 149 | 150 |
| K38W-G82C-I100V | 151 | 152 |
| K38S-K57A-G82C-I100V | 153 | 154 |
| K38S-K57G-G82C-I100V | 155 | 156 |
| K38S-K57L-G82C-I100V | 157 | 158 |
| K38S-K57S-G82C-I100V | 159 | 160 |
| K38S-K57V-G82C-I100V | 161 | 162 |
| Q18F-K20G-K38S-K57L-G82C-I100V | 163 | 164 |
| Q18R-K20G-K38S-K57L-G82C-I100V | 165 | 166 |
| Q18W-K20G-K38S-K57L-G82C-I100V | 167 | 168 |
| Q18R-K20W-K38S-K57L-G82C-I100V | 169 | 170 |
| Q18R-K20A-K38S-K57L-G82C-I100V | 171 | 172 |
| Q18R-K20R-K38S-K57L-G82C-I100V | 173 | 174 |
| Q18C-K20S-K38S-K57L-G82C-I100V | 175 | 176 |
| Q18C-K20V-K38S-K57L-G82C-I100V | 177 | 178 |
| Q18A-K20T-K38S-K57L-G82C-I100V | 179 | 180 |
| G65S | 181 | 182 |
| K88E | 183 | 184 |
| K114I | 185 | 186 |
| V122I | 187 | 188 |
| M126L | 189 | 190 |
| G148A | 191 | 192 |
| E14D | 193 | 194 |
| Q18F-K20R-K38S-K57L-G82C-I100V | 195 | 196 |
| Q18T | 199 | 200 |
| K20W | 201 | 202 |
| K150I | 203 | 204 |
| K150N | 205 | 206 |
| T181M | 207 | 208 |

SEQUENCE LISTING

<160> NUMBER OF SEQ ID NOS: 208

<210> SEQ ID NO 1
<211> LENGTH: 741
<212> TYPE: DNA
<213> ORGANISM: SULFURIHYDROGENIBIUM SP.

<400> SEQUENCE: 1

```
atgagaaaaa tactaatttc tgcagtttta gtattatcaa gcatttctat atcttttgct      60
gagcatgaat ggagttatga aggtgaaaag ggaccggagc attgggcgca gttaaaacct     120
gaattctttt ggtgtaaatt aaaaaatcaa tctcctataa acattgataa aaaatataaa     180
gttaaagcaa acctgccaaa gttaaacttg tactacaaaa ctgcaaaaga atcagaagta     240
gtaaacaatg tcatactat tcagataaat ataaaagaag ataacacttt aaactacctt     300
ggagaaaagt atcagcttaa acagtttcat ttccacacac caagtgaaca tacaatagag     360
aaaaaatctt atccgttgga aattcacttt gttcataaaa cagaagatgg taagatttg      420
gtcgttggtg taatggctaa acttgggaaa actaataaag agttagataa aattttaaac     480
gttgctcctg ctgaagaagg agaaaaaatt cttgataaga atttaaattt aaacaatctc     540
ataccaaaag ataagagata tatgacatac tcaggctcat taaccactcc accatgcact     600
gaaggtgtaa gatggattgt cttgaaaaaa cctatttcta tatctaagca gcaacttgaa     660
aagttaaaat ctgttatggt gaatcctaac aacagacctg ttcaagagat taattcaaga     720
tggataattg aaggatttta a                                              741
```

<210> SEQ ID NO 2
<211> LENGTH: 246
<212> TYPE: PRT
<213> ORGANISM: SULFURIHYDROGENIBIUM SP.

```
<400> SEQUENCE: 2

Met Arg Lys Ile Leu Ile Ser Ala Val Leu Val Leu Ser Ser Ile Ser
1               5                   10                  15

Ile Ser Phe Ala Glu His Glu Trp Ser Tyr Glu Gly Glu Lys Gly Pro
                20                  25                  30

Glu His Trp Ala Gln Leu Lys Pro Glu Phe Phe Trp Cys Lys Leu Lys
            35                  40                  45

Asn Gln Ser Pro Ile Asn Ile Asp Lys Tyr Lys Val Lys Ala Asn
        50                  55                  60

Leu Pro Lys Leu Asn Leu Tyr Tyr Lys Thr Ala Lys Glu Ser Glu Val
65                  70                  75                  80

Val Asn Asn Gly His Thr Ile Gln Ile Asn Ile Lys Glu Asp Asn Thr
                85                  90                  95

Leu Asn Tyr Leu Gly Glu Lys Tyr Gln Leu Lys Gln Phe His Phe His
                100                 105                 110

Thr Pro Ser Glu His Thr Ile Glu Lys Lys Ser Tyr Pro Leu Glu Ile
            115                 120                 125

His Phe Val His Lys Thr Glu Asp Gly Lys Ile Leu Val Val Gly Val
            130                 135                 140

Met Ala Lys Leu Gly Lys Thr Asn Lys Glu Leu Asp Lys Ile Leu Asn
145                 150                 155                 160

Val Ala Pro Ala Glu Glu Gly Glu Lys Ile Leu Asp Lys Asn Leu Asn
                165                 170                 175

Leu Asn Asn Leu Ile Pro Lys Asp Lys Arg Tyr Met Thr Tyr Ser Gly
                180                 185                 190

Ser Leu Thr Thr Pro Pro Cys Thr Glu Gly Val Arg Trp Ile Val Leu
            195                 200                 205

Lys Lys Pro Ile Ser Ile Ser Lys Gln Gln Leu Glu Lys Leu Lys Ser
            210                 215                 220

Val Met Val Asn Pro Asn Asn Arg Pro Val Gln Glu Ile Asn Ser Arg
225                 230                 235                 240

Trp Ile Ile Glu Gly Phe
                245

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000
```

-continued

<210> SEQ ID NO 7
<211> LENGTH: 684
<212> TYPE: DNA
<213> ORGANISM: Sulfurihydrogenibium sp.

<400> SEQUENCE: 7

```
atggaacacg aatggagcta cgaaggtgag aagggtcctg agcattgggc gcagttgaaa    60
ccggagttct tttggtgcaa gctgaagaat caatctccga tcaacattga caagaagtac   120
aaagtcaaag cgaatctgcc gaagctgaat ctgtattaca aaccgcaaa agagagcgag    180
gttgtgaaca atggccacac tattcaaatc aacattaaag aggataacac cctgaattat   240
ctgggtgaaa agtatcaact gaagcagttt cattttcaca cgccgagcga gcataccatc   300
gagaagaagt cgtacccgtt ggaaatccac ttcgttcaca aaccgagga tggtaaaatc    360
ttggtcgtgg gtgtgatggc caaactgggt aagacgaata agagctgga caagattctg    420
aacgtggctc cggcggaaga aggtgaaaag atcctggaca aaaacctgaa cctgaacaac   480
ctgattccga agataaacg ttatatgacg tacagcggca gcctgaccac cccaccgtgt    540
acggaaggcg ttcgttggat cgttctgaag aagccgatca gcattagcaa acagcagttg   600
gagaaactga aaagcgtcat ggtcaacccg aataatcgcc cggttcaaga aatcaattcc   660
cgttggatta ttgagggctt ctaa                                          684
```

<210> SEQ ID NO 8
<211> LENGTH: 227
<212> TYPE: PRT
<213> ORGANISM: Sulfurihydrogenibium sp.

<400> SEQUENCE: 8

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile

Glu Gly Phe
225

<210> SEQ ID NO 9
<211> LENGTH: 684
<212> TYPE: DNA
<213> ORGANISM: Artificial sequence
<220> FEATURE:
<223> OTHER INFORMATION: Variant: Q18A

<400> SEQUENCE: 9

```
atggaacacg aatggagcta cgaaggtgag aagggtcctg agcattgggc ggctttgaaa      60
ccggagttct tttggtgcaa gctgaagaat caatctccga tcaacattga caagaagtac     120
aaagtcaaag cgaatctgcc gaagctgaat ctgtattaca aaccgcaaa agagagcgag      180
gttgtgaaca atggccacac tattcaaatc aacattaaag aggataacac cctgaattat     240
ctgggtgaaa agtatcaact gaagcagttt cattttcaca cgccgagcga gcataccatc    300
gagaagaagt cgtacccgtt ggaaatccac ttcgttcaca aaccgagga tggtaaaatc      360
ttggtcgtgg gtgtgatggc caaactgggt aagacgaata agagctgga caagattctg      420
aacgtggctc cggcggaaga aggtgaaaag atcctggaca aaaacctgaa cctgaacaac    480
ctgattccga agataaacg ttatatgacg tacagcggca gcctgaccac cccaccgtgt     540
acggaaggcg ttcgttggat cgttctgaag aagccgatca gcattagcaa acagcagttg     600
gagaaactga aaagcgtcat ggtcaacccg aataatcgcc cggttcaaga aatcaattcc    660
cgttggatta ttgagggctt ctaa                                           684
```

<210> SEQ ID NO 10
<211> LENGTH: 227
<212> TYPE: PRT
<213> ORGANISM: Artificial sequence
<220> FEATURE:
<223> OTHER INFORMATION: Variant: Q18A

<400> SEQUENCE: 10

```
Met Glu His Glu Trp Ser Tyr Glu Gly Glu Lys Gly Pro Glu His Trp
1               5                   10                  15
Ala Ala Leu Lys Pro Glu Phe Phe Trp Cys Lys Leu Lys Asn Gln Ser
            20                  25                  30
Pro Ile Asn Ile Asp Lys Lys Tyr Lys Val Lys Ala Asn Leu Pro Lys
        35                  40                  45
Leu Asn Leu Tyr Tyr Lys Thr Ala Lys Glu Ser Glu Val Val Asn Asn
    50                  55                  60
Gly His Thr Ile Gln Ile Asn Ile Lys Glu Asp Asn Thr Leu Asn Tyr
65                  70                  75                  80
Leu Gly Glu Lys Tyr Gln Leu Lys Gln Phe His Phe His Thr Pro Ser
                85                  90                  95
Glu His Thr Ile Glu Lys Lys Ser Tyr Pro Leu Glu Ile His Phe Val
            100                 105                 110
His Lys Thr Glu Asp Gly Lys Ile Leu Val Val Gly Val Met Ala Lys
        115                 120                 125
Leu Gly Lys Thr Asn Lys Glu Leu Asp Lys Ile Leu Asn Val Ala Pro
    130                 135                 140
Ala Glu Glu Gly Glu Lys Ile Leu Asp Lys Asn Leu Asn Leu Asn Asn
145                 150                 155                 160
```

```
Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225

<210> SEQ ID NO 11
<211> LENGTH: 684
<212> TYPE: DNA
<213> ORGANISM: Artificial sequence
<220> FEATURE:
<223> OTHER INFORMATION: Variant: Q18C

<400> SEQUENCE: 11
atggaacacg aatggagcta cgaaggtgag aagggtcctg agcattgggc gtgtttgaaa      60
ccggagttct tttggtgcaa gctgaagaat caatctccga tcaacattga caagaagtac     120
aaagtcaaag cgaatctgcc gaagctgaat ctgtattaca aaccgcaaa agagagcgag      180 gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaaccgagga tggtaaaatc     360
ttggtcgtgg gtgtgatggc caaactgggt aagacgaata agagctgga caagattctg      420 aacgtggctc cggcggaaga aggtgaaaag atcctggaca aaaacctgaa cctgaacaac     480
ctgattccga agataaacg ttatatgacg tacagcggca gcctgaccac cccaccgtgt      540
acggaaggcg ttcgttggat cgttctgaag aagccgatca gcattagcaa acagcagttg     600
gagaaactga aaagcgtcat ggtcaacccg aataatcgcc cggttcaaga aatcaattcc     660
cgttggatta ttgagggctt ctaa                                            684

<210> SEQ ID NO 12
<211> LENGTH: 227
<212> TYPE: PRT
<213> ORGANISM: Artificial sequence
<220> FEATURE:
<223> OTHER INFORMATION: Variant: Q18C

<400> SEQUENCE: 12

Met Glu His Glu Trp Ser Tyr Glu Gly Glu Lys Gly Pro Glu His Trp
1               5                   10                  15

Ala Cys Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110
```

His Lys Thr Glu Asp Gly Lys Ile Leu Val Val Gly Val Met Ala Lys
            115                 120                 125

Leu Gly Lys Thr Asn Lys Glu Leu Asp Lys Ile Leu Asn Val Ala Pro
        130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225

<210> SEQ ID NO 13
<211> LENGTH: 684
<212> TYPE: DNA
<213> ORGANISM: Artificial sequence
<220> FEATURE:
<223> OTHER INFORMATION: Variant: Q18F

<400> SEQUENCE: 13
atggaacacg aatggagcta cgaaggtgag aagggtcctg agcattgggc gttttttgaaa      60
ccggagttct tttggtgcaa gctgaagaat caatctccga tcaacattga caagaagtac     120
aaagtcaaag cgaatctgcc gaagctgaat ctgtattaca aaccgcaaa agagagcgag      180
gttgtgaaca atggccacac tattcaaatc aacattaaag aggataacac cctgaattat     240
ctgggtgaaa gtatcaact gaagcagttt cattttcaca cgccgagcga gcataccatc      300
gagaagaagt cgtacccgtt ggaaatccac ttcgttcaca aaaccgagga tggtaaaatc     360
ttggtcgtgg gtgtgatggc caaactgggt aagacgaata agagctgga caagattctg      420
aacgtggctc cggcggaaga aggtgaaaag atcctggaca aaaacctgaa cctgaacaac     480
ctgattccga agataaaacg ttatatgacg tacagcggca gcctgaccac cccaccgtgt     540
acggaaggcg ttcgttggat cgttctgaag aagccgatca gcattagcaa acagcagttg     600
gagaaactga aagcgtcat ggtcaacccg aataatcgcc cggttcaaga aatcaattcc      660
cgttggatta ttgagggctt ctaa                                             684

<210> SEQ ID NO 14
<211> LENGTH: 227
<212> TYPE: PRT
<213> ORGANISM: Artificial sequence
<220> FEATURE:
<223> OTHER INFORMATION: Variant: Q18F

<400> SEQUENCE: 14

Met Glu His Glu Trp Ser Tyr Glu Gly Glu Lys Gly Pro Glu His Trp
1               5                   10                  15

Ala Phe Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
            85                  90                  95

Glu His Thr Ile Glu Lys Lys Ser Tyr Pro Leu Glu Ile His Phe Val
                100                 105                 110

His Lys Thr Glu Asp Gly Lys Ile Leu Val Val Gly Val Met Ala Lys
            115                 120                 125

Leu Gly Lys Thr Asn Lys Glu Leu Asp Lys Ile Leu Asn Val Ala Pro
        130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225

<210> SEQ ID NO 15
<211> LENGTH: 684
<212> TYPE: DNA
<213> ORGANISM: Artificial sequence
<220> FEATURE:
<223> OTHER INFORMATION: Variant: Q18L

<400> SEQUENCE: 15
atggaacacg aatggagcta cgaaggtgag aagggtcctg agcattgggc gcttttgaaa      60
ccggagttct tttggtgcaa gctgaagaat caatctccga tcaacattga caagaagtac     120
aaagtcaaag cgaatctgcc gaagctgaat ctgtattaca aaaccgcaaa agagagcgag     180
gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaccgaggat ggtaaaatc     360 ttggtcgtgg gtgtgatggc caaactgggt aagacgaata agagctgga caagattctg     420 aacgtggctc cggcggaaga aggtgaaaag atcctggaca aaaacctgaa cctgaacaac     480
ctgattccga agataaacg ttatatgacg tacagcggca gcctgaccac cccaccgtgt     540
acggaaggcg ttcgttggat cgttctgaag aagccgatca gcattagcaa acagcagttg     600
gagaaactga aaagcgtcat ggtcaacccg aataatcgcc cggttcaaga aatcaattcc     660
cgttggatta ttgagggctt ctaa                                            684

<210> SEQ ID NO 16
<211> LENGTH: 227
<212> TYPE: PRT
<213> ORGANISM: Artificial sequence
<220> FEATURE:
<223> OTHER INFORMATION: Variant: Q18L

<400> SEQUENCE: 16

Met Glu His Glu Trp Ser Tyr Glu Gly Glu Lys Gly Pro Glu His Trp
1               5                   10                  15

Ala Leu Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
            35                  40                  45

Leu Asn Leu Tyr Tyr Lys Thr Ala Lys Glu Ser Glu Val Val Asn Asn
50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
            115                 120                 125

Leu Gly Lys Thr Asn Lys Glu Leu Asp Lys Ile Leu Asn Val Ala Pro
130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Pro Lys
            180                 185                 190

Ile Ser Ile Ser Lys Gln Gln Leu Glu Lys Leu Lys Ser Val Met Val
            195                 200                 205

Asn Pro Asn Asn Arg Pro Val Gln Glu Ile Asn Ser Arg Trp Ile Ile
210                 215                 220

Glu Gly Phe
225

<210> SEQ ID NO 17
<211> LENGTH: 684
<212> TYPE: DNA
<213> ORGANISM: Artificial sequence
<220> FEATURE:
<223> OTHER INFORMATION: Variant: Q18R

<400> SEQUENCE: 17
atggaacacg aatggagcta cgaaggtgag aagggtcctg agcattgggc gcgttttgaaa      60 ccggagttct tttggtgcaa gctgaagaat caatctccga tcaacattga caagaagtac     120
aaagtcaaag cgaatctgcc gaagctgaat ctgtattaca aaccgcaaa agagagcgag     180 gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaaccgagga tggtaaaatc     360
ttggtcgtgg gtgtgatggc caaactgggt aagacgaata aagagctgga caagattctg     420
aacgtggctc cggcggaaga aggtgaaaag atcctggaca aaaacctgaa cctgaacaac     480
ctgattccga agataaaacg ttatatgacg tacagcggca gcctgaccac cccaccgtgt     540
acggaaggcg ttcgttggat cgttctgaag aagccgatca gcattagcaa acagcagttg     600
gagaaactga aaagcgtcat ggtcaacccg aataatcgcc cggttcaaga aatcaattcc     660
cgttggatta ttgagggctt ctaa                                             684

<210> SEQ ID NO 18
<211> LENGTH: 227
<212> TYPE: PRT
<213> ORGANISM: Artificial sequence
<220> FEATURE:
<223> OTHER INFORMATION: Variant: Q18R

<400> SEQUENCE: 18

```
Met Glu His Glu Trp Ser Tyr Glu Gly Glu Lys Gly Pro Glu His Trp
1               5                   10                  15

Ala Arg Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225
```

<210> SEQ ID NO 19
<211> LENGTH: 684
<212> TYPE: DNA
<213> ORGANISM: Artificial sequence
<220> FEATURE:
<223> OTHER INFORMATION: Variant: Q18S

<400> SEQUENCE: 19

| | | | | |
|---|---|---|---|---|
| atggaacacg | aatggagcta | cgaaggtgag | aagggtcctg | agcattgggc | gtctttgaaa | 60 |
| ccggagttct | tttggtgcaa | gctgaagaat | caatctccga | tcaacattga | caagaagtac | 120 |
| aaagtcaaag | cgaatctgcc | gaagctgaat | ctgtattaca | aaccgcaaa | agagagcgag | 180 |
| gttgtgaaca | atggccacac | tattcaaatc | aacattaaag | aggataacac | cctgaattat | 240 |
| ctgggtgaaa | agtatcaact | gaagcagttt | cattttcaca | cgccgagcga | gcataccatc | 300 |
| gagaagaagt | cgtacccgtt | ggaaatccac | ttcgttcaca | aaaccgagga | tggtaaaatc | 360 |
| ttggtcgtgg | gtgtgatggc | caaactgggt | aagacgaata | aagagctgga | caagattctg | 420 |

```
aacgtggctc cggcggaaga aggtgaaaag atcctggaca aaaacctgaa cctgaacaac    480
ctgattccga agataaacg ttatatgacg tacagcggca gcctgaccac cccaccgtgt    540
acggaaggcg ttcgttggat cgttctgaag aagccgatca gcattagcaa acagcagttg    600
gagaaactga aaagcgtcat ggtcaacccg aataatcgcc cggttcaaga aatcaattcc    660
cgttggatta ttgagggctt ctaa                                          684
```

<210> SEQ ID NO 20
<211> LENGTH: 227
<212> TYPE: PRT
<213> ORGANISM: Artificial sequence
<220> FEATURE:
<223> OTHER INFORMATION: Variant: Q18S

<400> SEQUENCE: 20

```
Met Glu His Glu Trp Ser Tyr Glu Gly Glu Lys Gly Pro Glu His Trp
1               5                   10                  15

Ala Ser Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225
```

<210> SEQ ID NO 21
<211> LENGTH: 684
<212> TYPE: DNA
<213> ORGANISM: Artificial sequence
<220> FEATURE:
<223> OTHER INFORMATION: Variant: Q18W

<400> SEQUENCE: 21

```
atggaacacg aatggagcta cgaaggtgag aagggtcctg agcattgggc gtggttgaaa     60
ccggagttct tttggtgcaa gctgaagaat caatctccga tcaacattga caagaagtac    120
```

-continued

| | |
|---|---|
| aaagtcaaag cgaatctgcc gaagctgaat ctgtattaca aaaccgcaaa agagagcgag | 180 |
| gttgtgaaca atggccacac tattcaaatc aacattaaag aggataacac cctgaattat | 240 |
| ctgggtgaaa agtatcaact gaagcagttt cattttcaca cgccgagcga gcataccatc | 300 |
| gagaagaagt cgtacccgtt ggaaatccac ttcgttcaca aaaccgagga tggtaaaatc | 360 |
| ttggtcgtgg gtgtgatggc caaactgggt aagacgaata aagagctgga caagattctg | 420 |
| aacgtggctc cggcggaaga aggtgaaaag atcctggaca aaaacctgaa cctgaacaac | 480 |
| ctgattccga agataaacg ttatatgacg tacagcggca gcctgaccac cccaccgtgt | 540 |
| acggaaggcg ttcgttggat cgttctgaag aagccgatca gcattagcaa acagcagttg | 600 |
| gagaaactga aagcgtcat ggtcaacccg aataatcgcc cggttcaaga aatcaattcc | 660 |
| cgttggatta ttgagggctt ctaa | 684 |

<210> SEQ ID NO 22
<211> LENGTH: 227
<212> TYPE: PRT
<213> ORGANISM: Artificial sequence
<220> FEATURE:
<223> OTHER INFORMATION: Variant: Q18W

<400> SEQUENCE: 22

Met Glu His Glu Trp Ser Tyr Glu Gly Glu Lys Gly Pro Glu His Trp
1               5                   10                  15

Ala Trp Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225

<210> SEQ ID NO 23
<211> LENGTH: 684
<212> TYPE: DNA

<213> ORGANISM: Artificial sequence
<220> FEATURE:
<223> OTHER INFORMATION: Variant: K20A

<400> SEQUENCE: 23

```
atggaacacg aatggagcta cgaaggtgag aagggtcctg agcattgggc gcagttggct    60
ccggagttct tttggtgcaa gctgaagaat caatctccga tcaacattga caagaagtac   120
aaagtcaaag cgaatctgcc gaagctgaat ctgtattaca aaccgcaaa agagagcgag   180
gttgtgaaca atggccacac tattcaaatc aacattaaag aggataacac cctgaattat   240
ctgggtgaaa agtatcaact gaagcagttt cattttcaca cgccagcga gcataccatc   300
gagaagaagt cgtacccgtt ggaaatccac ttcgttcaca aaaccgagga tggtaaaatc   360
ttggtcgtgg gtgtgatggc caaactgggt aagacgaata agagctgga caagattctg   420
aacgtggctc cggcggaaga aggtgaaaag atcctggaca aaaacctgaa cctgaacaac   480
ctgattccga agataaacg ttatatgacg tacagcggca gcctgaccac cccaccgtgt   540
acggaaggcg ttcgttggat cgttctgaag aagccgatca gcattagcaa acagcagttg   600
gagaaactga aagcgtcat ggtcaacccg aataatcgcc cggttcaaga aatcaattcc   660
cgttggatta ttgagggctt ctaa                                         684
```

<210> SEQ ID NO 24
<211> LENGTH: 227
<212> TYPE: PRT
<213> ORGANISM: Artificial sequence
<220> FEATURE:
<223> OTHER INFORMATION: Variant: K20A

<400> SEQUENCE: 24

```
Met Glu His Glu Trp Ser Tyr Glu Gly Glu Lys Gly Pro Glu His Trp
1               5                   10                  15

Ala Gln Leu Ala Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205
```

```
Asn Pro Asn Asn Arg Pro Val Gln Glu Ile Asn Ser Arg Trp Ile Ile
    210                 215                 220

Glu Gly Phe
225
```

<210> SEQ ID NO 25
<211> LENGTH: 684
<212> TYPE: DNA
<213> ORGANISM: Artificial sequence
<220> FEATURE:
<223> OTHER INFORMATION: Variant: K20G

<400> SEQUENCE: 25

```
atggaacacg aatggagcta cgaaggtgag aagggtcctg agcattgggc gcagttgggt      60
ccggagttct tttggtgcaa gctgaagaat caatctccga tcaacattga caagaagtac     120
aaagtcaaag cgaatctgcc gaagctgaat ctgtattaca aaccgcaaa agagagcgag      180
gttgtgaaca atggccacac tattcaaatc aacattaaag aggataacac cctgaattat    240
ctgggtgaaa agtatcaact gaagcagttt cattttcaca cgccgagcga gcataccatc    300
gagaagaagt cgtacccgtt ggaaatccac ttcgttcaca aaccgagga tggtaaaatc     360
ttggtcgtgg gtgtgatggc caaactgggt aagacgaata aagagctgga caagattctg    420
aacgtggctc cggcggaaga aggtgaaaag atcctggaca aaaacctgaa cctgaacaac    480
ctgattccga agataaacg ttatatgacg tacagcggca gcctgaccac cccaccgtgt     540
acggaaggcg ttcgttggat cgttctgaag aagccgatca gcattagcaa acagcagttg    600
gagaaactga aaagcgtcat ggtcaacccg aataatcgcc cggttcaaga aatcaattcc    660
cgttggatta ttgagggctt ctaa                                              684
```

<210> SEQ ID NO 26
<211> LENGTH: 227
<212> TYPE: PRT
<213> ORGANISM: Artificial sequence
<220> FEATURE:
<223> OTHER INFORMATION: Variant: K20G

<400> SEQUENCE: 26

```
Met Glu His Glu Trp Ser Tyr Glu Gly Glu Lys Gly Pro Glu His Trp
1               5                   10                  15

Ala Gln Leu Gly Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160
```

Leu Ile Pro Lys Asp Lys Arg Tyr Met Thr Tyr Ser Gly Ser Leu Thr
            165                 170                 175

Thr Pro Pro Cys Thr Glu Gly Val Arg Trp Ile Val Leu Lys Lys Pro
        180                 185                 190

Ile Ser Ile Ser Lys Gln Gln Leu Glu Lys Leu Lys Ser Val Met Val
    195                 200                 205

Asn Pro Asn Asn Arg Pro Val Gln Glu Ile Asn Ser Arg Trp Ile Ile
    210                 215                 220

Glu Gly Phe
225

<210> SEQ ID NO 27
<211> LENGTH: 684
<212> TYPE: DNA
<213> ORGANISM: Artificial sequence
<220> FEATURE:
<223> OTHER INFORMATION: Variant: K20L

<400> SEQUENCE: 27
atggaacacg aatggagcta cgaaggtgag aagggtcctg agcattgggc gcagttgctt      60
ccggagttct tttggtgcaa gctgaagaat caatctccga tcaacattga caagaagtac     120
aaagtcaaag cgaatctgcc gaagctgaat ctgtattaca aaccgcaaa agagagcgag      180 gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaccgaagga tggtaaaatc     360
ttggtcgtgg gtgtgatggc caaactgggt aagacgaata agagctgga caagattctg      420 aacgtggctc cggcggaaga aggtgaaaag atcctggaca aaaacctgaa cctgaacaac     480
ctgattccga agataaacg ttatatgacg tacagcggca gcctgaccac cccaccgtgt      540
acggaaggcg ttcgttggat cgttctgaag aagccgatca gcattagcaa acagcagttg     600
gagaaactga aaagcgtcat ggtcaacccg aataatcgcc cggttcaaga aatcaattcc     660
cgttggatta ttgagggctt ctaa                                           684

<210> SEQ ID NO 28
<211> LENGTH: 227
<212> TYPE: PRT
<213> ORGANISM: Artificial sequence
<220> FEATURE:
<223> OTHER INFORMATION: Variant: K20L

<400> SEQUENCE: 28

Met Glu His Glu Trp Ser Tyr Glu Gly Glu Lys Gly Pro Glu His Trp
1               5                   10                  15

Ala Gln Leu Leu Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225

<210> SEQ ID NO 29
<211> LENGTH: 684
<212> TYPE: DNA
<213> ORGANISM: Artificial sequence
<220> FEATURE:
<223> OTHER INFORMATION: Variant: K20N

<400> SEQUENCE: 29

```
atggaacacg aatggagcta cgaaggtgag aagggtcctg agcattgggc gcagttgaat        60
ccggagttct tttggtgcaa gctgaagaat caatctccga tcaacattga caagaagtac       120
aaagtcaaag cgaatctgcc gaagctgaat ctgtattaca aaccgcaaa agagagcgag        180 gttgtgaaca atggccacac tattcaaatc aacattaaag aggataacac cctgaattat       240
ctgggtgaaa agtatcaact gaagcagttt cattttcaca cgccgagcga gcataccatc       300
gagaagaagt cgtacccgtt ggaaatccac ttcgttcaca aaccgaggaa tggtaaaatc       360
ttggtcgtgg gtgtgatggc caaactgggt aagacgaata agagctgga caagattctg        420 aacgtggctc cggcggaaga aggtgaaaag atcctggaca aaacctgaa cctgaacaac        480 ctgattccga agataaacg ttatatgacg tacagcggca gcctgaccac cccaccgtgt        540
acggaaggcg ttcgttggat cgttctgaag aagccgatca gcattagcaa acagcagttg       600
gagaaactga aaagcgtcat ggtcaacccg aataatcgcc cggttcaaga aatcaattcc       660
cgttggatta ttgagggctt ctaa                                              684
```

<210> SEQ ID NO 30
<211> LENGTH: 227
<212> TYPE: PRT
<213> ORGANISM: Artificial sequence
<220> FEATURE:
<223> OTHER INFORMATION: Variant: K20N

<400> SEQUENCE: 30

Met Glu His Glu Trp Ser Tyr Glu Gly Glu Lys Gly Pro Glu His Trp
1               5                   10                  15

Ala Gln Leu Asn Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

```
Leu Asn Leu Tyr Tyr Lys Thr Ala Lys Glu Ser Glu Val Val Asn Asn
 50                  55                  60
Gly His Thr Ile Gln Ile Asn Ile Lys Glu Asp Asn Thr Leu Asn Tyr
 65                  70                  75                  80
Leu Gly Glu Lys Tyr Gln Leu Lys Gln Phe His Phe His Thr Pro Ser
                 85                  90                  95
Glu His Thr Ile Glu Lys Lys Ser Tyr Pro Leu Glu Ile His Phe Val
                100                 105                 110
His Lys Thr Glu Asp Gly Lys Ile Leu Val Val Gly Val Met Ala Lys
            115                 120                 125
Leu Gly Lys Thr Asn Lys Glu Leu Asp Lys Ile Leu Asn Val Ala Pro
130                 135                 140
Ala Glu Glu Gly Glu Lys Ile Leu Asp Lys Asn Leu Asn Leu Asn Asn
145                 150                 155                 160
Leu Ile Pro Lys Asp Lys Arg Tyr Met Thr Tyr Ser Gly Ser Leu Thr
                165                 170                 175
Thr Pro Pro Cys Thr Glu Gly Val Arg Trp Ile Val Leu Lys Lys Pro
            180                 185                 190
Ile Ser Ile Ser Lys Gln Gln Leu Glu Lys Leu Lys Ser Val Met Val
                195                 200                 205
Asn Pro Asn Asn Arg Pro Val Gln Glu Ile Asn Ser Arg Trp Ile Ile
210                 215                 220
Glu Gly Phe
225
```

<210> SEQ ID NO 31
<211> LENGTH: 684
<212> TYPE: DNA
<213> ORGANISM: Artificial sequence
<220> FEATURE:
<223> OTHER INFORMATION: Variant: K20R

<400> SEQUENCE: 31

| | | |
|---|---|---|
| atggaacacg aatggagcta cgaaggtgag aagggtcctg agcattgggc gcagttgcgt | 60 |
| ccggagttct tttggtgcaa gctgaagaat caatctccga tcaacattga caagaagtac | 120 |
| aaagtcaaag cgaatctgcc gaagctgaat ctgtattaca aaccgcaaa agagagcgag | 180 |
| gttgtgaaca tggccacac tattcaaatc aacattaaag aggataacac cctgaattat | 240 |
| ctgggtgaaa agtatcaact gaagcagttt cattttcaca cgccgagcga gcataccatc | 300 |
| gagaagaagt cgtacccgtt ggaaatccac ttcgttcaca aaaccgagga tggtaaaatc | 360 |
| ttggtcgtgg gtgtgatggc caaactgggt aagacgaata agagctgga caagattctg | 420 |
| aacgtggctc cggcggaaga aggtgaaaag atcctggaca aaaacctgaa cctgaacaac | 480 |
| ctgattccga agataaacg ttatatgacg tacagcggca gcctgaccac cccaccgtgt | 540 |
| acggaaggcg ttcgttggat cgttctgaag aagccgatca gcattagcaa acagcagttg | 600 |
| gagaaactga aaagcgtcat ggtcaacccg aataatcgcc cggttcaaga aatcaattcc | 660 |
| cgttggatta ttgagggctt ctaa | 684 |

<210> SEQ ID NO 32
<211> LENGTH: 227
<212> TYPE: PRT
<213> ORGANISM: Artificial sequence
<220> FEATURE:
<223> OTHER INFORMATION: Variant: K20R

<400> SEQUENCE: 32

Met Glu His Glu Trp Ser Tyr Glu Gly Glu Lys Gly Pro Glu His Trp
1               5                   10                  15

Ala Gln Leu Arg Pro Glu Phe Phe Trp Cys Lys Leu Lys Asn Gln Ser
                20                  25                  30

Pro Ile Asn Ile Asp Lys Lys Tyr Lys Val Lys Ala Asn Leu Pro Lys
            35                  40                  45

Leu Asn Leu Tyr Tyr Lys Thr Ala Lys Glu Ser Glu Val Val Asn Asn
        50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
210                 215                 220

Glu Gly Phe
225

<210> SEQ ID NO 33
<211> LENGTH: 684
<212> TYPE: DNA
<213> ORGANISM: Artificial sequence
<220> FEATURE:
<223> OTHER INFORMATION: Variant: K20S

<400> SEQUENCE: 33
atggaacacg aatggagcta cgaaggtgag aagggtcctg agcattgggc gcagttgtct     60
ccggagttct tttggtgcaa gctgaagaat caatctccga tcaacattga caagaagtac    120
aaagtcaaag cgaatctgcc gaagctgaat ctgtattaca aaccgcaaa agagagcgag    180 gttgtgaaca atggccacac tattcaaatc aacattaaag aggataacac cctgaattat    240
ctgggtgaaa agtatcaact gaagcagttt cattttcaca cgccgagcga gcataccatc    300
gagaagaagt cgtacccgtt ggaaatccac ttcgttcaca aaaccgagga tggtaaaatc    360
ttggtcgtgg gtgtgatggc caaactgggt aagacgaata agagctgga caagattctg    420 aacgtggctc cggcggaaga aggtgaaaag atcctggaca aaaacctgaa cctgaacaac    480
ctgattccga agataaacg ttatatgacg tacagcggca gcctgaccac cccaccgtgt    540
acggaaggcg ttcgttggat cgttctgaag aagccgatca gcattagcaa acagcagttg    600
gagaaactga aaagcgtcat ggtcaacccg aataatcgcc cggttcaaga aatcaattcc    660
cgttggatta ttgagggctt ctaa                                           684

<210> SEQ ID NO 34
<211> LENGTH: 227
<212> TYPE: PRT
<213> ORGANISM: Artificial sequence
<220> FEATURE:
<223> OTHER INFORMATION: Variant: K20S

<400> SEQUENCE: 34

```
Met Glu His Glu Trp Ser Tyr Glu Gly Glu Lys Gly Pro Glu His Trp
1               5                   10                  15

Ala Gln Leu Ser Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
    195                 200                 205

Asn Pro Asn Asn Arg Pro Val Gln Glu Ile Asn Ser Arg Trp Ile Ile
210                 215                 220

Glu Gly Phe
225
```

<210> SEQ ID NO 35
<211> LENGTH: 684
<212> TYPE: DNA
<213> ORGANISM: Artificial sequence
<220> FEATURE:
<223> OTHER INFORMATION: Variant: K20T

<400> SEQUENCE: 35

| | | | | |
|---|---|---|---|---|
| atggaacacg | aatggagcta | cgaaggtgag | aagggtcctg agcattgggc | gcagttgact | 60 |
| ccggagttct | tttggtgcaa | gctgaagaat | caatctccga tcaacattga | caagaagtac | 120 |
| aaagtcaaag | cgaatctgcc | gaagctgaat | ctgtattaca aaaccgcaaa | agagagcgag | 180 |
| gttgtgaaca | atggccacac | tattcaaatc | aacattaaag aggataacac | cctgaattat | 240 |
| ctgggtgaaa | agtatcaact | gaagcagttt | cattttcaca cgccgagcga | gcataccatc | 300 |
| gagaagaagt | cgtacccgtt | ggaaatccac | ttcgttcaca aaaccgagga | tggtaaaatc | 360 |
| ttggtcgtgg | gtgtgatggc | caaactgggt | aagacgaata agagctggga | caagattctg | 420 |

```
aacgtggctc cggcggaaga aggtgaaaag atcctggaca aaaacctgaa cctgaacaac    480
ctgattccga agataaacg ttatatgacg tacagcggca gcctgaccac cccaccgtgt    540
acggaaggcg ttcgttggat cgttctgaag aagccgatca gcattagcaa acagcagttg    600
gagaaactga aaagcgtcat ggtcaacccg aataatcgcc cggttcaaga aatcaattcc    660
cgttggatta ttgagggctt ctaa                                          684
```

<210> SEQ ID NO 36
<211> LENGTH: 227
<212> TYPE: PRT
<213> ORGANISM: Artificial sequence
<220> FEATURE:
<223> OTHER INFORMATION: Variant: K20T

<400> SEQUENCE: 36

```
Met Glu His Glu Trp Ser Tyr Glu Gly Glu Lys Gly Pro Glu His Trp
1               5                   10                  15

Ala Gln Leu Thr Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225
```

<210> SEQ ID NO 37
<211> LENGTH: 684
<212> TYPE: DNA
<213> ORGANISM: Artificial sequence
<220> FEATURE:
<223> OTHER INFORMATION: Variant: K38A

<400> SEQUENCE: 37

```
atggaacacg aatggagcta cgaaggtgag aagggtcctg agcattgggc gcagttgaaa    60
ccggagttct tttggtgcaa gctgaagaat caatctccga tcaacattga cgctaagtac   120
```

```
aaagtcaaag cgaatctgcc gaagctgaat ctgtattaca aaaccgcaaa agagagcgag    180
gttgtgaaca atggccacac tattcaaatc aacattaaag aggataacac cctgaattat    240
ctgggtgaaa agtatcaact gaagcagttt cattttcaca cgccgagcga gcataccatc    300
gagaagaagt cgtacccgtt ggaaatccac ttcgttcaca aaaccgagga tggtaaaatc    360
ttggtcgtgg gtgtgatggc caaactgggt aagacgaata agagctggca agattctg     420 aacgtggctc cggcggaaga aggtgaaaag atcctggaca aaaacctgaa cctgaacaac    480
ctgattccga agataaacg ttatatgacg tacagcggca gcctgaccac cccaccgtgt     540
acggaaggcg ttcgttggat cgttctgaag aagccgatca gcattagcaa acagcagttg    600
gagaaactga aaagcgtcat ggtcaacccg aataatcgcc cggttcaaga aatcaattcc    660
cgttggatta ttgagggctt ctaa                                           684
```

```
<210> SEQ ID NO 38
<211> LENGTH: 227
<212> TYPE: PRT
<213> ORGANISM: Artificial sequence
<220> FEATURE:
<223> OTHER INFORMATION: Variant: K38A

<400> SEQUENCE: 38
```

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Ala Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225

```
<210> SEQ ID NO 39
<211> LENGTH: 684
```

```
<212> TYPE: DNA
<213> ORGANISM: Artificial sequence
<220> FEATURE:
<223> OTHER INFORMATION: Variant: K38C

<400> SEQUENCE: 39
atggaacacg aatggagcta cgaaggtgag aagggtcctg agcattgggc gcagttgaaa      60
ccggagttct tttggtgcaa gctgaagaat caatctccga tcaacattga ctgtaagtac     120
aaagtcaaag cgaatctgcc gaagctgaat ctgtattaca aaccgcaaa agagagcgag     180
gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaccgagga tggtaaaatc     360
ttggtcgtgg gtgtgatggc caaactgggt aagacgaata agagctgga caagattctg     420
aacgtggctc cggcggaaga aggtgaaaag atcctggaca aaaacctgaa cctgaacaac     480
ctgattccga agataaacg ttatatgacg tacagcggca gcctgaccac cccaccgtgt     540
acggaaggcg ttcgttggat cgttctgaag aagccgatca gcattagcaa acagcagttg     600
gagaaactga aaagcgtcat ggtcaacccg aataatcgcc cggttcaaga aatcaattcc     660
cgttggatta ttgagggctt ctaa                                           684

<210> SEQ ID NO 40
<211> LENGTH: 227
<212> TYPE: PRT
<213> ORGANISM: Artificial sequence
<220> FEATURE:
<223> OTHER INFORMATION: Variant: K38C

<400> SEQUENCE: 40

Met Glu His Glu Trp Ser Tyr Glu Gly Glu Lys Gly Pro Glu His Trp
  1               5                  10                  15

Ala Gln Leu Lys Pro Glu Phe Phe Trp Cys Lys Leu Lys Asn Gln Ser
             20                  25                  30

Pro Ile Asn Ile Asp Cys Lys Tyr Lys Val Lys Ala Asn Leu Pro Lys
         35                  40                  45

Leu Asn Leu Tyr Tyr Lys Thr Ala Lys Glu Ser Glu Val Val Asn Asn
     50                  55                  60

Gly His Thr Ile Gln Ile Asn Ile Lys Glu Asp Asn Thr Leu Asn Tyr
 65                  70                  75                  80

Leu Gly Glu Lys Tyr Gln Leu Lys Gln Phe His Phe His Thr Pro Ser
                 85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205
```

```
Asn Pro Asn Arg Pro Val Gln Glu Ile Asn Ser Arg Trp Ile Ile
    210                 215                 220

Glu Gly Phe
225
```

<210> SEQ ID NO 41
<211> LENGTH: 684
<212> TYPE: DNA
<213> ORGANISM: Artificial sequence
<220> FEATURE:
<223> OTHER INFORMATION: Variant: K38D

<400> SEQUENCE: 41

```
atggaacacg aatggagcta cgaaggtgag aagggtcctg agcattgggc gcagttgaaa    60
ccggagttct tttggtgcaa gctgaagaat caatctccga tcaacattga cgataagtac   120
aaagtcaaag cgaatctgcc gaagctgaat ctgtattaca aaccgcaaa agagagcgag    180
gttgtgaaca atggccacac tattcaaatc aacattaaag aggataacac cctgaattat   240
ctgggtgaaa agtatcaact gaagcagttt cattttcaca cgccgagcga gcataccatc   300
gagaagaagt cgtacccgtt ggaaatccac ttcgttcaca aaaccgagga tggtaaaatc   360
ttggtcgtgg gtgtgatggc caaactgggt aagacgaata aagagctgga caagattctg   420
aacgtggctc cggcggaaga aggtgaaaag atcctggaca aaaacctgaa cctgaacaac   480
ctgattccga agataaacg ttatatgacg tacagcggca gcctgaccac cccaccgtgt   540
acggaaggcg ttcgttggat cgttctgaag aagccgatca gcattagcaa acagcagttg   600
gagaaactga aaagcgtcat ggtcaacccg aataatcgcc cggttcaaga aatcaattcc   660
cgttggatta ttgagggctt ctaa                                          684
```

<210> SEQ ID NO 42
<211> LENGTH: 227
<212> TYPE: PRT
<213> ORGANISM: Artificial sequence
<220> FEATURE:
<223> OTHER INFORMATION: Variant: K38D

<400> SEQUENCE: 42

```
Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Asp Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
```

```
                145                 150                 155                 160
Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
                180                 185                 190

Ile Ser Ile Ser Lys Gln Gln Leu Glu Lys Leu Lys Ser Val Met Val
                195                 200                 205

Asn Pro Asn Asn Arg Pro Val Gln Glu Ile Asn Ser Arg Trp Ile Ile
                210                 215                 220

Glu Gly Phe
225

<210> SEQ ID NO 43
<211> LENGTH: 684
<212> TYPE: DNA
<213> ORGANISM: Artificial sequence
<220> FEATURE:
<223> OTHER INFORMATION: Variant: K38G

<400> SEQUENCE: 43
atggaacacg aatggagcta cgaaggtgag aagggtcctg agcattgggc gcagttgaaa        60
ccggagttct tttggtgcaa gctgaagaat caatctccga tcaacattga cggtaagtac       120
aaagtcaaag cgaatctgcc gaagctgaat ctgtattaca aaccgcaaa agagagcgag       180 gttgtgaaca atggccacac tattcaaatc aacattaaag aggataacac cctgaattat       240
ctgggtgaaa agtatcaact gaagcagttt cattttcaca cgccgagcga gcataccatc       300
gagaagaagt cgtacccgtt ggaaatccac ttcgttcaca aaaccgagga tggtaaaatc       360
ttggtcgtgg gtgtgatggc caaactgggt aagacgaata agagctgga caagattctg       420 aacgtggctc cggcggaaga aggtgaaaag atcctggaca aaaacctgaa cctgaacaac       480
ctgattccga agataaaacg ttatatgacg tacagcggca gcctgaccac cccaccgtgt       540
acggaaggcg ttcgttggat cgttctgaag aagccgatca gcattagcaa acagcagttg       600
gagaaactga aaagcgtcat ggtcaacccg aataatcgcc cggttcaaga aatcaattcc       660
cgttggatta ttgagggctt ctaa                                              684

<210> SEQ ID NO 44
<211> LENGTH: 227
<212> TYPE: PRT
<213> ORGANISM: Artificial sequence
<220> FEATURE:
<223> OTHER INFORMATION: Variant: K38G

<400> SEQUENCE: 44

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
                20                  25                  30

Pro Ile Asn Ile Asp Gly Lys Tyr Lys Val Lys Ala Asn Leu Pro Lys
                35                  40                  45

Leu Asn Leu Tyr Tyr Lys Thr Ala Lys Glu Ser Glu Val Val Asn Asn
                50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95
```

```
Glu His Thr Ile Glu Lys Lys Ser Tyr Pro Leu Glu Ile His Phe Val
            100                 105                 110
His Lys Thr Glu Asp Gly Lys Ile Leu Val Val Gly Val Met Ala Lys
        115                 120                 125
Leu Gly Lys Thr Asn Lys Glu Leu Asp Lys Ile Leu Asn Val Ala Pro
    130                 135                 140
Ala Glu Glu Gly Glu Lys Ile Leu Asp Lys Asn Leu Asn Leu Asn Asn
145                 150                 155                 160
Leu Ile Pro Lys Asp Lys Arg Tyr Met Thr Tyr Ser Gly Ser Leu Thr
                165                 170                 175
Thr Pro Pro Cys Thr Glu Gly Val Arg Trp Ile Val Leu Lys Lys Pro
            180                 185                 190
Ile Ser Ile Ser Lys Gln Gln Leu Glu Lys Leu Lys Ser Val Met Val
        195                 200                 205
Asn Pro Asn Asn Arg Pro Val Gln Glu Ile Asn Ser Arg Trp Ile Ile
    210                 215                 220
Glu Gly Phe
225
```

<210> SEQ ID NO 45
<211> LENGTH: 684
<212> TYPE: DNA
<213> ORGANISM: Artificial sequence
<220> FEATURE:
<223> OTHER INFORMATION: Variant: K38L

<400> SEQUENCE: 45

```
atggaacacg aatggagcta cgaaggtgag aagggtcctg agcattgggc gcagttgaaa      60
ccggagttct tttggtgcaa gctgaagaat caatctccga tcaacattga ccttaagtac     120
aaagtcaaag cgaatctgcc gaagctgaat ctgtattaca aaccgcaaa agagagcgag     180
gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaaccgagga tggtaaaatc     360
ttggtcgtgg gtgtgatggc caaactgggt aagacgaata aagagctgga caagattctg     420
aacgtggctc cggcggaaga aggtgaaaag atcctggaca aaaacctgaa cctgaacaac     480
ctgattccga agataaaacg ttatatgacg tacagcggca gcctgaccac cccaccgtgt     540
acggaaggcg ttcgttggat cgttctgaag aagccgatca gcattagcaa acagcagttg     600
gagaaactga aaagcgtcat ggtcaacccg aataatcgcc cggttcaaga aatcaattcc     660
cgttggatta ttgagggctt ctaa                                            684
```

<210> SEQ ID NO 46
<211> LENGTH: 227
<212> TYPE: PRT
<213> ORGANISM: Artificial sequence
<220> FEATURE:
<223> OTHER INFORMATION: Variant: K38L

<400> SEQUENCE: 46

```
Met Glu His Glu Trp Ser Tyr Glu Gly Glu Lys Gly Pro Glu His Trp
1               5                   10                  15
Ala Gln Leu Lys Pro Glu Phe Phe Trp Cys Lys Leu Lys Asn Gln Ser
            20                  25                  30
Pro Ile Asn Ile Asp Leu Lys Tyr Lys Val Lys Ala Asn Leu Pro Lys
        35                  40                  45
```

Leu Asn Leu Tyr Tyr Lys Thr Ala Lys Glu Ser Glu Val Val Asn Asn
 50                  55                  60

Gly His Thr Ile Gln Ile Asn Ile Lys Glu Asp Asn Thr Leu Asn Tyr
 65                  70                  75                  80

Leu Gly Glu Lys Tyr Gln Leu Lys Gln Phe His Phe His Thr Pro Ser
                 85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
210                 215                 220

Glu Gly Phe
225

<210> SEQ ID NO 47
<211> LENGTH: 684
<212> TYPE: DNA
<213> ORGANISM: Artificial sequence
<220> FEATURE:
<223> OTHER INFORMATION: Variant: K38N

<400> SEQUENCE: 47
atggaacacg aatggagcta cgaaggtgag aagggtcctg agcattgggc gcagttgaaa      60
ccggagttct tttggtgcaa gctgaagaat caatctccga tcaacattga caataagtac     120
aaagtcaaag cgaatctgcc gaagctgaat ctgtattaca aaccgcaaa agagagcgag      180 gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaaccgagga tggtaaaatc     360
ttggtcgtgg gtgtgatggc caaactgggt aagacgaata agagctgga caagattctg      420 aacgtggctc cggcggaaga aggtgaaaag atcctggaca aaaacctgaa cctgaacaac     480
ctgattccga agataaacg ttatatgacg tacagcggca gcctgaccac cccaccgtgt      540
acggaaggcg ttcgttggat cgttctgaag aagccgatca gcattagcaa acagcagttg     600
gagaaactga aaagcgtcat ggtcaacccg aataatcgcc cggttcaaga aatcaattcc     660
cgttggatta ttgagggctt ctaa                                            684

<210> SEQ ID NO 48
<211> LENGTH: 227
<212> TYPE: PRT
<213> ORGANISM: Artificial sequence
<220> FEATURE:
<223> OTHER INFORMATION: Variant: K38N -continued

<400> SEQUENCE: 48

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Asn Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225

<210> SEQ ID NO 49
<211> LENGTH: 684
<212> TYPE: DNA
<213> ORGANISM: Artificial sequence
<220> FEATURE:
<223> OTHER INFORMATION: Variant: K38P

<400> SEQUENCE: 49

```
atggaacacg aatggagcta cgaaggtgag aagggtcctg agcattgggc gcagttgaaa      60
ccggagttct tttggtgcaa gctgaagaat caatctccga tcaacattga ccctaagtac     120
aaagtcaaag cgaatctgcc gaagctgaat ctgtattaca aaccgcaaa agagagcgag     180
gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaccgaggga tggtaaaatc     360
ttggtcgtgg gtgtgatggc caaactgggt aagacgaata agagctgga caagattctg     420
aacgtggctc cggcggaaga aggtgaaaag atcctggaca aaaacctgaa cctgaacaac     480
ctgattccga agataaaacg ttatatgacg tacagcggca gcctgaccac cccaccgtgt     540
acggaaggcg ttcgttggat cgttctgaag aagccgatca gcattagcaa acagcagttg     600
gagaaactga aagcgtcat ggtcaacccg aataatcgcc cggttcaaga aatcaattcc     660
```

```
cgttggatta ttgagggctt ctaa                                          684
```

<210> SEQ ID NO 50
<211> LENGTH: 227
<212> TYPE: PRT
<213> ORGANISM: Artificial sequence
<220> FEATURE:
<223> OTHER INFORMATION: Variant: K38P

<400> SEQUENCE: 50

```
Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Pro Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225
```

<210> SEQ ID NO 51
<211> LENGTH: 684
<212> TYPE: DNA
<213> ORGANISM: Artificial sequence
<220> FEATURE:
<223> OTHER INFORMATION: Variant: K38R

<400> SEQUENCE: 51

```
atggaacacg aatggagcta cgaaggtgag aagggtcctg agcattgggc gcagttgaaa    60
ccggagttct tttggtgcaa gctgaagaat caatctccga tcaacattga ccgtaagtac   120
aaagtcaaag cgaatctgcc gaagctgaat ctgtattaca aaccgcaaa agagagcgag    180 gttgtgaaca atggccacac tattcaaatc aacattaaag aggataacac cctgaattat   240
ctgggtgaaa agtatcaact gaagcagttt cattttcaca cgccgagcga gcataccatc   300
gagaagaagt cgtacccgtt ggaaatccac ttcgttcaca aaaccgagga tggtaaaatc   360
```

```
ttggtcgtgg gtgtgatggc caaactgggt aagacgaata agagctgga caagattctg      420 aacgtggctc cggcggaaga aggtgaaaag atcctggaca aaaacctgaa cctgaacaac      480
ctgattccga agataaacg ttatatgacg tacagcggca gcctgaccac cccaccgtgt       540
acggaaggcg ttcgttggat cgttctgaag aagccgatca gcattagcaa acagcagttg     600
gagaaactga aagcgtcat ggtcaacccg aataatcgcc cggttcaaga aatcaattcc       660
cgttggatta ttgagggctt ctaa                                              684
```

<210> SEQ ID NO 52
<211> LENGTH: 227
<212> TYPE: PRT
<213> ORGANISM: Artificial sequence
<220> FEATURE:
<223> OTHER INFORMATION: Variant: K38R

<400> SEQUENCE: 52

```
Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
                20                  25                  30

Pro Ile Asn Ile Asp Arg Lys Tyr Lys Val Lys Ala Asn Leu Pro Lys
            35                  40                  45

Leu Asn Leu Tyr Tyr Lys Thr Ala Lys Glu Ser Glu Val Val Asn Asn
        50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
210                 215                 220

Glu Gly Phe
225
```

<210> SEQ ID NO 53
<211> LENGTH: 684
<212> TYPE: DNA
<213> ORGANISM: Artificial sequence
<220> FEATURE:
<223> OTHER INFORMATION: Variant: K38S

<400> SEQUENCE: 53

```
atggaacacg aatggagcta cgaaggtgag aagggtcctg agcattgggc gcagttgaaa       60
```

```
ccggagttct tttggtgcaa gctgaagaat caatctccga tcaacattga ctctaagtac    120
aaagtcaaag cgaatctgcc gaagctgaat ctgtattaca aaccgcaaa agagagcgag    180 gttgtgaaca atggccacac tattcaaatc aacattaaag aggataacac cctgaattat    240
ctgggtgaaa agtatcaact gaagcagttt cattttcaca cgccgagcga gcataccatc    300
gagaagaagt cgtacccgtt ggaaatccac ttcgttcaca aaaccgagga tggtaaaatc    360
ttggtcgtgg gtgtgatggc caaactgggt aagacgaata aagagctgga caagattctg    420
aacgtggctc cggcggaaga aggtgaaaag atcctggaca aaaacctgaa cctgaacaac    480
ctgattccga agataaacg ttatatgacg tacagcggca gcctgaccac cccaccgtgt    540
acggaaggcg ttcgttggat cgttctgaag aagccgatca gcattagcaa acagcagttg    600
gagaaactga aaagcgtcat ggtcaacccg aataatcgcc cggttcaaga aatcaattcc    660
cgttggatta ttgagggctt ctaa                                           684
```

<210> SEQ ID NO 54
<211> LENGTH: 227
<212> TYPE: PRT
<213> ORGANISM: Artificial sequence
<220> FEATURE:
<223> OTHER INFORMATION: Variant: K38S

<400> SEQUENCE: 54

```
Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Ser Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225
```

<210> SEQ ID NO 55

-continued

<211> LENGTH: 684
<212> TYPE: DNA
<213> ORGANISM: Artificial sequence
<220> FEATURE:
<223> OTHER INFORMATION: Variant: K38W

<400> SEQUENCE: 55

```
atggaacacg aatggagcta cgaaggtgag aagggtcctg agcattgggc gcagttgaaa      60
ccggagttct tttggtgcaa gctgaagaat caatctccga tcaacattga ctggaagtac     120
aaagtcaaag cgaatctgcc gaagctgaat ctgtattaca aaccgcaaa agagagcgag     180
gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaaccgagga tggtaaaatc     360
ttggtcgtgg gtgtgatggc caaactgggt aagacgaata aagagctgga caagattctg     420
aacgtggctc cggcggaaga aggtgaaaag atcctggaca aaaacctgaa cctgaacaac     480
ctgattccga agataaaacg ttatatgacg tacagcggca gcctgaccac cccaccgtgt     540
acggaaggcg ttcgttggat cgttctgaag aagccgatca gcattagcaa acagcagttg     600
gagaaactga aagcgtcat ggtcaacccg aataatcgcc cggttcaaga aatcaattcc     660
cgttggatta ttgagggctt ctaa                                            684
```

<210> SEQ ID NO 56
<211> LENGTH: 227
<212> TYPE: PRT
<213> ORGANISM: Artificial sequence
<220> FEATURE:
<223> OTHER INFORMATION: Variant: K38W

<400> SEQUENCE: 56

```
Met Glu His Glu Trp Ser Tyr Glu Gly Glu Lys Gly Pro Glu His Trp
 1               5                  10                  15

Ala Gln Leu Lys Pro Glu Phe Phe Trp Cys Lys Leu Lys Asn Gln Ser
                20                  25                  30

Pro Ile Asn Ile Asp Trp Lys Tyr Lys Val Lys Ala Asn Leu Pro Lys
            35                  40                  45

Leu Asn Leu Tyr Tyr Lys Thr Ala Lys Glu Ser Glu Val Val Asn Asn
        50                  55                  60

Gly His Thr Ile Gln Ile Asn Ile Lys Glu Asp Asn Thr Leu Asn Tyr
 65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
```

```
                195                 200                 205
Asn Pro Asn Asn Arg Pro Val Gln Glu Ile Asn Ser Arg Trp Ile Ile
    210                 215                 220
Glu Gly Phe
225

<210> SEQ ID NO 57
<211> LENGTH: 684
<212> TYPE: DNA
<213> ORGANISM: Artificial sequence
<220> FEATURE:
<223> OTHER INFORMATION: Variant: Y52C

<400> SEQUENCE: 57
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtgttaca aaccgcaaa agagagcgag     180 gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtaccgtt ggaaatccac ttcgttcaca aaaccgagga tggtaaaatc     360
ttggtcgtgg gtgtgatggc aaactgggt aagacgaata agagctgga caagattctg     420 aacgtggctc cggcggaaga aggtgaaaag atcctggaca aaaaccctgaa cctgaacaac     480 ctgattccga agataaacg ttatatgacg tacagcggca gcctgaccac cccaccgtgt     540
acggaaggcg ttcgttggat cgttctgaag aagccgatca gcattagcaa acagcagttg     600
gagaaactga aaagcgtcat ggtcaacccg aataatcgcc cggttcaaga aatcaattcc     660
cgttggatta ttgagggctt ctaa                                           684

<210> SEQ ID NO 58
<211> LENGTH: 227
<212> TYPE: PRT
<213> ORGANISM: Artificial sequence
<220> FEATURE:
<223> OTHER INFORMATION: Variant: Y52C

<400> SEQUENCE: 58

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Cys Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140
```

```
Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
            165                 170                 175

Thr Pro Pro Cys Thr Glu Gly Val Arg Trp Ile Val Leu Lys Lys Pro
        180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
        210                 215                 220

Glu Gly Phe
225
```

<210> SEQ ID NO 59
<211> LENGTH: 684
<212> TYPE: DNA
<213> ORGANISM: Artificial sequence
<220> FEATURE:
<223> OTHER INFORMATION: Variant: Y52E

<400> SEQUENCE: 59

| | | |
|---|---|---|
| atggaacacg aatggagcta cgaaggtgag aagggtcctg agcattgggc gcagttgaaa | 60 |
| ccggagttct tttggtgcaa gctgaagaat caatctccga tcaacattga caagaagtac | 120 |
| aaagtcaaag cgaatctgcc gaagctgaat ctggagtaca aaccgcaaa agagagcgag | 180 |
| gttgtgaaca atggccacac tattcaaatc aacattaaag aggataacac cctgaattat | 240 |
| ctgggtgaaa agtatcaact gaagcagttt cattttcaca cgccgagcga gcataccatc | 300 |
| gagaagaagt cgtacccgtt ggaaatccac ttcgttcaca aaccgaggat ggtaaaatc | 360 |
| ttggtcgtgg gtgtgatggc caaactgggt aagacgaata agagctgga caagattctg | 420 |
| aacgtggctc cggcggaaga aggtgaaaag atcctggaca aaacctgaa cctgaacaac | 480 |
| ctgattccga agataaaacg ttatatgacg tacagcggca gcctgaccac cccaccgtgt | 540 |
| acggaaggcg ttcgttggat cgttctgaag aagccgatca gcattagcaa acagcagttg | 600 |
| gagaaactga aaagcgtcat ggtcaacccg aataatcgcc cggttcaaga aatcaattcc | 660 |
| cgttggatta ttgagggctt ctaa | 684 |

<210> SEQ ID NO 60
<211> LENGTH: 227
<212> TYPE: PRT
<213> ORGANISM: Artificial sequence
<220> FEATURE:
<223> OTHER INFORMATION: Variant: Y52E

<400> SEQUENCE: 60

```
Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Glu Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95
```

Glu His Thr Ile Glu Lys Lys Ser Tyr Pro Leu Ile His Phe Val
            100                 105                 110

His Lys Thr Glu Asp Gly Lys Ile Leu Val Gly Val Met Ala Lys
            115                 120                 125

Leu Gly Lys Thr Asn Lys Glu Leu Asp Lys Ile Leu Asn Val Ala Pro
130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
                195                 200                 205

Asn Pro Asn Asn Arg Pro Val Gln Glu Ile Asn Ser Arg Trp Ile Ile
210                 215                 220

Glu Gly Phe
225

<210> SEQ ID NO 61
<211> LENGTH: 684
<212> TYPE: DNA
<213> ORGANISM: Artificial sequence
<220> FEATURE:
<223> OTHER INFORMATION: Variant: Y52G

<400> SEQUENCE: 61
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgggttaca aaaccgcaaa agagagcgag     180
gttgtgaaca tggccacac tattcaaatc aacattaaag aggataacac cctgaattat     240
ctgggtgaaa gtatcaact gaagcagttt cattttcaca cgccgagcga gcataccatc     300
gagaagaagt cgtacccgtt ggaaatccac ttcgttcaca aaaccgagga tggtaaaatc     360
ttggtcgtgg gtgtgatggc caaactgggt aagacgaata agagctggac aagattctg     420 aacgtggctc cggcggaaga aggtgaaaag atcctggaca aaaacctgaa cctgaacaac     480
ctgattccga agataaacg ttatatgacg tacagcggca gcctgaccac cccaccgtgt     540
acggaaggcg ttcgttggat cgttctgaag aagccgatca gcattagcaa acagcagttg     600
gagaaactga aaagcgtcat ggtcaacccg aataatcgcc cggttcaaga aatcaattcc     660
cgttggatta ttgagggctt ctaa                                            684

<210> SEQ ID NO 62
<211> LENGTH: 227
<212> TYPE: PRT
<213> ORGANISM: Artificial sequence
<220> FEATURE:
<223> OTHER INFORMATION: Variant: Y52G

<400> SEQUENCE: 62

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys

```
                35                  40                  45

Leu Asn Leu Gly Tyr Lys Thr Ala Lys Glu Ser Glu Val Val Asn Asn
 50                  55                  60

Gly His Thr Ile Gln Ile Asn Ile Lys Glu Asp Asn Thr Leu Asn Tyr
 65                  70                  75                  80

Leu Gly Glu Lys Tyr Gln Leu Lys Gln Phe His Phe His Thr Pro Ser
                 85                  90                  95

Glu His Thr Ile Glu Lys Lys Ser Tyr Pro Leu Glu Ile His Phe Val
                100                 105                 110

His Lys Thr Glu Asp Gly Lys Ile Leu Val Val Gly Val Met Ala Lys
                115                 120                 125

Leu Gly Lys Thr Asn Lys Glu Leu Asp Lys Ile Leu Asn Val Ala Pro
130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
                180                 185                 190

Ile Ser Ile Ser Lys Gln Gln Leu Glu Lys Leu Lys Ser Val Met Val
                195                 200                 205

Asn Pro Asn Asn Arg Pro Val Gln Glu Ile Asn Ser Arg Trp Ile Ile
210                 215                 220

Glu Gly Phe
225

<210> SEQ ID NO 63
<211> LENGTH: 684
<212> TYPE: DNA
<213> ORGANISM: Artificial sequence
<220> FEATURE:
<223> OTHER INFORMATION: Variant: Y52P

<400> SEQUENCE: 63
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgccttaca aaccgcaaa agagagcgag      180 gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaccgaggga tggtaaaatc     360
ttggtcgtgg gtgtgatggc caaactgggt aagacgaata agagctgga caagattctg      420 aacgtggctc cggcggaaga aggtgaaaag atcctggaca aaaacctgaa cctgaacaac     480
ctgattccga agataaacg ttatatgacg tacagcggca gcctgaccac cccaccgtgt     540
acggaaggcg ttcgttggat cgttctgaag aagccgatca gcattagcaa acagcagttg     600
gagaaactga aagcgtcat ggtcaacccg aataatcgcc cggttcaaga aatcaattcc     660
cgttggatta ttgagggctt ctaa                                            684

<210> SEQ ID NO 64
<211> LENGTH: 227
<212> TYPE: PRT
<213> ORGANISM: Artificial sequence
<220> FEATURE:
<223> OTHER INFORMATION: Variant: Y52P
```

<400> SEQUENCE: 64

```
Met Glu His Glu Trp Ser Tyr Glu Gly Glu Lys Gly Pro Glu His Trp
1               5                   10                  15
Ala Gln Leu Lys Pro Glu Phe Phe Trp Cys Lys Leu Lys Asn Gln Ser
            20                  25                  30
Pro Ile Asn Ile Asp Lys Lys Tyr Lys Val Lys Ala Asn Leu Pro Lys
        35                  40                  45
Leu Asn Leu Pro Tyr Lys Thr Ala Lys Glu Ser Glu Val Val Asn Asn
    50                  55                  60
Gly His Thr Ile Gln Ile Asn Ile Lys Glu Asp Asn Thr Leu Asn Tyr
65                  70                  75                  80
Leu Gly Glu Lys Tyr Gln Leu Lys Gln Phe His Phe His Thr Pro Ser
                85                  90                  95
Glu His Thr Ile Glu Lys Lys Ser Tyr Pro Leu Glu Ile His Phe Val
            100                 105                 110
His Lys Thr Glu Asp Gly Lys Ile Leu Val Val Gly Val Met Ala Lys
        115                 120                 125
Leu Gly Lys Thr Asn Lys Glu Leu Asp Lys Ile Leu Asn Val Ala Pro
    130                 135                 140
Ala Glu Glu Gly Glu Lys Ile Leu Asp Lys Asn Leu Asn Leu Asn Asn
145                 150                 155                 160
Leu Ile Pro Lys Asp Lys Arg Tyr Met Thr Tyr Ser Gly Ser Leu Thr
                165                 170                 175
Thr Pro Pro Cys Thr Glu Gly Val Arg Trp Ile Val Leu Lys Lys Pro
            180                 185                 190
Ile Ser Ile Ser Lys Gln Gln Leu Glu Lys Leu Lys Ser Val Met Val
        195                 200                 205
Asn Pro Asn Asn Arg Pro Val Gln Glu Ile Asn Ser Arg Trp Ile Ile
    210                 215                 220
Glu Gly Phe
225
```

<210> SEQ ID NO 65
<211> LENGTH: 684
<212> TYPE: DNA
<213> ORGANISM: Artificial sequence
<220> FEATURE:
<223> OTHER INFORMATION: Variant: Y52T

<400> SEQUENCE: 65

| | |
|---|---|
| atggaacacg aatggagcta cgaaggtgag aagggtcctg agcattgggc gcagttgaaa | 60 |
| ccggagttct tttggtgcaa gctgaagaat caatctccga tcaacattga caagaagtac | 120 |
| aaagtcaaag cgaatctgcc gaagctgaat ctgacttaca aaccgcaaa agagagcgag | 180 |
| gttgtgaaca atggccacac tattcaaatc aacattaaag aggataacac cctgaattat | 240 |
| ctgggtgaaa agtatcaact gaagcagttt cattttcaca cgccgagcga gcataccatc | 300 |
| gagaagaagt cgtacccgtt ggaaatccac ttcgttcaca aaccgagga tggtaaaatc | 360 |
| ttggtcgtgg gtgtgatggc caaactgggt aagacgaata agagctgga caagattctg | 420 |
| aacgtggctc cggcggaaga aggtgaaaag atcctggaca aaaacctgaa cctgaacaac | 480 |
| ctgattccga agataaacg ttatatgacg tacagcggca gcctgaccac cccaccgtgt | 540 |
| acggaaggcg ttcgttggat cgttctgaag aagccgatca gcattagcaa acagcagttg | 600 |
| gagaaactga aaagcgtcat ggtcaacccg aataatcgcc cggttcaaga aatcaattcc | 660 | cgttggatta ttgagggctt ctaa                                                684

<210> SEQ ID NO 66
<211> LENGTH: 227
<212> TYPE: PRT
<213> ORGANISM: Artificial sequence
<220> FEATURE:
<223> OTHER INFORMATION: Variant: Y52T

<400> SEQUENCE: 66

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Thr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225

<210> SEQ ID NO 67
<211> LENGTH: 684
<212> TYPE: DNA
<213> ORGANISM: Artificial sequence
<220> FEATURE:
<223> OTHER INFORMATION: Variant: K57A

<400> SEQUENCE: 67
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaccgcagc tgagagcgag     180 gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaccgagga tggtaaaatc     360

```
ttggtcgtgg gtgtgatggc caaactgggt aagacgaata aagagctgga caagattctg    420
aacgtggctc cggcggaaga aggtgaaaag atcctggaca aaaacctgaa cctgaacaac    480
ctgattccga agataaacg ttatatgacg tacagcggca gcctgaccac cccaccgtgt    540
acggaaggcg ttcgttggat cgttctgaag aagccgatca gcattagcaa acagcagttg    600
gagaaactga aagcgtcat ggtcaacccg aataatcgcc cggttcaaga aatcaattcc    660
cgttggatta ttgagggctt ctaa                                          684
```

<210> SEQ ID NO 68
<211> LENGTH: 227
<212> TYPE: PRT
<213> ORGANISM: Artificial sequence
<220> FEATURE:
<223> OTHER INFORMATION: Variant: K57A

<400> SEQUENCE: 68

```
Met Glu His Glu Trp Ser Tyr Glu Gly Glu Lys Gly Pro Glu His Trp
  1               5                  10                  15

Ala Gln Leu Lys Pro Glu Phe Phe Trp Cys Lys Leu Lys Asn Gln Ser
             20                  25                  30

Pro Ile Asn Ile Asp Lys Lys Tyr Lys Val Lys Ala Asn Leu Pro Lys
         35                  40                  45

Leu Asn Leu Tyr Tyr Lys Thr Ala Ala Glu Ser Glu Val Val Asn Asn
     50                  55                  60

Gly His Thr Ile Gln Ile Asn Ile Lys Glu Asp Asn Thr Leu Asn Tyr
 65                  70                  75                  80

Leu Gly Glu Lys Tyr Gln Leu Lys Gln Phe His Phe His Thr Pro Ser
                 85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225
```

<210> SEQ ID NO 69
<211> LENGTH: 684
<212> TYPE: DNA
<213> ORGANISM: Artificial sequence
<220> FEATURE:
<223> OTHER INFORMATION: Variant: K57G

<400> SEQUENCE: 69

```
atggaacacg aatggagcta cgaaggtgag aagggtcctg agcattgggc gcagttgaaa     60
```

```
ccggagttct tttggtgcaa gctgaagaat caatctccga tcaacattga caagaagtac    120
aaagtcaaag cgaatctgcc gaagctgaat ctgtattaca aaaccgcagg tgagagcgag    180
gttgtgaaca atggccacac tattcaaatc aacattaaag aggataacac cctgaattat    240
ctgggtgaaa agtatcaact gaagcagttt cattttcaca cgccgagcga gcataccatc    300
gagaagaagt cgtacccgtt ggaaatccac ttcgttcaca aaaccgagga tggtaaaatc    360
ttggtcgtgg gtgtgatggc caaactgggt aagacgaata aagagctgga caagattctg    420
aacgtggctc cggcggaaga aggtgaaaag atcctggaca aaaacctgaa cctgaacaac    480
ctgattccga agataaacg ttatatgacg tacagcggca gcctgaccac cccaccgtgt    540
acggaaggcg ttcgttggat cgttctgaag aagccgatca gcattagcaa acagcagttg    600
gagaaactga aaagcgtcat ggtcaacccg aataatcgcc cggttcaaga aatcaattcc    660
cgttggatta ttgagggctt ctaa                                          684
```

<210> SEQ ID NO 70  
<211> LENGTH: 227  
<212> TYPE: PRT  
<213> ORGANISM: Artificial sequence  
<220> FEATURE:  
<223> OTHER INFORMATION: Variant: K57G
<400> SEQUENCE: 70

```
Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Gly Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225
```

-continued

<210> SEQ ID NO 71
<211> LENGTH: 684
<212> TYPE: DNA
<213> ORGANISM: Artificial sequence
<220> FEATURE:
<223> OTHER INFORMATION: Variant: K57L

<400> SEQUENCE: 71

```
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaccgcact tgagagcgag      180
gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaaccgagga tggtaaaatc     360
ttggtcgtgg gtgtgatggc caaactgggt aagacgaata agagctgga caagattctg      420
aacgtggctc cggcggaaga aggtgaaaag atcctggaca aaaacctgaa cctgaacaac     480
ctgattccga agataaacg ttatatgacg tacagcggca gcctgaccac cccaccgtgt      540
acggaaggcg ttcgttggat cgttctgaag aagccgatca gcattagcaa acagcagttg     600
gagaaactga aagcgtcat ggtcaacccg aataatcgcc cggttcaaga aatcaattcc      660
cgttggatta ttgagggctt ctaa                                              684
```

<210> SEQ ID NO 72
<211> LENGTH: 227
<212> TYPE: PRT
<213> ORGANISM: Artificial sequence
<220> FEATURE:
<223> OTHER INFORMATION: Variant: K57L

<400> SEQUENCE: 72

```
Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Leu Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190
```

Ile Ser Ile Ser Lys Gln Gln Leu Glu Lys Leu Lys Ser Val Met Val
            195                 200                 205

Asn Pro Asn Asn Arg Pro Val Gln Glu Ile Asn Ser Arg Trp Ile Ile
            210                 215                 220

Glu Gly Phe
225

<210> SEQ ID NO 73
<211> LENGTH: 684
<212> TYPE: DNA
<213> ORGANISM: Artificial sequence
<220> FEATURE:
<223> OTHER INFORMATION: Variant: K57N

<400> SEQUENCE: 73

```
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaccgcaaa tgagagcgag      180
gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaccgagga tggtaaaatc      360
ttggtcgtgg gtgtgatggc caaactgggt aagacgaata agagctgga caagattctg      420
aacgtggctc cggcggaaga aggtgaaaag atcctggaca aaaacctgaa cctgaacaac     480
ctgattccga agataaaacg ttatatgacg tacagcggca gcctgaccac cccaccgtgt     540
acggaaggcg ttcgttggat cgttctgaag aagccgatca gcattagcaa acagcagttg     600
gagaaactga aaagcgtcat ggtcaacccg aataatcgcc cggttcaaga aatcaattcc     660
cgttggatta ttgagggctt ctaa                                            684
```

<210> SEQ ID NO 74
<211> LENGTH: 227
<212> TYPE: PRT
<213> ORGANISM: Artificial sequence
<220> FEATURE:
<223> OTHER INFORMATION: Variant: K57N

<400> SEQUENCE: 74

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Asn Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
            165                 170                 175

Thr Pro Pro Cys Thr Glu Gly Val Arg Trp Ile Val Leu Lys Lys Pro
        180                 185                 190

Ile Ser Ile Ser Lys Gln Gln Leu Gly Lys Leu Lys Ser Val Met Val
            195                 200                 205

Asn Pro Asn Asn Arg Pro Val Gln Glu Ile Asn Ser Arg Trp Ile Ile
        210                 215                 220

Glu Gly Phe
225

<210> SEQ ID NO 75
<211> LENGTH: 684
<212> TYPE: DNA
<213> ORGANISM: Artificial sequence
<220> FEATURE:
<223> OTHER INFORMATION: Variant: K57P

<400> SEQUENCE: 75
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaccgcacc tgagagcgag      180 gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaccgaggga tggtaaaatc     360
ttggtcgtgg gtgtgatggc caaactgggt aagacgaata agagctggaa caagattctg     420
aacgtggctc cggcggaaga aggtgaaaag atcctggaca aaaacctgaa cctgaacaac     480
ctgattccga agataaacg ttatatgacg tacagcggca gcctgaccac cccaccgtgt      540
acggaaggcg ttcgttggat cgttctgaag aagccgatca gcattagcaa acagcagttg     600
gagaaactga aaagcgtcat ggtcaacccg aataatcgcc ggttcaaga aatcaattcc      660 cgttggatta ttgagggctt ctaa                                            684

<210> SEQ ID NO 76
<211> LENGTH: 227
<212> TYPE: PRT
<213> ORGANISM: Artificial sequence
<220> FEATURE:
<223> OTHER INFORMATION: Variant: K57P

<400> SEQUENCE: 76

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Pro Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser

```
                85                  90                  95
Glu His Thr Ile Glu Lys Lys Ser Tyr Pro Leu Glu Ile His Phe Val
                100                 105                 110

His Lys Thr Glu Asp Gly Lys Ile Leu Val Val Gly Val Met Ala Lys
            115                 120                 125

Leu Gly Lys Thr Asn Lys Glu Leu Asp Lys Ile Leu Asn Val Ala Pro
        130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
                180                 185                 190

Ile Ser Ile Ser Lys Gln Gln Leu Glu Lys Leu Lys Ser Val Met Val
                195                 200                 205

Asn Pro Asn Asn Arg Pro Val Gln Glu Ile Asn Ser Arg Trp Ile Ile
                210                 215                 220

Glu Gly Phe
225

<210> SEQ ID NO 77
<211> LENGTH: 684
<212> TYPE: DNA
<213> ORGANISM: Artificial sequence
<220> FEATURE:
<223> OTHER INFORMATION: Variant: K57R

<400> SEQUENCE: 77
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaccgcacg tgagagcgag      180 gttgtgaaca atggccacac tattcaaatc aacattaaag aggataacac cctgaattat     240
ctgggtgaaa gtatcaact gaagcagttt cattttcaca cgccgagcga gcataccatc      300
gagaagaagt cgtacccgtt ggaaatccac ttcgttcaca aaaccgagga tggtaaaatc     360
ttggtcgtgg gtgtgatggc caaactgggt aagacgaata agagctgga caagattctg      420 aacgtggctc cggcggaaga aggtgaaaag atcctggaca aaaacctgaa cctgaacaac     480
ctgattccga agataaaacg ttatatgacg tacagcggca gcctgaccac cccaccgtgt     540
acggaaggcg ttcgttggat cgttctgaag aagccgatca gcattagcaa acagcagttg     600
gagaaactga aagcgtcat ggtcaacccg aataatcgcc cggttcaaga aatcaattcc      660
cgttggatta ttgagggctt ctaa                                             684

<210> SEQ ID NO 78
<211> LENGTH: 227
<212> TYPE: PRT
<213> ORGANISM: Artificial sequence
<220> FEATURE:
<223> OTHER INFORMATION: Variant: K57R

<400> SEQUENCE: 78

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30
```

```
Pro Ile Asn Ile Asp Lys Lys Tyr Lys Val Lys Ala Asn Leu Pro Lys
             35                  40                  45

Leu Asn Leu Tyr Tyr Lys Thr Ala Arg Glu Ser Glu Val Val Asn Asn
 50                  55                  60

Gly His Thr Ile Gln Ile Asn Ile Lys Glu Asp Asn Thr Leu Asn Tyr
 65                  70                  75                  80

Leu Gly Glu Lys Tyr Gln Leu Lys Gln Phe His Phe Thr Pro Ser
                 85                  90                  95

Glu His Thr Ile Glu Lys Lys Ser Tyr Pro Leu Glu Ile His Phe Val
                100                 105                 110

His Lys Thr Glu Asp Gly Lys Ile Leu Val Val Gly Val Met Ala Lys
            115                 120                 125

Leu Gly Lys Thr Asn Lys Glu Leu Asp Lys Ile Leu Asn Val Ala Pro
130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
210                 215                 220

Glu Gly Phe
225
```

<210> SEQ ID NO 79
<211> LENGTH: 684
<212> TYPE: DNA
<213> ORGANISM: Artificial sequence
<220> FEATURE:
<223> OTHER INFORMATION: Variant: K57S

<400> SEQUENCE: 79

```
atggaacacg aatggagcta cgaaggtgag aagggtcctg agcattgggc gcagttgaaa      60
ccggagttct tttggtgcaa gctgaagaat caatctccga tcaacattga caagaagtac    120
aaagtcaaag cgaatctgcc gaagctgaat ctgtattaca aaccgcatc tgagagcgag     180
gttgtgaaca tggccacac tattcaaatc aacattaaag aggataacac cctgaattat    240
ctgggtgaaa agtatcaact gaagcagttt cattttcaca cgccgagcga gcataccatc    300
gagaagaagt cgtacccgtt ggaaatccac ttcgttcaca aaccgaggat ggtaaaatc    360
ttggtcgtgg gtgtgatggc caaactgggt aagacgaata agagctggac aagattctg    420
aacgtggctc cggcggaaga aggtgaaaag atcctggaca aaaacctgaa cctgaacaac    480
ctgattccga agataaacg ttatatgacg tacagcggca gcctgaccac cccaccgtgt    540
acggaaggcg ttcgttggat cgttctgaag aagccgatca gcattagcaa acagcagttg    600
gagaaactga aaagcgtcat ggtcaacccg aataatcgcc cggttcaaga aatcaattcc    660
cgttggatta ttgagggctt ctaa                                            684
```

<210> SEQ ID NO 80
<211> LENGTH: 227
<212> TYPE: PRT
<213> ORGANISM: Artificial sequence
<220> FEATURE:

<223> OTHER INFORMATION: Variant: K57S

<400> SEQUENCE: 80

```
Met Glu His Glu Trp Ser Tyr Glu Gly Lys Gly Pro Glu His Trp
1               5                   10                  15
Ala Gln Leu Lys Pro Glu Phe Phe Trp Cys Lys Leu Lys Asn Gln Ser
            20                  25                  30
Pro Ile Asn Ile Asp Lys Lys Tyr Lys Val Lys Ala Asn Leu Pro Lys
        35                  40                  45
Leu Asn Leu Tyr Tyr Lys Thr Ala Ser Glu Ser Glu Val Val Asn Asn
    50                  55                  60
Gly His Thr Ile Gln Ile Asn Ile Lys Glu Asp Asn Thr Leu Asn Tyr
65                  70                  75                  80
Leu Gly Glu Lys Tyr Gln Leu Lys Gln Phe His Phe His Thr Pro Ser
                85                  90                  95
Glu His Thr Ile Glu Lys Lys Ser Tyr Pro Leu Glu Ile His Phe Val
            100                 105                 110
His Lys Thr Glu Asp Gly Lys Ile Leu Val Val Gly Val Met Ala Lys
        115                 120                 125
Leu Gly Lys Thr Asn Lys Glu Leu Asp Lys Ile Leu Asn Val Ala Pro
    130                 135                 140
Ala Glu Glu Gly Glu Lys Ile Leu Asp Lys Asn Leu Asn Leu Asn Asn
145                 150                 155                 160
Leu Ile Pro Lys Asp Lys Arg Tyr Met Thr Tyr Ser Gly Ser Leu Thr
                165                 170                 175
Thr Pro Pro Cys Thr Glu Gly Val Arg Trp Ile Val Leu Lys Lys Pro
            180                 185                 190
Ile Ser Ile Ser Lys Gln Gln Leu Glu Lys Leu Lys Ser Val Met Val
        195                 200                 205
Asn Pro Asn Asn Arg Pro Val Gln Glu Ile Asn Ser Arg Trp Ile Ile
    210                 215                 220
Glu Gly Phe
225
```

<210> SEQ ID NO 81
<211> LENGTH: 684
<212> TYPE: DNA
<213> ORGANISM: Artificial sequence
<220> FEATURE:
<223> OTHER INFORMATION: Variant: K57V

<400> SEQUENCE: 81

```
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaccgcagt tgagagcgag      180
gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaccgaggga tggtaaaatc     360
ttggtcgtgg gtgtgatggc caaactgggt aagacgaata agagctgga caagattctg      420
aacgtggctc cggcggaaga aggtgaaaag atcctggaca aaaacctgaa cctgaacaac     480
ctgattccga agataaacg ttatatgacg tacagcggca gcctgaccac cccaccgtgt      540
acggaaggcg ttcgttggat cgttctgaag aagccgatca gcattagcaa acagcagttg     600
```

```
gagaaactga aaagcgtcat ggtcaacccg aataatcgcc cggttcaaga aatcaattcc    660
cgttggatta ttgagggctt ctaa                                           684
```

<210> SEQ ID NO 82
<211> LENGTH: 227
<212> TYPE: PRT
<213> ORGANISM: Artificial sequence
<220> FEATURE:
<223> OTHER INFORMATION: Variant: K57V

<400> SEQUENCE: 82

```
Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Val Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225
```

<210> SEQ ID NO 83
<211> LENGTH: 684
<212> TYPE: DNA
<213> ORGANISM: Artificial sequence
<220> FEATURE:
<223> OTHER INFORMATION: Variant: G82C

<400> SEQUENCE: 83

```
atggaacacg aatggagcta cgaaggtgag aagggtcctg agcattgggc gcagttgaaa    60
ccggagttct tttggtgcaa gctgaagaat caatctccga tcaacattga caagaagtac   120
aaagtcaaag cgaatctgcc gaagctgaat ctgtattaca aaccgcaaa agagagcgag    180 gttgtgaaca atggccacac tattcaaatc aacattaaag aggataacac cctgaattat   240
ctgtgtgaaa agtatcaact gaagcagttt cattttcaca cgccgagcga gcataccatc   300
```

```
gagaagaagt cgtacccgtt ggaaatccac ttcgttcaca aaaccgagga tggtaaaatc    360
ttggtcgtgg gtgtgatggc caaactgggt aagacgaata agagctgga caagattctg     420 aacgtggctc cggcggaaga aggtgaaaag atcctggaca aaaacctgaa cctgaacaac    480
ctgattccga agataaacg ttatatgacg tacagcggca gcctgaccac cccaccgtgt     540
acggaaggcg ttcgttggat cgttctgaag aagccgatca gcattagcaa acagcagttg    600
gagaaactga aaagcgtcat ggtcaacccg aataatcgcc cggttcaaga aatcaattcc    660
cgttggatta ttgagggctt ctaa                                            684
```

<210> SEQ ID NO 84
<211> LENGTH: 227
<212> TYPE: PRT
<213> ORGANISM: Artificial sequence
<220> FEATURE:
<223> OTHER INFORMATION: Variant: G82C

<400> SEQUENCE: 84

```
Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Cys Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225
```

<210> SEQ ID NO 85
<211> LENGTH: 684
<212> TYPE: DNA
<213> ORGANISM: Artificial sequence
<220> FEATURE:
<223> OTHER INFORMATION: Variant: G82E

<400> SEQUENCE: 85

```
atggaacacg aatggagcta cgaaggtgag aagggtcctg agcattgggc gcagttgaaa      60
ccggagttct tttggtgcaa gctgaagaat caatctccga tcaacattga caagaagtac    120
aaagtcaaag cgaatctgcc gaagctgaat ctgtattaca aaccgcaaa agagagcgag     180
gttgtgaaca atggccacac tattcaaatc aacattaaag aggataacac cctgaattat    240
ctggaggaaa agtatcaact gaagcagttt cattttcaca cgccgagcga gcataccatc    300
gagaagaagt cgtacccgtt ggaaatccac ttcgttcaca aaaccgagga tggtaaaatc    360
ttggtcgtgg gtgtgatggc caaactgggt aagacgaata aagagctgga caagattctg    420
aacgtggctc cggcggaaga aggtgaaaag atcctggaca aaaacctgaa cctgaacaac    480
ctgattccga agataaacg ttatatgacg tacagcggca gcctgaccac cccaccgtgt     540
acggaaggcg ttcgttggat cgttctgaag aagccgatca gcattagcaa acagcagttg    600
gagaaactga aagcgtcat ggtcaacccg aataatcgcc cggttcaaga aatcaattcc     660
cgttggatta ttgagggctt ctaa                                             684
```

<210> SEQ ID NO 86
<211> LENGTH: 227
<212> TYPE: PRT
<213> ORGANISM: Artificial sequence
<220> FEATURE:
<223> OTHER INFORMATION: Variant: G82E

<400> SEQUENCE: 86

```
Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Glu Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225
```

<210> SEQ ID NO 87
<211> LENGTH: 684
<212> TYPE: DNA
<213> ORGANISM: Artificial sequence
<220> FEATURE:
<223> OTHER INFORMATION: Variant: I100A

<400> SEQUENCE: 87

```
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaccgcaaa agagagcgag      180
gttgtgaaca atggccacac tattcaaatc aacattaaag aggataacac cctgaattat     240
ctgggtgaaa agtatcaact gaagcagttt cattttcaca cgccgagcga gcataccgct     300
gagaagaagt cgtacccgtt ggaaatccac ttcgttcaca aaaccgagga tggtaaaatc     360
ttggtcgtgg gtgtgatggc caaactgggt aagacgaata agagctgga caagattctg      420
aacgtggctc cggcggaaga aggtgaaaag atcctggaca aaaacctgaa cctgaacaac     480
ctgattccga agataaaacg ttatatgacg tacagcggca gcctgaccac cccaccgtgt     540
acggaaggcg ttcgttggat cgttctgaag aagccgatca gcattagcaa acagcagttg     600
gagaaactga aaagcgtcat ggtcaacccg aataatcgcc cggttcaaga aatcaattcc     660
cgttggatta ttgagggctt ctaa                                             684
```

<210> SEQ ID NO 88
<211> LENGTH: 227
<212> TYPE: PRT
<213> ORGANISM: Artificial sequence
<220> FEATURE:
<223> OTHER INFORMATION: Variant: I100A

<400> SEQUENCE: 88

```
Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ala Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190
```

```
Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
        210                 215                 220

Glu Gly Phe
225

<210> SEQ ID NO 89
<211> LENGTH: 684
<212> TYPE: DNA
<213> ORGANISM: Artificial sequence
<220> FEATURE:
<223> OTHER INFORMATION: Variant: I100E

<400> SEQUENCE: 89
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaccgcaaa agagagcgag     180 gttgtgaaca atggccacac tattcaaatc aacattaaag aggataacac cctgaattat     240
ctgggtgaaa agtatcaact gaagcagttt cattttcaca cgccgagcga gcataccgag     300
gagaagaagt cgtacccgtt ggaaatccac ttcgttcaca aaccgaggga tggtaaaatc     360
ttggtcgtgg gtgtgatggc caaactgggt aagacgaata agagctgga caagattctg     420 aacgtggctc cggcggaaga aggtgaaaag atcctggaca aaacctgaa cctgaacaac     480 ctgattccga agataaacg ttatatgacg tacagcggca gcctgaccac cccaccgtgt     540
acggaaggcg ttcgttggat cgttctgaag aagccgatca gcattagcaa acagcagttg     600
gagaaactga aaagcgtcat ggtcaacccg aataatcgcc cggttcaaga aatcaattcc     660
cgttggatta ttgagggctt ctaa                                            684

<210> SEQ ID NO 90
<211> LENGTH: 227
<212> TYPE: PRT
<213> ORGANISM: Artificial sequence
<220> FEATURE:
<223> OTHER INFORMATION: Variant: I100E

<400> SEQUENCE: 90

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Glu Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
```

```
                130                 135                 140
Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Gly Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225

<210> SEQ ID NO 91
<211> LENGTH: 684
<212> TYPE: DNA
<213> ORGANISM: Artificial sequence
<220> FEATURE:
<223> OTHER INFORMATION: Variant: I100N

<400> SEQUENCE: 91
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaccgcaaa agagagcgag      180 gttgtgaaca atggccacac tattcaaatc aacattaaag aggataacac cctgaattat     240
ctgggtgaaa gtatcaact gaagcagttt cattttcaca cgccgagcga gcataccaat      300
gagaagaagt cgtaccccgtt ggaaatccac ttcgttcaca aaaccgagga tggtaaaatc    360
ttggtcgtgg gtgtgatggc caaactgggt aagacgaata agagctgga caagattctg     420 aacgtggctc cggcggaaga aggtgaaaag atcctggaca aaaacctgaa cctgaacaac    480
ctgattccga agataaacg ttatatgacg tacagcggca gcctgaccac cccaccgtgt     540
acggaaggcg ttcgttggat cgttctgaag aagccgatca gcattagcaa acagcagttg    600
gagaaactga aagcgtcat ggtcaacccg aataatcgcc cggttcaaga aatcaattcc    660
cgttggatta ttgagggctt ctaa                                           684

<210> SEQ ID NO 92
<211> LENGTH: 227
<212> TYPE: PRT
<213> ORGANISM: Artificial sequence
<220> FEATURE:
<223> OTHER INFORMATION: Variant: I100N

<400> SEQUENCE: 92

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80
```

```
Leu Gly Glu Lys Tyr Gln Leu Lys Gln Phe His Phe His Thr Pro Ser
             85                  90                  95
Glu His Thr Asn Glu Lys Lys Ser Tyr Pro Leu Glu Ile His Phe Val
        100                 105                 110
His Lys Thr Glu Asp Gly Lys Ile Leu Val Val Gly Val Met Ala Lys
        115                 120                 125
Leu Gly Lys Thr Asn Lys Glu Leu Asp Lys Ile Leu Asn Val Ala Pro
    130                 135                 140
Ala Glu Glu Gly Glu Lys Ile Leu Asp Lys Asn Leu Asn Leu Asn Asn
145                 150                 155                 160
Leu Ile Pro Lys Asp Lys Arg Tyr Met Thr Tyr Ser Gly Ser Leu Thr
                165                 170                 175
Thr Pro Pro Cys Thr Glu Gly Val Arg Trp Ile Val Leu Lys Lys Pro
            180                 185                 190
Ile Ser Ile Ser Lys Gln Gln Leu Glu Lys Leu Lys Ser Val Met Val
        195                 200                 205
Asn Pro Asn Asn Arg Pro Val Gln Glu Ile Asn Ser Arg Trp Ile Ile
    210                 215                 220
Glu Gly Phe
225

<210> SEQ ID NO 93
<211> LENGTH: 684
<212> TYPE: DNA
<213> ORGANISM: Artificial sequence
<220> FEATURE:
<223> OTHER INFORMATION: Variant: I100S

<400> SEQUENCE: 93
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaccgcaaa agagagcgag      180 gttgtgaaca atggccacac tattcaaatc aacattaaag aggataacac cctgaattat     240
ctgggtgaaa agtatcaact gaagcagttt cattttcaca cgccgagcga gcataccctct   300 gagaagaagt cgtacccgtt ggaaatccac ttcgttcaca aaaccgagga tggtaaaatc     360
ttggtcgtgg gtgtgatggc caaactgggt aagacgaata aagagctgga caagattctg     420
aacgtggctc cggcggaaga aggtgaaaag atcctggaca aaaacctgaa cctgaacaac     480
ctgattccga agataaacg ttatatgacg tacagcggca gcctgaccac cccaccgtgt     540
acggaaggcg ttcgttggat cgttctgaag aagccgatca gcattagcaa acagcagttg     600
gagaaactga aaagcgtcat ggtcaacccg aataatcgcc cggttcaaga aatcaattcc    660
cgttggatta ttgagggctt ctaa                                            684

<210> SEQ ID NO 94
<211> LENGTH: 227
<212> TYPE: PRT
<213> ORGANISM: Artificial sequence
<220> FEATURE:
<223> OTHER INFORMATION: Variant: I100S

<400> SEQUENCE: 94

Met Glu His Glu Trp Ser Tyr Glu Gly Glu Lys Gly Pro Glu His Trp
1               5                  10                  15
Ala Gln Leu Lys Pro Glu Phe Phe Trp Cys Lys Leu Lys Asn Gln Ser
            20                  25                  30
```

Pro Ile Asn Ile Asp Lys Lys Tyr Lys Val Lys Ala Asn Leu Pro Lys
            35                  40                  45

Leu Asn Leu Tyr Tyr Lys Thr Ala Lys Glu Ser Glu Val Val Asn Asn
 50                  55                  60

Gly His Thr Ile Gln Ile Asn Ile Lys Glu Asp Asn Thr Leu Asn Tyr
 65                  70                  75                  80

Leu Gly Glu Lys Tyr Gln Leu Lys Gln Phe His Phe His Thr Pro Ser
                 85                  90                  95

Glu His Thr Ser Glu Lys Lys Ser Tyr Pro Leu Glu Ile His Phe Val
            100                 105                 110

His Lys Thr Glu Asp Gly Lys Ile Leu Val Val Gly Val Met Ala Lys
            115                 120                 125

Leu Gly Lys Thr Asn Lys Glu Leu Asp Lys Ile Leu Asn Val Ala Pro
130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
            195                 200                 205

Asn Pro Asn Asn Arg Pro Val Gln Glu Ile Asn Ser Arg Trp Ile Ile
            210                 215                 220

Glu Gly Phe
225

<210> SEQ ID NO 95
<211> LENGTH: 684
<212> TYPE: DNA
<213> ORGANISM: Artificial sequence
<220> FEATURE:
<223> OTHER INFORMATION: Variant: I100V

<400> SEQUENCE: 95

```
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaccgcaaa agagagcgag      180
gttgtgaaca tggccacac tattcaaatc aacattaaag aggataacac cctgaattat     240
ctgggtgaaa agtatcaact gaagcagttt cattttcaca cgccgagcga gcataccgtt     300
gagaagaagt cgtacccgtt ggaaatccac ttcgttcaca aaaccgagga tggtaaaatc     360
ttggtcgtgg gtgtgatggc caaactgggt aagacgaata aagagctgga caagattctg     420
aacgtggctc cggcggaaga aggtgaaaag atcctggaca aaaacctgaa cctgaacaac     480
ctgattccga agataaacg ttatatgacg tacagcggca gcctgaccac cccaccgtgt     540
acggaaggcg ttcgttggat cgttctgaag aagccgatca gcattagcaa acagcagttg     600
gagaaactga aaagcgtcat ggtcaacccg aataatcgcc cggttcaaga aatcaattcc     660
cgttggatta ttgagggctt ctaa                                             684
```

<210> SEQ ID NO 96
<211> LENGTH: 227
<212> TYPE: PRT
<213> ORGANISM: Artificial sequence

```
<220> FEATURE:
<223> OTHER INFORMATION: Variant: I100V

<400> SEQUENCE: 96

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Val Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
210                 215                 220

Glu Gly Phe
225

<210> SEQ ID NO 97
<211> LENGTH: 684
<212> TYPE: DNA
<213> ORGANISM: Artificial sequence
<220> FEATURE:
<223> OTHER INFORMATION: Variant: I100Y

<400> SEQUENCE: 97
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaccgcaaa agagagcgag      180 gttgtgaaca atggccacac tattcaaatc aacattaaag aggataacac cctgaattat     240
ctgggtgaaa agtatcaact gaagcagttt cattttcaca cgccgagcga gcatacctat     300
gagaagaagt cgtacccgtt ggaaatccac ttcgttcaca aaaccgagga tgtaaaatc      360 ttggtcgtgg gtgtgatggc caaactgggt aagacgaata agagctgga  caagattctg    420 aacgtggctc cggcggaaga aggtgaaaag atcctggaca aaaacctgaa cctgaacaac     480
ctgattccga agataaaacg ttatatgacg tacagcggca gcctgaccac cccaccgtgt     540
acggaaggcg ttcgttggat cgttctgaag aagccgatca gcattagcaa acagcagttg     600
```

```
gagaaactga aaagcgtcat ggtcaacccg aataatcgcc cggttcaaga aatcaattcc      660
cgttggatta ttgagggctt ctaa                                            684
```

<210> SEQ ID NO 98
<211> LENGTH: 227
<212> TYPE: PRT
<213> ORGANISM: Artificial sequence
<220> FEATURE:
<223> OTHER INFORMATION: Variant: I100Y

<400> SEQUENCE: 98

```
Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Tyr Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225
```

<210> SEQ ID NO 99
<211> LENGTH: 684
<212> TYPE: DNA
<213> ORGANISM: Artificial sequence
<220> FEATURE:
<223> OTHER INFORMATION: Variant: E116D

<400> SEQUENCE: 99

```
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaccgcaaa agagagcgag     180 gttgtgaaca atggccacac tattcaaatc aacattaaag aggataacac cctgaattat     240
ctgggtgaaa agtatcaact gaagcagttt cattttcaca cgccgagcga gcataccatc     300
```

```
gagaagaagt cgtacccgtt ggaaatccac ttcgttcaca aaaccgatga tggtaaaatc    360
ttggtcgtgg gtgtgatggc caaactgggt aagacgaata aagagctgga caagattctg    420
aacgtggctc cggcggaaga aggtgaaaag atcctggaca aaacctgaa cctgaacaac     480 ctgattccga agataaaacg ttatatgacg tacagcggga gcctgaccac cccaccgtgt    540
acggaaggcg ttcgttggat cgttctgaag aagccgatca gcattagcaa acagcagttg    600
gagaaactga aaagcgtcat ggtcaacccg aataatcgcc cggttcaaga aatcaattcc    660
cgttggatta ttgagggctt ctaa                                           684
```

```
<210> SEQ ID NO 100
<211> LENGTH: 227
<212> TYPE: PRT
<213> ORGANISM: Artificial sequence
<220> FEATURE:
<223> OTHER INFORMATION: Variant: E116D

<400> SEQUENCE: 100
```

```
Met Glu His Glu Trp Ser Tyr Glu Gly Glu Lys Gly Pro Glu His Trp
 1               5                  10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Asp Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225
```

```
<210> SEQ ID NO 101
<211> LENGTH: 684
<212> TYPE: DNA
<213> ORGANISM: Artificial sequence
<220> FEATURE:
<223> OTHER INFORMATION: Variant: G130A

<400> SEQUENCE: 101
```

```
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaccgcaaa agagagcgag      180 gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaaccgagga tggtaaaatc     360
ttggtcgtgg gtgtgatggc caaactggct aagacgaata agagctgga caagattctg      420 aacgtggctc cggcggaaga aggtgaaaag atcctggaca aaaacctgaa cctgaacaac     480
ctgattccga agataaacg ttatatgacg tacagcggca gcctgaccac cccaccgtgt      540
acggaaggcg ttcgttggat cgttctgaag aagccgatca gcattagcaa acagcagttg     600
gagaaactga aaagcgtcat ggtcaacccg aataatcgcc cggttcaaga aatcaattcc     660
cgttggatta ttgagggctt ctaa                                            684
```

<210> SEQ ID NO 102
<211> LENGTH: 227
<212> TYPE: PRT
<213> ORGANISM: Artificial sequence
<220> FEATURE:
<223> OTHER INFORMATION: Variant: G130A

<400> SEQUENCE: 102

```
Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Ala Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225
```

<210> SEQ ID NO 103
<211> LENGTH: 684
<212> TYPE: DNA
<213> ORGANISM: Artificial sequence
<220> FEATURE:
<223> OTHER INFORMATION: Variant: G130C

<400> SEQUENCE: 103

```
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaccgcaaa agagagcgag      180
gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaccgagga tggtaaaatc      360
ttggtcgtgg gtgtgatggc caaactgtgt aagacgaata agagctgga caagattctg      420
aacgtggctc cggcggaaga aggtgaaaag atcctggaca aaaacctgaa cctgaacaac     480
ctgattccga agataaaacg ttatatgacg tacagcggca gcctgaccac cccaccgtgt     540
acggaaggcg ttcgttggat cgttctgaag aagccgatca gcattagcaa acagcagttg     600
gagaaactga aaagcgtcat ggtcaacccg aataatcgcc cggttcaaga aatcaattcc     660
cgttggatta ttgagggctt ctaa                                            684
```

<210> SEQ ID NO 104
<211> LENGTH: 227
<212> TYPE: PRT
<213> ORGANISM: Artificial sequence
<220> FEATURE:
<223> OTHER INFORMATION: Variant: G130C

<400> SEQUENCE: 104

```
Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Cys Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
```

```
                  180                 185                 190
Ile Ser Ile Ser Lys Gln Gln Leu Glu Lys Leu Lys Ser Val Met Val
            195                 200                 205

Asn Pro Asn Asn Arg Pro Val Gln Glu Ile Asn Ser Arg Trp Ile Ile
            210                 215                 220

Glu Gly Phe
225

<210> SEQ ID NO 105
<211> LENGTH: 684
<212> TYPE: DNA
<213> ORGANISM: Artificial sequence
<220> FEATURE:
<223> OTHER INFORMATION: Variant: G130L

<400> SEQUENCE: 105
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaccgcaaa agagagcgag      180 gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaaccgagga tggtaaaatc     360
ttggtcgtgg gtgtgatggc caaactgctt aagacgaata agagctgga caagattctg      420 aacgtggctc cggcggaaga aggtgaaaag atcctggaca aaaacctgaa cctgaacaac     480
ctgattccga agataaacg ttatatgacg tacagcggca gcctgaccac cccaccgtgt      540
acggaaggcg ttcgttggat cgttctgaag aagccgatca gcattagcaa acagcagttg     600
gagaaactga aaagcgtcat ggtcaacccg aataatcgcc cggttcaaga aatcaattcc     660
cgttggatta ttgagggctt ctaa                                             684

<210> SEQ ID NO 106
<211> LENGTH: 227
<212> TYPE: PRT
<213> ORGANISM: Artificial sequence
<220> FEATURE:
<223> OTHER INFORMATION: Variant: G130L

<400> SEQUENCE: 106

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125
```

```
Leu Leu Lys Thr Asn Lys Glu Leu Asp Lys Ile Leu Asn Val Ala Pro
    130                 135                 140
Ala Glu Glu Gly Glu Lys Ile Leu Asp Lys Asn Leu Asn Leu Asn Asn
145                 150                 155                 160
Leu Ile Pro Lys Asp Lys Arg Tyr Met Thr Tyr Ser Gly Ser Leu Thr
                165                 170                 175
Thr Pro Pro Cys Thr Glu Gly Val Arg Trp Ile Val Leu Lys Lys Pro
                180                 185                 190
Ile Ser Ile Ser Lys Gln Gln Leu Glu Lys Leu Lys Ser Val Met Val
                195                 200                 205
Asn Pro Asn Asn Arg Pro Val Gln Glu Ile Asn Ser Arg Trp Ile Ile
    210                 215                 220
Glu Gly Phe
225
```

<210> SEQ ID NO 107
<211> LENGTH: 684
<212> TYPE: DNA
<213> ORGANISM: Artificial sequence
<220> FEATURE:
<223> OTHER INFORMATION: Variant: K150A

<400> SEQUENCE: 107

```
atggaacacg aatggagcta cgaaggtgag aagggtcctg agcattgggc gcagttgaaa    60
ccggagttct tttggtgcaa gctgaagaat caatctccga tcaacattga caagaagtac   120
aaagtcaaag cgaatctgcc gaagctgaat ctgtattaca aaccgcaaa agagagcgag   180
gttgtgaaca atggccacac tattcaaatc aacattaaag aggataacac cctgaattat   240
ctgggtgaaa agtatcaact gaagcagttt cattttcaca cgccgagcga gcataccatc   300
gagaagaagt cgtacccgtt ggaaatccac ttcgttcaca aaaccgagga tggtaaaatc   360
ttggtcgtgg gtgtgatggc caaactgggt aagacgaata agagctgga caagattctg   420
aacgtggctc cggcggaaga aggtgaagct atcctggaca aaaacctgaa cctgaacaac   480
ctgattccga agataaaacg ttatatgacg tacagcggca gcctgaccac cccaccgtgt   540
acggaaggcg ttcgttggat cgttctgaag aagccgatca gcattagcaa acagcagttg   600
gagaaactga aaagcgtcat ggtcaacccg aataatcgcc cggttcaaga aatcaattcc   660
cgttggatta ttgagggctt ctaa                                          684
```

<210> SEQ ID NO 108
<211> LENGTH: 227
<212> TYPE: PRT
<213> ORGANISM: Artificial sequence
<220> FEATURE:
<223> OTHER INFORMATION: Variant: K150A

<400> SEQUENCE: 108

```
Met Glu His Glu Trp Ser Tyr Glu Gly Glu Lys Gly Pro Glu His Trp
1               5                   10                  15
Ala Gln Leu Lys Pro Glu Phe Phe Trp Cys Lys Leu Lys Asn Gln Ser
                20                  25                  30
Pro Ile Asn Ile Asp Lys Lys Tyr Lys Val Lys Ala Asn Leu Pro Lys
            35                  40                  45
Leu Asn Leu Tyr Tyr Lys Thr Ala Lys Glu Ser Glu Val Val Asn Asn
    50                  55                  60
Gly His Thr Ile Gln Ile Asn Ile Lys Glu Asp Asn Thr Leu Asn Tyr
65                  70                  75                  80
```

```
Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
            115                 120                 125

Leu Gly Lys Thr Asn Lys Glu Leu Asp Lys Ile Leu Asn Val Ala Pro
        130                 135                 140

Ala Glu Glu Gly Glu Ala Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Gly Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225
```

<210> SEQ ID NO 109
<211> LENGTH: 684
<212> TYPE: DNA
<213> ORGANISM: Artificial sequence
<220> FEATURE:
<223> OTHER INFORMATION: Variant: K150S

<400> SEQUENCE: 109

```
atggaacacg aatggagcta cgaaggtgag aagggtcctg agcattgggc gcagttgaaa    60
ccggagttct tttggtgcaa gctgaagaat caatctccga tcaacattga caagaagtac   120
aaagtcaaag cgaatctgcc gaagctgaat ctgtattaca aaccgcaaa agagagcgag   180
gttgtgaaca atggccacac tattcaaatc aacattaaag aggataacac cctgaattat   240
ctgggtgaaa gtatcaact gaagcagttt cattttcaca cgccgagcga gcataccatc   300
gagaagaagt cgtacccgtt ggaaatccac ttcgttcaca aaccgaggga tggtaaaatc   360
ttggtcgtgg gtgtgatggc caaactgggt aagacgaata agagctgga caagattctg   420
aacgtggctc cggcggaaga aggtgaatct atcctggaca aaaacctgaa cctgaacaac   480
ctgattccga agataaaacg ttatatgacg tacagcggca gcctgaccac cccaccgtgt   540
acggaaggcg ttcgttggat cgttctgaag aagccgatca gcattagcaa acagcagttg   600
gagaaactga aaagcgtcat ggtcaacccg aataatcgcc ggttcaagaa atcaattcc    660
cgttggatta ttgagggctt ctaa                                         684
```

<210> SEQ ID NO 110
<211> LENGTH: 227
<212> TYPE: PRT
<213> ORGANISM: Artificial sequence
<220> FEATURE:
<223> OTHER INFORMATION: Variant: K150S

<400> SEQUENCE: 110

```
Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
```

```
                    20                  25                  30

Pro Ile Asn Ile Asp Lys Lys Tyr Lys Val Lys Ala Asn Leu Pro Lys
            35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
130                 135                 140

Ala Glu Glu Gly Glu Ser Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225

<210> SEQ ID NO 111
<211> LENGTH: 684
<212> TYPE: DNA
<213> ORGANISM: Artificial sequence
<220> FEATURE:
<223> OTHER INFORMATION: Variant: N155I

<400> SEQUENCE: 111
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaccgcaaa agagagcgag      180 gttgtgaaca atggccacac tattcaaatc aacattaaag aggataacac cctgaattat     240
ctgggtgaaa agtatcaact gaagcagttt cattttcaca cgccgagcga ataccatc       300 gagaagaagt cgtacccgtt ggaaatccac ttcgttcaca aaaccgagga tggtaaaatc     360
ttggtcgtgg gtgtgatggc caaactgggt aagacgaata agagctgga caagattctg      420 aacgtggctc cggcggaaga aggtgaaaag atcctggaca aatcctgaa cctgaacaac      480 ctgattccga agataaacg ttatatgacg tacagcggca gcctgaccac cccaccgtgt      540
acggaaggcg ttcgttggat cgttctgaag aagccgatca gcattagcaa acagcagttg     600
gagaaactga aaagcgtcat ggtcaacccg aataatcgcc ggttcaagaa atcaattcc      660 cgttggatta ttgagggctt ctaa                                              684

<210> SEQ ID NO 112
<211> LENGTH: 227
<212> TYPE: PRT
```

<213> ORGANISM: Artificial sequence
<220> FEATURE:
<223> OTHER INFORMATION: Variant: N155I

<400> SEQUENCE: 112

```
Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Ile Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225
```

<210> SEQ ID NO 113
<211> LENGTH: 684
<212> TYPE: DNA
<213> ORGANISM: Artificial sequence
<220> FEATURE:
<223> OTHER INFORMATION: Variant: T181L

<400> SEQUENCE: 113

| | | | | |
|---|---|---|---|---|
| atggaacacg | aatggagcta | cgaaggtgag | aagggtcctg | agcattgggc | gcagttgaaa | 60 |
| ccggagttct | tttggtgcaa | gctgaagaat | caatctccga | tcaacattga | caagaagtac | 120 |
| aaagtcaaag | cgaatctgcc | gaagctgaat | ctgtattaca | aaccgcaaa | agagagcgag | 180 |
| gttgtgaaca | atggccacac | tattcaaatc | aacattaaag | aggataacac | cctgaattat | 240 |
| ctgggtgaaa | agtatcaact | gaagcagttt | cattttcaca | cgccgagcga | gcataccatc | 300 |
| gagaagaagt | cgtacccgtt | ggaaatccac | ttcgttcaca | aaaccgagga | tggtaaaatc | 360 |
| ttggtcgtgg | gtgtgatggc | caaactgggt | aagacgaata | agagctggaa | caagattctg | 420 |
| aacgtggctc | cggcggaaga | aggtgaaaag | atcctggaca | aaaacctgaa | cctgaacaac | 480 |
| ctgattccga | agataaaacg | ttatatgacg | tacagcggca | gcctgaccac | cccaccgtgt | 540 |

```
cttgaaggcg ttcgttggat cgttctgaag aagccgatca gcattagcaa acagcagttg    600
gagaaactga aaagcgtcat ggtcaacccg aataatcgcc cggttcaaga aatcaattcc    660
cgttggatta ttgagggctt ctaa                                           684
```

<210> SEQ ID NO 114
<211> LENGTH: 227
<212> TYPE: PRT
<213> ORGANISM: Artificial sequence
<220> FEATURE:
<223> OTHER INFORMATION: Variant: T181L

<400> SEQUENCE: 114

```
Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Leu Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225
```

<210> SEQ ID NO 115
<211> LENGTH: 684
<212> TYPE: DNA
<213> ORGANISM: Artificial sequence
<220> FEATURE:
<223> OTHER INFORMATION: Variant: T181Q

<400> SEQUENCE: 115

```
atggaacacg aatggagcta cgaaggtgag aagggtcctg agcattgggc gcagttgaaa    60
ccggagttct tttggtgcaa gctgaagaat caatctccga tcaacattga caagaagtac   120
aaagtcaaag cgaatctgcc gaagctgaat ctgtattaca aaaccgcaaa agagagcgag   180
gttgtgaaca atggccacac tattcaaatc aacattaaag aggataacac cctgaattat   240
```

```
ctgggtgaaa agtatcaact gaagcagttt cattttcaca cgccgagcga gcataccatc    300
gagaagaagt cgtacccgtt ggaaatccac ttcgttcaca aaaccgagga tggtaaaatc    360
ttggtcgtgg gtgtgatggc caaactgggt aagacgaata aagagctgga caagattctg    420
aacgtggctc cggcggaaga aggtgaaaag atcctggaca aaaacctgaa cctgaacaac    480
ctgattccga agataaacg ttatatgacg tacagcggca gcctgaccac cccaccgtgt     540
caggaaggcg ttcgttggat cgttctgaag aagccgatca gcattagcaa acagcagttg    600
gagaaactga aagcgtcat ggtcaacccg aataatcgcc cggttcaaga aatcaattcc     660
cgttggatta ttgagggctt ctaa                                           684
```

<210> SEQ ID NO 116
<211> LENGTH: 227
<212> TYPE: PRT
<213> ORGANISM: Artificial sequence
<220> FEATURE:
<223> OTHER INFORMATION: Variant: T181Q

<400> SEQUENCE: 116

```
Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Gln Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225
```

<210> SEQ ID NO 117
<211> LENGTH: 684
<212> TYPE: DNA
<213> ORGANISM: Artificial sequence
<220> FEATURE:
<223> OTHER INFORMATION: Variant: T181R -continued

<400> SEQUENCE: 117

```
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaccgcaaa agagagcgag      180
gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaaccgagga tggtaaaatc     360
ttggtcgtgg gtgtgatggc caaactgggt aagacgaata aagagctgga caagattctg     420
aacgtggctc cggcggaaga aggtgaaaag atcctggaca aaacctgaa cctgaacaac      480
ctgattccga agataaacg ttatatgacg tacagcggca gcctgaccac cccaccgtgt      540
cgtgaaggcg ttcgttggat cgttctgaag aagccgatca gcattagcaa acagcagttg     600
gagaaactga aagcgtcat ggtcaacccg aataatcgcc cggttcaaga aatcaattcc      660
cgttggatta ttgagggctt ctaa                                            684
```

<210> SEQ ID NO 118
<211> LENGTH: 227
<212> TYPE: PRT
<213> ORGANISM: Artificial sequence
<220> FEATURE:
<223> OTHER INFORMATION: Variant: T181R

<400> SEQUENCE: 118

```
Met Glu His Glu Trp Ser Tyr Glu Gly Glu Lys Gly Pro Glu His Trp
1               5                   10                  15
Ala Gln Leu Lys Pro Glu Phe Phe Trp Cys Lys Leu Lys Asn Gln Ser
            20                  25                  30
Pro Ile Asn Ile Asp Lys Lys Tyr Lys Val Lys Ala Asn Leu Pro Lys
        35                  40                  45
Leu Asn Leu Tyr Tyr Lys Thr Ala Lys Glu Ser Glu Val Val Asn Asn
    50                  55                  60
Gly His Thr Ile Gln Ile Asn Ile Lys Glu Asp Asn Thr Leu Asn Tyr
65                  70                  75                  80
Leu Gly Glu Lys Tyr Gln Leu Lys Gln Phe His Phe His Thr Pro Ser
                85                  90                  95
Glu His Thr Ile Glu Lys Lys Ser Tyr Pro Leu Glu Ile His Phe Val
            100                 105                 110
His Lys Thr Glu Asp Gly Lys Ile Leu Val Val Gly Val Met Ala Lys
        115                 120                 125
Leu Gly Lys Thr Asn Lys Glu Leu Asp Lys Ile Leu Asn Val Ala Pro
    130                 135                 140
Ala Glu Glu Gly Glu Lys Ile Leu Asp Lys Asn Leu Asn Leu Asn Asn
145                 150                 155                 160
Leu Ile Pro Lys Asp Lys Arg Tyr Met Thr Tyr Ser Gly Ser Leu Thr
                165                 170                 175
Thr Pro Pro Cys Arg Glu Gly Val Arg Trp Ile Val Leu Lys Lys Pro
            180                 185                 190
Ile Ser Ile Ser Lys Gln Gln Leu Glu Lys Leu Lys Ser Val Met Val
        195                 200                 205
Asn Pro Asn Asn Arg Pro Val Gln Glu Ile Asn Ser Arg Trp Ile Ile
    210                 215                 220
Glu Gly Phe
225
```

<210> SEQ ID NO 119
<211> LENGTH: 684
<212> TYPE: DNA
<213> ORGANISM: Artificial sequence
<220> FEATURE:
<223> OTHER INFORMATION: Variant: S205C

<400> SEQUENCE: 119

```
atggaacacg aatggagcta cgaaggtgag aagggtcctg agcattgggc gcagttgaaa      60
ccggagttct tttggtgcaa gctgaagaat caatctccga tcaacattga caagaagtac    120
aaagtcaaag cgaatctgcc gaagctgaat ctgtattaca aaccgcaaa agagagcgag     180
gttgtgaaca atggccacac tattcaaatc aacattaaag aggataacac cctgaattat    240
ctgggtgaaa agtatcaact gaagcagttt cattttcaca cgccgagcga gcataccatc    300
gagaagaagt cgtacccgtt ggaaatccac ttcgttcaca aaccgagga tggtaaaatc     360
ttggtcgtgg gtgtgatggc caaactgggt aagacgaata aagagctgga caagattctg    420
aacgtggctc cggcggaaga aggtgaaaag atcctggaca aaaacctgaa cctgaacaac    480
ctgattccga agataaacg ttatatgacg tacagcggca gcctgaccac cccaccgtgt     540
acggaaggcg ttcgttggat cgttctgaag aagccgatca gcattagcaa acagcagttg    600
gagaaactga atgtgtcat ggtcaacccg aataatcgcc cggttcaaga aatcaattcc     660
cgttggatta ttgagggctt ctaa                                            684
```

<210> SEQ ID NO 120
<211> LENGTH: 227
<212> TYPE: PRT
<213> ORGANISM: Artificial sequence
<220> FEATURE:
<223> OTHER INFORMATION: Variant: S205C

<400> SEQUENCE: 120

```
Met Glu His Glu Trp Ser Tyr Glu Gly Glu Lys Gly Pro Glu His Trp
1               5                   10                  15
Ala Gln Leu Lys Pro Glu Phe Phe Trp Cys Lys Leu Lys Asn Gln Ser
            20                  25                  30
Pro Ile Asn Ile Asp Lys Lys Tyr Lys Val Lys Ala Asn Leu Pro Lys
        35                  40                  45
Leu Asn Leu Tyr Tyr Lys Thr Ala Lys Glu Ser Glu Val Val Asn Asn
    50                  55                  60
Gly His Thr Ile Gln Ile Asn Ile Lys Glu Asp Asn Thr Leu Asn Tyr
65                  70                  75                  80
Leu Gly Glu Lys Tyr Gln Leu Lys Gln Phe His Phe His Thr Pro Ser
                85                  90                  95
Glu His Thr Ile Glu Lys Lys Ser Tyr Pro Leu Glu Ile His Phe Val
            100                 105                 110
His Lys Thr Glu Asp Gly Lys Ile Leu Val Val Gly Val Met Ala Lys
        115                 120                 125
Leu Gly Lys Thr Asn Lys Glu Leu Asp Lys Ile Leu Asn Val Ala Pro
    130                 135                 140
Ala Glu Glu Gly Glu Lys Ile Leu Asp Lys Asn Leu Asn Leu Asn Asn
145                 150                 155                 160
Leu Ile Pro Lys Asp Lys Arg Tyr Met Thr Tyr Ser Gly Ser Leu Thr
                165                 170                 175
```

Thr Pro Pro Cys Thr Glu Gly Val Arg Trp Ile Val Leu Lys Lys Pro
         180                 185                 190

Ile Ser Ile Ser Lys Gln Gln Leu Glu Lys Leu Lys Cys Val Met Val
         195                 200                 205

Asn Pro Asn Asn Arg Pro Val Gln Glu Ile Asn Ser Arg Trp Ile Ile
         210                 215                 220

Glu Gly Phe
225

<210> SEQ ID NO 121
<211> LENGTH: 684
<212> TYPE: DNA
<213> ORGANISM: Artificial sequence
<220> FEATURE:
<223> OTHER INFORMATION: Variant: Q18T-K20A

<400> SEQUENCE: 121
atggaacacg aatggagcta cgaaggtgag aagggtcctg agcattgggc gactttggct    60
ccggagttct tttggtgcaa gctgaagaat caatctccga tcaacattga caagaagtac   120
aaagtcaaag cgaatctgcc gaagctgaat ctgtattaca aaccgcaaa agagagcgag    180 gttgtgaaca atggccacac tattcaaatc aacattaaag aggataacac cctgaattat   240
ctgggtgaaa agtatcaact gaagcagttt cattttcaca cgccgagcga gcataccatc   300
gagaagaagt cgtacccgtt ggaaatccac ttcgttcaca aaaccgagga tggtaaaatc   360
ttggtcgtgg gtgtgatggc caaactgggt aagacgaata agagctgga caagattctg    420 aacgtggctc cggcggaaga aggtgaaaag atcctggaca aaaacctgaa cctgaacaac   480
ctgattccga agataaacg ttatatgacg tacagcggca gcctgaccac cccaccgtgt    540
acggaaggcg ttcgttggat cgttctgaag aagccgatca gcattagcaa acagcagttg   600
gagaaactga aagcgtcat ggtcaacccg aataatcgcc cggttcaaga aatcaattcc    660
cgttggatta ttgagggctt ctaa                                          684

<210> SEQ ID NO 122
<211> LENGTH: 227
<212> TYPE: PRT
<213> ORGANISM: Artificial sequence
<220> FEATURE:
<223> OTHER INFORMATION: Variant: Q18T-K20A

<400> SEQUENCE: 122

Met Glu His Glu Trp Ser Tyr Glu Gly Glu Lys Gly Pro Glu His Trp
1               5                  10                  15

Ala Thr Leu Ala Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

```
Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225
```

<210> SEQ ID NO 123
<211> LENGTH: 684
<212> TYPE: DNA
<213> ORGANISM: Artificial sequence
<220> FEATURE:
<223> OTHER INFORMATION: Variant: Q18R-K20A

<400> SEQUENCE: 123

```
atggaacacg aatggagcta cgaaggtgag aagggtcctg agcattgggc gcgtttggct    60
ccggagttct tttggtgcaa gctgaagaat caatctccga tcaacattga caagaagtac   120
aaagtcaaag cgaatctgcc gaagctgaat ctgtattaca aaccgcaaa agagagcgag   180
gttgtgaaca atggccacac tattcaaatc aacattaaag aggataacac cctgaattat   240
ctgggtgaaa agtatcaact gaagcagttt cattttcaca cgccgagcga gcataccatc   300
gagaagaagt cgtacccgtt ggaaatccac ttcgttcaca aaccgagga tggtaaaatc   360
ttggtcgtgg gtgtgatggc caaactgggt aagacgaata agagctgga caagattctg   420
aacgtggctc cggcggaaga aggtgaaaag atcctggaca aaaacctgaa cctgaacaac   480
ctgattccga agataaaacg ttatatgacg tacagcggca gcctgaccac cccaccgtgt   540
acggaaggcg ttcgttggat cgttctgaag aagccgatca gcattagcaa acagcagttg   600
gagaaactga aaagcgtcat ggtcaacccg aataatcgcc ggttcaaga aatcaattcc   660
cgttggatta ttgagggctt ctaa                                         684
```

<210> SEQ ID NO 124
<211> LENGTH: 227
<212> TYPE: PRT
<213> ORGANISM: Artificial sequence
<220> FEATURE:
<223> OTHER INFORMATION: Variant: Q18R-K20A

<400> SEQUENCE: 124

```
Met Glu His Glu Trp Ser Tyr Glu Gly Glu Lys Gly Pro Glu His Trp
1               5                   10                  15

Ala Arg Leu Ala Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
```

```
                65                  70                  75                  80
Leu Gly Glu Lys Tyr Gln Leu Lys Gln Phe His Phe His Thr Pro Ser
                    85                  90                  95
Glu His Thr Ile Glu Lys Lys Ser Tyr Pro Leu Glu Ile His Phe Val
                100                 105                 110
His Lys Thr Glu Asp Gly Lys Ile Leu Val Val Gly Val Met Ala Lys
            115                 120                 125
Leu Gly Lys Thr Asn Lys Glu Leu Asp Lys Ile Leu Asn Val Ala Pro
        130                 135                 140
Ala Glu Glu Gly Glu Lys Ile Leu Asp Lys Asn Leu Asn Leu Asn Asn
145                 150                 155                 160
Leu Ile Pro Lys Asp Lys Arg Tyr Met Thr Tyr Ser Gly Ser Leu Thr
                165                 170                 175
Thr Pro Pro Cys Thr Glu Gly Val Arg Trp Ile Val Leu Lys Lys Pro
                180                 185                 190
Ile Ser Ile Ser Lys Gln Gln Leu Gly Lys Leu Lys Ser Val Met Val
                195                 200                 205
Asn Pro Asn Asn Arg Pro Val Gln Glu Ile Asn Ser Arg Trp Ile Ile
    210                 215                 220
Glu Gly Phe
225
```

```
<210> SEQ ID NO 125
<211> LENGTH: 684
<212> TYPE: DNA
<213> ORGANISM: Artificial sequence
<220> FEATURE:
<223> OTHER INFORMATION: Variant: E2K-T181M-K197I

<400> SEQUENCE: 125
atgaagcacg aatggagcta cgaaggtgag aagggtcctg agcattgggc gcagttgaaa     60
ccggagttct tttggtgcaa gctgaagaat caatctccga tcaacattga caagaagtac    120
aaagtcaaag cgaatctgcc gaagctgaat ctgtattaca aaccgcaaa agagagcgag    180
gttgtgaaca tggccacac tattcaaatc aacattaaag aggataacac cctgaattat    240
ctgggtgaaa agtatcaact gaagcagttt cattttcaca cgccgagcga gcataccatc    300
gagaagaagt cgtacccgtt ggaaatccac ttcgttcaca aaaccgagga tggtaaaatc    360
ttggtcgtgg gtgtgatggc caaactgggt aagacgaata agagctgga caagattctg    420
aacgtggctc cggcggaaga aggtgaaaag atcctggaca aaaacctgaa cctgaacaac    480
ctgattccga agataaacg ttatatgacg tacagcggca gcctgaccac cccaccgtgt    540
atggaaggcg ttcgttggat cgttctgaag aagccgatca gcattagcat ccagcagttg    600
gagaaactga aagcgtcat ggtcaacccg aataatcgcc cggttcaaga aatcaattcc    660
cgttggatta ttgagggctt ctaa                                           684
```

```
<210> SEQ ID NO 126
<211> LENGTH: 227
<212> TYPE: PRT
<213> ORGANISM: Artificial sequence
<220> FEATURE:
<223> OTHER INFORMATION: Variant: E2K-T181M-K197I

<400> SEQUENCE: 126

Met Lys His Glu Trp Ser Tyr Glu Gly Glu Lys Gly Pro Glu His Trp
1               5                   10                  15
```

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
 50                  55                  60

Gly His Thr Ile Gln Ile Asn Ile Lys Glu Asp Asn Thr Leu Asn Tyr
 65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
            115                 120                 125

Leu Gly Lys Thr Asn Lys Glu Leu Asp Lys Ile Leu Asn Val Ala Pro
130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Met Glu Gly Val Arg Trp Ile Val Leu Lys Lys Pro
            180                 185                 190

Ile Ser Ile Ser Ile Gln Gln Leu Glu Lys Leu Lys Ser Val Met Val
            195                 200                 205

Asn Pro Asn Asn Arg Pro Val Gln Glu Ile Asn Ser Arg Trp Ile Ile
            210                 215                 220

Glu Gly Phe
225

<210> SEQ ID NO 127
<211> LENGTH: 684
<212> TYPE: DNA
<213> ORGANISM: Artificial sequence
<220> FEATURE:
<223> OTHER INFORMATION: Variant: E14D-Q18R

<400> SEQUENCE: 127
atggaacacg aatggagcta cgaaggtgag aagggtcctg atcattgggc gcgtttgaaa      60
ccggagttct tttggtgcaa gctgaagaat caatctccga tcaacattga caagaagtac     120
aaagtcaaag cgaatctgcc gaagctgaat ctgtattaca aaccgcaaa agagagcgag      180 gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaccgagga tggtaaaatc      360 ttggtcgtgg gtgtgatggc caaactgggt aagacgaata agagctgga caagattctg      420 aacgtggctc cggcggaaga aggtgaaaag atcctggaca aaacctgaa cctgaacaac      480 ctgattccga agataaacg ttatatgacg tacagcggca gcctgaccac cccaccgtgt     540
acggaaggcg ttcgttggat cgttctgaag aagccgatca gcattagcaa acagcagttg     600
gagaaactga aaagcgtcat ggtcaacccg aataatcgcc cggttcaaga aatcaattcc     660
cgttggatta ttgagggctt ctaa                                            684

<210> SEQ ID NO 128
<211> LENGTH: 227

```
<212> TYPE: PRT
<213> ORGANISM: Artificial sequence
<220> FEATURE:
<223> OTHER INFORMATION: Variant: E14D-Q18R

<400> SEQUENCE: 128

Met Glu His Glu Trp Ser Tyr Glu Gly Glu Lys Gly Pro Asp His Trp
1               5                   10                  15

Ala Arg Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Gly Lys Leu Lys Ser Val Met Val
        195                 200                 205

Asn Pro Asn Asn Arg Pro Val Gln Glu Ile Asn Ser Arg Trp Ile Ile
210                 215                 220

Glu Gly Phe
225

<210> SEQ ID NO 129
<211> LENGTH: 684
<212> TYPE: DNA
<213> ORGANISM: Artificial sequence
<220> FEATURE:
<223> OTHER INFORMATION: Variant: Y52C-V122I-K150N-G226S

<400> SEQUENCE: 129
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtgttaca aaccgcaaa agagagcgag      180 gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaaccgagga tggtaaaatc     360
ttgatcgtgg gtgtgatggc caaactgggt aagacgaata agagctggac aagattctg      420 aacgtggctc cggcggaaga aggtgaaaat atcctggaca aaaacctgaa cctgaacaac     480
ctgattccga agataaaacg ttatatgacg tacagcggca gcctgaccac cccaccgtgt     540
```

```
acggaaggcg ttcgttggat cgttctgaag aagccgatca gcattagcaa acagcagttg    600
gagaaactga aaagcgtcat ggtcaacccg aataatcgcc cggttcaaga aatcaattcc    660
cgttggatta ttgagtcttt ctaa                                           684
```

<210> SEQ ID NO 130
<211> LENGTH: 227
<212> TYPE: PRT
<213> ORGANISM: Artificial sequence
<220> FEATURE:
<223> OTHER INFORMATION: Variant: Y52C-V122I-K150N-G226S

<400> SEQUENCE: 130

```
Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Cys Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Ile Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Asn Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Ser Phe
225
```

<210> SEQ ID NO 131
<211> LENGTH: 684
<212> TYPE: DNA
<213> ORGANISM: Artificial sequence
<220> FEATURE:
<223> OTHER INFORMATION: Variant: G65S-K150I

<400> SEQUENCE: 131

```
atggaacacg aatggagcta cgaaggtgag aagggtcctg agcattgggc gcagttgaaa    60
ccggagttct tttggtgcaa gctgaagaat caatctccga tcaacattga caagaagtac    120
aaagtcaaag cgaatctgcc gaagctgaat ctgtattaca aaccgcaaa agagagcgag    180 gttgtgaaca attctcacac tattcaaatc aacattaaag aggataacac cctgaattat    240
```

```
ctgggtgaaa agtatcaact gaagcagttt cattttcaca cgccgagcga gcataccatc      300
gagaagaagt cgtacccgtt ggaaatccac ttcgttcaca aaaccgagga tggtaaaatc      360
ttggtcgtgg gtgtgatggc caaactgggt aagacgaata agagctgga caagattctg       420 aacgtggctc cggcggaaga aggtgaaatc atcctggaca aaaacctgaa cctgaacaac      480
ctgattccga agataaacg ttatatgacg tacagcggca gcctgaccac cccaccgtgt       540
acggaaggcg ttcgttggat cgttctgaag aagccgatca gcattagcaa acagcagttg      600
gagaaactga aaagcgtcat ggtcaacccg aataatcgcc cggttcaaga aatcaattcc     660
cgttggatta ttgagggctt ctaa                                              684
```

<210> SEQ ID NO 132
<211> LENGTH: 227
<212> TYPE: PRT
<213> ORGANISM: Artificial sequence
<220> FEATURE:
<223> OTHER INFORMATION: Variant: G65S-K150I

<400> SEQUENCE: 132

```
Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Ser His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Ile Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225
```

<210> SEQ ID NO 133
<211> LENGTH: 684
<212> TYPE: DNA
<213> ORGANISM: Artificial sequence
<220> FEATURE:
<223> OTHER INFORMATION: Variant: K57R-G130C

<400> SEQUENCE: 133

```
atggaacacg aatggagcta cgaaggtgag aagggtcctg agcattgggc gcagttgaaa      60
ccggagttct tttggtgcaa gctgaagaat caatctccga tcaacattga caagaagtac    120
aaagtcaaag cgaatctgcc gaagctgaat ctgtattaca aaccgcacg tgagagcgag     180
gttgtgaaca atggccacac tattcaaatc aacattaaag aggataacac cctgaattat    240
ctgggtgaaa agtatcaact gaagcagttt cattttcaca cgccgagcga gcataccatc    300
gagaagaagt cgtacccgtt ggaaatccac ttcgttcaca aaccgagga tggtaaaatc     360
ttggtcgtgg gtgtgatggc caaactgtgt aagacgaata agagctgga caagattctg     420
aacgtggctc cggcggaaga aggtgaaaag atcctggaca aaaacctgaa cctgaacaac    480
ctgattccga agataaacg ttatatgacg tacagcggca gcctgaccac cccaccgtgt     540
acggaaggcg ttcgttggat cgttctgaag aagccgatca gcattagcaa acagcagttg    600
gagaaactga aaagcgtcat ggtcaacccg aataatcgcc cggttcaaga aatcaattcc    660
cgttggatta ttgagggctt ctaa                                            684
```

<210> SEQ ID NO 134
<211> LENGTH: 227
<212> TYPE: PRT
<213> ORGANISM: Artificial sequence
<220> FEATURE:
<223> OTHER INFORMATION: Variant: K57R-G130C

<400> SEQUENCE: 134

```
Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Arg Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Cys Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220
```

-continued

Glu Gly Phe
225

<210> SEQ ID NO 135
<211> LENGTH: 684
<212> TYPE: DNA
<213> ORGANISM: Artificial sequence
<220> FEATURE:
<223> OTHER INFORMATION: Variant: G82C-K88E

<400> SEQUENCE: 135

```
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaccgcaaa agagagcgag     180
gttgtgaaca atggccacac tattcaaatc aacattaaag aggataacac cctgaattat     240
ctgtgtgaaa agtatcaact ggagcagttt cattttcaca cgccgagcga gcataccatc     300
gagaagaagt cgtacccgtt ggaaatccac ttcgttcaca aaaccgagga tggtaaaatc     360
ttggtcgtgg gtgtgatggc caaactgggt aagacgaata agagctgga caagattctg     420
aacgtggctc cggcggaaga aggtgaaaag atcctggaca aaaacctgaa cctgaacaac     480
ctgattccga agataaacg ttatatgacg tacagcggca gcctgaccac cccaccgtgt     540
acggaaggcg ttcgttggat cgttctgaag aagccgatca gcattagcaa acagcagttg     600
gagaaactga aaagcgtcat ggtcaacccg aataatcgcc cggttcaaga aatcaattcc     660
cgttggatta ttgagggctt ctaa                                            684
```

<210> SEQ ID NO 136
<211> LENGTH: 227
<212> TYPE: PRT
<213> ORGANISM: Artificial sequence
<220> FEATURE:
<223> OTHER INFORMATION: Variant: G82C-K88E

<400> SEQUENCE: 136

```
Met Glu His Glu Trp Ser Tyr Glu Gly Glu Lys Gly Pro Glu His Trp
1               5                   10                  15
Ala Gln Leu Lys Pro Glu Phe Phe Trp Cys Lys Leu Lys Asn Gln Ser
            20                  25                  30
Pro Ile Asn Ile Asp Lys Lys Tyr Lys Val Lys Ala Asn Leu Pro Lys
        35                  40                  45
Leu Asn Leu Tyr Tyr Lys Thr Ala Lys Glu Ser Glu Val Val Asn Asn
    50                  55                  60
Gly His Thr Ile Gln Ile Asn Ile Lys Glu Asp Asn Thr Leu Asn Tyr
65                  70                  75                  80
Leu Cys Glu Lys Tyr Gln Leu Glu Gln Phe His Phe His Thr Pro Ser
                85                  90                  95
Glu His Thr Ile Glu Lys Lys Ser Tyr Pro Leu Glu Ile His Phe Val
            100                 105                 110
His Lys Thr Glu Asp Gly Lys Ile Leu Val Val Gly Val Met Ala Lys
        115                 120                 125
Leu Gly Lys Thr Asn Lys Glu Leu Asp Lys Ile Leu Asn Val Ala Pro
    130                 135                 140
Ala Glu Glu Gly Glu Lys Ile Leu Asp Lys Asn Leu Asn Leu Asn Asn
145                 150                 155                 160
Leu Ile Pro Lys Asp Lys Arg Tyr Met Thr Tyr Ser Gly Ser Leu Thr
                165                 170                 175
```

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
210                 215                 220

Glu Gly Phe
225

<210> SEQ ID NO 137
<211> LENGTH: 684
<212> TYPE: DNA
<213> ORGANISM: Artificial sequence
<220> FEATURE:
<223> OTHER INFORMATION: Variant: G82C-G148A

<400> SEQUENCE: 137
atggaacacg aatggagcta cgaaggtgag aagggtcctg agcattgggc gcagttgaaa      60
ccggagttct tttggtgcaa gctgaagaat caatctccga tcaacattga caagaagtac    120
aaagtcaaag cgaatctgcc gaagctgaat ctgtattaca aaccgcaaa agagagcgag     180 gttgtgaaca atggccacac tattcaaatc aacattaaag aggataacac cctgaattat    240
ctgtgtgaaa agtatcaact gaagcagttt cattttcaca cgccgagcga gcataccatc    300
gagaagaagt cgtacccgtt ggaaatccac ttcgttcaca aaccgagga tggtaaaatc     360 ttggtcgtgg gtgtgatggc caaactgggt aagacgaata agagctgga caagattctg     420 aacgtggctc cggcggaaga gctgaaaag atcctggaca aaaacctgaa cctgaacaac     480
ctgattccga agataaacg ttatatgacg tacagcggca gcctgaccac cccaccgtgt     540
acggaaggcg ttcgttggat cgttctgaag aagccgatca gcattagcaa acagcagttg    600
gagaaactga aagcgtcat ggtcaacccg aataatcgcc cggttcaaga aatcaattcc     660
cgttggatta ttgagggctt ctaa                                              684

<210> SEQ ID NO 138
<211> LENGTH: 227
<212> TYPE: PRT
<213> ORGANISM: Artificial sequence
<220> FEATURE:
<223> OTHER INFORMATION: Variant: G82C-G148A

<400> SEQUENCE: 138

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Cys Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys

|  |  |  | 115 |  |  |  | 120 |  |  |  | 125 |  |  |  |

| Leu | Gly | Lys | Thr | Asn | Lys | Glu | Leu | Asp | Lys | Ile | Leu | Asn | Val | Ala | Pro |
|---|---|---|---|---|---|---|---|---|---|---|---|---|---|---|---|
|  |  |  | 130 |  |  |  | 135 |  |  |  | 140 |  |  |  |  |

Ala Glu Glu Ala Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225

<210> SEQ ID NO 139
<211> LENGTH: 684
<212> TYPE: DNA
<213> ORGANISM: Artificial sequence
<220> FEATURE:
<223> OTHER INFORMATION: Variant: M126L-G130L

<400> SEQUENCE: 139

```
atggaacacg aatggagcta cgaaggtgag aagggtcctg agcattgggc gcagttgaaa    60
ccggagttct tttggtgcaa gctgaagaat caatctccga tcaacattga caagaagtac   120
aaagtcaaag cgaatctgcc gaagctgaat ctgtattaca aaccgcaaa agagagcgag   180
gttgtgaaca atggccacac tattcaaatc aacattaaag aggataacac cctgaattat   240
ctgggtgaaa agtatcaact gaagcagttt cattttcaca cgccgagcga gcataccatc   300
gagaagaagt cgtacccgtt ggaaatccac ttcgttcaca aaaccgagga tggtaaaatc   360
ttggtcgtgg gtgtgcttgc caaactgctt aagacgaata agagctgga caagattctg   420
aacgtggctc cggcggaaga aggtgaaaag atcctggaca aaaacctgaa cctgaacaac   480
ctgattccga agataaacg ttatatgacg tacagcggca gcctgaccac cccaccgtgt   540
acggaaggcg ttcgttggat cgttctgaag aagccgatca gcattagcaa acagcagttg   600
gagaaactga aaagcgtcat ggtcaacccg aataatcgcc cggttcaaga aatcaattcc   660
cgttggatta ttgagggctt ctaa                                            684
```

<210> SEQ ID NO 140
<211> LENGTH: 227
<212> TYPE: PRT
<213> ORGANISM: Artificial sequence
<220> FEATURE:
<223> OTHER INFORMATION: Variant: M126L-G130L

<400> SEQUENCE: 140

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
 65                  70                  75                  80

Leu Gly Glu Lys Tyr Gln Leu Lys Gln Phe His Phe His Thr Pro Ser
             85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Leu Ala Lys
        115                 120                 125

Leu Leu Lys Thr Asn Lys Glu Leu Asp Lys Ile Leu Asn Val Ala Pro
130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Leu Glu Lys Leu Lys Ser Val Met Val
        195                 200                 205

Asn Pro Asn Asn Arg Pro Val Gln Glu Ile Asn Ser Arg Trp Ile Ile
210                 215                 220

Glu Gly Phe
225

<210> SEQ ID NO 141
<211> LENGTH: 684
<212> TYPE: DNA
<213> ORGANISM: Artificial sequence
<220> FEATURE:
<223> OTHER INFORMATION: Variant: G82C-I100V

<400> SEQUENCE: 141
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaccgcaaa agagagcgag     180 gttgtgaaca atggccacac tattcaaatc aacattaaag aggataacac cctgaattat     240
ctgtgtgaaa agtatcaact gaagcagttt cattttcaca cgccgagcga agcataccgtt    300 gagaagaagt cgtacccgtt ggaaatccac ttcgttcaca aaaccgagga tggtaaaatc     360
ttggtcgtgg gtgtgatggc caaactgggt aagacgaata agagctgga caagattctg      420 aacgtggctc cggcggaaga aggtgaaaag atcctggaca aaaacctgaa cctgaacaac     480
ctgattccga agataaaacg ttatatgacg tacagcggca gcctgaccac cccaccgtgt     540
acggaaggcg ttcgttggat cgttctgaag aagccgatca gcattagcaa acagcagttg     600
gagaaactga aagcgtcat ggtcaacccg aataatcgcc cggttcaaga aatcaattcc     660
cgttggatta ttgagggctt ctaa                                            684

<210> SEQ ID NO 142
<211> LENGTH: 227
<212> TYPE: PRT
<213> ORGANISM: Artificial sequence
<220> FEATURE:
<223> OTHER INFORMATION: Variant: G82C-I100V

<400> SEQUENCE: 142

Met Glu His Glu Trp Ser Tyr Glu Gly Glu Lys Gly Pro Glu His Trp
 1               5                  10                  15

```
Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
 50                  55                  60

Gly His Thr Ile Gln Ile Asn Ile Lys Glu Asp Asn Thr Leu Asn Tyr
 65                  70                  75                  80

Leu Cys Glu Lys Tyr Gln Leu Lys Gln Phe His Phe His Thr Pro Ser
                85                  90                  95

Glu His Thr Val Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Gly Lys Leu Lys Ser Val Met Val
        195                 200                 205

Asn Pro Asn Asn Arg Pro Val Gln Glu Ile Asn Ser Arg Trp Ile Ile
210                 215                 220

Glu Gly Phe
225

<210> SEQ ID NO 143
<211> LENGTH: 684
<212> TYPE: DNA
<213> ORGANISM: Artificial sequence
<220> FEATURE:
<223> OTHER INFORMATION: Variant: K38C-G82C-I100V

<400> SEQUENCE: 143
atggaacacg aatggagcta cgaaggtgag aagggtcctg agcattgggc gcagttgaaa      60
ccggagttct tttggtgcaa gctgaagaat caatctccga tcaacattga ctgtaagtac     120
aaagtcaaag cgaatctgcc gaagctgaat ctgtattaca aaccgcaaa agagagcgag      180 gttgtgaaca atggccacac tattcaaatc aacattaaag aggataacac cctgaattat     240
ctgtgtgaaa agtatcaact gaagcagttt cattttcaca cgccgagcga gcataccgtt     300
gagaagaagt cgtacccgtt ggaaatccac ttcgttcaca aaccgagga tggtaaaatc      360 ttggtcgtgg gtgtgatggc caaactgggt aagacgaata agagctgga caagattctg      420 aacgtggctc cggcggaaga aggtgaaaag atcctggaca aaaacctgaa cctgaacaac     480
ctgattccga agataaacg ttatatgacg tacagcggca gcctgaccac cccaccgtgt     540
acggaaggcg ttcgttggat cgttctgaag aagccgatca gcattagcaa acagcagttg     600
gagaaactga aaagcgtcat ggtcaacccg aataatcgcc cggttcaaga aatcaattcc     660
cgttggatta ttgagggctt ctaa                                           684

<210> SEQ ID NO 144
```

<211> LENGTH: 227
<212> TYPE: PRT
<213> ORGANISM: Artificial sequence
<220> FEATURE:
<223> OTHER INFORMATION: Variant: K38C-G82C-I100V

<400> SEQUENCE: 144

```
Met Glu His Glu Trp Ser Tyr Glu Gly Glu Lys Gly Pro Glu His Trp
 1               5                  10                  15
Ala Gln Leu Lys Pro Glu Phe Phe Trp Cys Lys Leu Lys Asn Gln Ser
            20                  25                  30
Pro Ile Asn Ile Asp Cys Lys Tyr Lys Val Lys Ala Asn Leu Pro Lys
        35                  40                  45
Leu Asn Leu Tyr Tyr Lys Thr Ala Lys Glu Ser Glu Val Val Asn Asn
    50                  55                  60
Gly His Thr Ile Gln Ile Asn Ile Lys Glu Asp Asn Thr Leu Asn Tyr
65                  70                  75                  80
Leu Cys Glu Lys Tyr Gln Leu Lys Gln Phe His Phe His Thr Pro Ser
                85                  90                  95
Glu His Thr Val Glu Lys Lys Ser Tyr Pro Leu Glu Ile His Phe Val
            100                 105                 110
His Lys Thr Glu Asp Gly Lys Ile Leu Val Val Gly Val Met Ala Lys
        115                 120                 125
Leu Gly Lys Thr Asn Lys Glu Leu Asp Lys Ile Leu Asn Val Ala Pro
    130                 135                 140
Ala Glu Glu Gly Glu Lys Ile Leu Asp Lys Asn Leu Asn Leu Asn Asn
145                 150                 155                 160
Leu Ile Pro Lys Asp Lys Arg Tyr Met Thr Tyr Ser Gly Ser Leu Thr
                165                 170                 175
Thr Pro Pro Cys Thr Glu Gly Val Arg Trp Ile Val Leu Lys Lys Pro
            180                 185                 190
Ile Ser Ile Ser Lys Gln Gln Leu Glu Lys Leu Lys Ser Val Met Val
        195                 200                 205
Asn Pro Asn Asn Arg Pro Val Gln Glu Ile Asn Ser Arg Trp Ile Ile
    210                 215                 220
Glu Gly Phe
225
```

<210> SEQ ID NO 145
<211> LENGTH: 684
<212> TYPE: DNA
<213> ORGANISM: Artificial sequence
<220> FEATURE:
<223> OTHER INFORMATION: Variant: K38G-G82C-I100V

<400> SEQUENCE: 145

```
atggaacacg aatggagcta cgaaggtgag aagggtcctg agcattgggc gcagttgaaa      60
ccggagttct tttggtgcaa gctgaagaat caatctccga tcaacattga cggtaagtac     120
aaagtcaaag cgaatctgcc gaagctgaat ctgtattaca aaccgcaaa agagagcgag     180
gttgtgaaca atggccacac tattcaaatc aacattaaag aggataacac cctgaattat     240
ctgtgtgaaa agtatcaact gaagcagttt cattttcaca cgccgagcga agcataccgtt   300
gagaagaagt cgtacccgtt ggaaatccac ttcgttcaca aaccgagga tggtaaaatc     360
ttggtcgtgg gtgtgatggc caaactgggt aagacgaata agagctgga caagattctg     420
aacgtggctc cggcggaaga aggtgaaaag atcctggaca aaaacctgaa cctgaacaac     480
```

```
ctgattccga aagataaacg ttatatgacg tacagcggca gcctgaccac cccaccgtgt    540
acggaaggcg ttcgttggat cgttctgaag aagccgatca gcattagcaa acagcagttg    600
gagaaactga aaagcgtcat ggtcaacccg aataatcgcc cggttcaaga aatcaattcc    660
cgttggatta ttgagggctt ctaa                                            684
```

<210> SEQ ID NO 146
<211> LENGTH: 227
<212> TYPE: PRT
<213> ORGANISM: Artificial sequence
<220> FEATURE:
<223> OTHER INFORMATION: Variant: K38G-G82C-I100V

<400> SEQUENCE: 146

```
Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Gly Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Cys Glu Lys Tyr Gln Leu Lys Gln Phe His Phe His Thr Pro Ser
                85                  90                  95

Glu His Thr Val Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225
```

<210> SEQ ID NO 147
<211> LENGTH: 684
<212> TYPE: DNA
<213> ORGANISM: Artificial sequence
<220> FEATURE:
<223> OTHER INFORMATION: Variant: K38R-G82C-I100V

<400> SEQUENCE: 147

```
atggaacacg aatggagcta cgaaggtgag aagggtcctg agcattgggc gcagttgaaa    60
ccggagttct tttggtgcaa gctgaagaat caatctccga tcaacattga ccgtaagtac   120
aaagtcaaag cgaatctgcc gaagctgaat ctgtattaca aaccgcaaa agagagcgag   180
```

```
gttgtgaaca atggccacac tattcaaatc aacattaaag aggataacac cctgaattat    240
ctgtgtgaaa agtatcaact gaagcagttt cattttcaca cgccgagcga gcataccgtt    300
gagaagaagt cgtacccgtt ggaaatccac ttcgttcaca aaaccgagga tggtaaaatc    360
ttggtcgtgg gtgtgatggc caaactgggt aagacgaata aagagctgga caagattctg    420
aacgtggctc cggcggaaga aggtgaaaag atcctggaca aaaacctgaa cctgaacaac    480
ctgattccga agataaacg ttatatgacg tacagcggca gcctgaccac cccaccgtgt    540
acggaaggcg ttcgttggat cgttctgaag aagccgatca gcattagcaa acagcagttg    600
gagaaactga aaagcgtcat ggtcaacccg aataatcgcc cggttcaaga aatcaattcc    660
cgttggatta ttgagggctt ctaa                                          684
```

<210> SEQ ID NO 148
<211> LENGTH: 227
<212> TYPE: PRT
<213> ORGANISM: Artificial sequence
<220> FEATURE:
<223> OTHER INFORMATION: Variant: K38R-G82C-I100V

<400> SEQUENCE: 148

```
Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Arg Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Cys Glu Lys Tyr Gln Leu Lys Gln Phe His Phe His Thr Pro Ser
                85                  90                  95

Glu His Thr Val Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225
```

<210> SEQ ID NO 149
<211> LENGTH: 684
<212> TYPE: DNA
<213> ORGANISM: Artificial sequence
<220> FEATURE:

<223> OTHER INFORMATION: Variant: K38S-G82C-I100V

<400> SEQUENCE: 149

```
atggaacacg aatggagcta cgaaggtgag aagggtcctg agcattgggc gcagttgaaa      60
ccggagttct tttggtgcaa gctgaagaat caatctccga tcaacattga ctctaagtac     120
aaagtcaaag cgaatctgcc gaagctgaat ctgtattaca aaccgcaaa agagagcgag     180
gttgtgaaca atggccacac tattcaaatc aacattaaag aggataacac cctgaattat     240
ctgtgtgaaa agtatcaact gaagcagttt cattttcaca cgccgagcga gcataccgtt     300
gagaagaagt cgtacccgtt ggaaatccac ttcgttcaca aaaccgagga tggtaaaatc     360
ttggtcgtgg gtgtgatggc caaactgggt aagacgaata aagagctgga caagattctg     420
aacgtggctc cggcggaaga aggtgaaaag atcctggaca aaaacctgaa cctgaacaac     480
ctgattccga agataaacg ttatatgacg tacagcggca gcctgaccac cccaccgtgt     540
acggaaggcg ttcgttggat cgttctgaag aagccgatca gcattagcaa acagcagttg     600
gagaaactga aagcgtcat ggtcaacccg aataatcgcc cggttcaaga aatcaattcc     660
cgttggatta ttgagggctt ctaa                                             684
```

<210> SEQ ID NO 150
<211> LENGTH: 227
<212> TYPE: PRT
<213> ORGANISM: Artificial sequence
<220> FEATURE:
<223> OTHER INFORMATION: Variant: K38S-G82C-I100V

<400> SEQUENCE: 150

```
Met Glu His Glu Trp Ser Tyr Glu Gly Glu Lys Gly Pro Glu His Trp
  1               5                  10                  15

Ala Gln Leu Lys Pro Glu Phe Phe Trp Cys Lys Leu Lys Asn Gln Ser
             20                  25                  30

Pro Ile Asn Ile Asp Ser Lys Tyr Lys Val Lys Ala Asn Leu Pro Lys
         35                  40                  45

Leu Asn Leu Tyr Tyr Lys Thr Ala Lys Glu Ser Glu Val Val Asn Asn
     50                  55                  60

Gly His Thr Ile Gln Ile Asn Ile Lys Glu Asp Asn Thr Leu Asn Tyr
 65                  70                  75                  80

Leu Cys Glu Lys Tyr Gln Leu Lys Gln Phe His Phe His Thr Pro Ser
                 85                  90                  95

Glu His Thr Val Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220
```

Glu Gly Phe
225

<210> SEQ ID NO 151
<211> LENGTH: 684
<212> TYPE: DNA
<213> ORGANISM: Artificial sequence
<220> FEATURE:
<223> OTHER INFORMATION: Variant: K38W-G82C-I100V

<400> SEQUENCE: 151

```
atggaacacg aatggagcta cgaaggtgag aagggtcctg agcattgggc gcagttgaaa      60
ccggagttct tttggtgcaa gctgaagaat caatctccga tcaacattga ctggaagtac     120
aaagtcaaag cgaatctgcc gaagctgaat ctgtattaca aaccgcaaa agagagcgag     180
gttgtgaaca atggccacac tattcaaatc aacattaaag aggataacac cctgaattat     240
ctgtgtgaaa agtatcaact gaagcagttt cattttcaca cgccgagcga gcataccgtt     300
gagaagaagt cgtacccgtt ggaaatccac ttcgttcaca aaaccgagga tggtaaaatc     360
ttggtcgtgg gtgtgatggc caaactgggt aagacgaata agagctgga caagattctg     420
aacgtggctc cggcggaaga aggtgaaaag atcctggaca aaaacctgaa cctgaacaac     480
ctgattccga agataaaacg ttatatgacg tacagcggca gcctgaccac cccaccgtgt     540
acggaaggcg ttcgttggat cgttctgaag aagccgatca gcattagcaa acagcagttg     600
gagaaactga aagcgtcat ggtcaacccg aataatcgcc cggttcaaga aatcaattcc     660
cgttggatta ttgagggctt ctaa                                              684
```

<210> SEQ ID NO 152
<211> LENGTH: 227
<212> TYPE: PRT
<213> ORGANISM: Artificial sequence
<220> FEATURE:
<223> OTHER INFORMATION: Variant: K38W-G82C-I100V

<400> SEQUENCE: 152

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Trp Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Cys Glu Lys Tyr Gln Leu Lys Gln Phe His Phe His Thr Pro Ser
                85                  90                  95

Glu His Thr Val Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr 165                 170                 175
Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225

<210> SEQ ID NO 153
<211> LENGTH: 684
<212> TYPE: DNA
<213> ORGANISM: Artificial sequence
<220> FEATURE:
<223> OTHER INFORMATION: Variant: K38S-K57A-G82C-I100V

<400> SEQUENCE: 153
atggaacacg aatggagcta cgaaggtgag aagggtcctg agcattgggc gcagttgaaa      60
ccggagttct tttggtgcaa gctgaagaat caatctccga tcaacattga ctctaagtac     120
aaagtcaaag cgaatctgcc gaagctgaat ctgtattaca aaccgcagc tgagagcgag      180 gttgtgaaca atggccacac tattcaaatc aacattaaag aggataacac cctgaattat     240
ctgtgtgaaa agtatcaact gaagcagttt cattttcaca cgccgagcga gcataccgtt     300
gagaagaagt cgtacccgtt ggaaatccac ttcgttcaca aaccgagga tggtaaaatc      360 ttggtcgtgg gtgtgatggc caaactgggt aagacgaata aagagctgga caagattctg     420
aacgtggctc cggcggaaga aggtgaaaag atcctggaca aaaacctgaa cctgaacaac     480
ctgattccga agataaacg ttatatgacg tacagcggca gcctgaccac cccaccgtgt      540
acggaaggcg ttcgttggat cgttctgaag aagccgatca gcattagcaa acagcagttg     600
gagaaactga aaagcgtcat ggtcaacccg aataatcgcc ggttcaaga atcaattcc       660 cgttggatta ttgagggctt ctaa                                             684

<210> SEQ ID NO 154
<211> LENGTH: 227
<212> TYPE: PRT
<213> ORGANISM: Artificial sequence
<220> FEATURE:
<223> OTHER INFORMATION: Variant: K38S-K57A-G82C-I100V

<400> SEQUENCE: 154

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Ser Lys Tyr Lys Val Lys Ala Asn Leu Pro Lys
        35                  40                  45

Leu Asn Leu Tyr Tyr Lys Thr Ala Ala Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Cys Glu Lys Tyr Gln Leu Lys Gln Phe His Phe His Thr Pro Ser
                85                  90                  95

Glu His Thr Val Glu Lys Lys Ser Tyr Pro Leu Glu Ile His Phe Val
            100                 105                 110

His Lys Thr Glu Asp Gly Lys Ile Leu Val Gly Val Met Ala Lys
            115                 120                 125
Leu Gly Lys Thr Asn Lys Glu Leu Asp Lys Ile Leu Asn Val Ala Pro
130                 135                 140
Ala Glu Glu Gly Glu Lys Ile Leu Asp Lys Asn Leu Asn Leu Asn Asn
145                 150                 155                 160
Leu Ile Pro Lys Asp Lys Arg Tyr Met Thr Tyr Ser Gly Ser Leu Thr
                165                 170                 175
Thr Pro Pro Cys Thr Glu Gly Val Arg Trp Ile Val Leu Lys Lys Pro
            180                 185                 190
Ile Ser Ile Ser Lys Gln Gln Leu Gly Lys Leu Lys Ser Val Met Val
                195                 200                 205
Asn Pro Asn Asn Arg Pro Val Gln Glu Ile Asn Ser Arg Trp Ile Ile
            210                 215                 220
Glu Gly Phe
225

<210> SEQ ID NO 155
<211> LENGTH: 684
<212> TYPE: DNA
<213> ORGANISM: Artificial sequence
<220> FEATURE:
<223> OTHER INFORMATION: Variant: K38S-K57G-G82C-I100V

<400> SEQUENCE: 155
atggaacacg aatggagcta cgaaggtgag aagggtcctg agcattgggc gcagttgaaa     60
ccggagttct tttggtgcaa gctgaagaat caatctccga tcaacattga cagtaagtac    120
aaagtcaaag cgaatctgcc gaagctgaat ctgtattaca aaccgcagg tgagagcgag    180
gttgtgaaca atggccacac tattcaaatc aacattaaag aggataacac cctgaattat    240
ctgtgtgaaa agtatcaact gaagcagttt cattttcaca cgccgagcga gcataccgtt    300
gagaagaagt cgtacccgtt ggaaatccac ttcgttcaca aaaccgagga tggtaaaatc    360
ttggtcgtgg gtgtgatggc caaactgggt aagacgaata agagctgga caagattctg    420
aacgtggctc cggcggaaga aggtgaaaag atcctggaca aaaacctgaa cctgaacaac    480
ctgattccga agataaaacg ttatatgacg tacagcggca gcctgaccac cccaccgtgt    540
acggaaggcg ttcgttggat cgttctgaag aagccgatca gcattagcaa acagcagttg    600
gagaaactga aaagcgtcat ggtcaacccg aataatcgcc cggttcaaga aatcaattcc    660
cgttggatta ttgagggctt ctaa                                           684

<210> SEQ ID NO 156
<211> LENGTH: 227
<212> TYPE: PRT
<213> ORGANISM: Artificial sequence
<220> FEATURE:
<223> OTHER INFORMATION: Variant: K38S-K57G-G82C-I100V

<400> SEQUENCE: 156

Met Glu His Glu Trp Ser Tyr Glu Gly Glu Lys Gly Pro Glu His Trp
1               5                   10                  15
Ala Gln Leu Lys Pro Glu Phe Phe Trp Cys Lys Leu Lys Asn Gln Ser
            20                  25                  30
Pro Ile Asn Ile Asp Ser Lys Tyr Lys Val Lys Ala Asn Leu Pro Lys
        35                  40                  45
Leu Asn Leu Tyr Tyr Lys Thr Ala Gly Glu Ser Glu Val Val Asn Asn
50                  55                  60

```
Gly His Thr Ile Gln Ile Asn Ile Lys Glu Asp Asn Thr Leu Asn Tyr
 65                  70                  75                  80

Leu Cys Glu Lys Tyr Gln Leu Lys Gln Phe His Phe His Thr Pro Ser
                 85                  90                  95

Glu His Thr Val Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225

<210> SEQ ID NO 157
<211> LENGTH: 684
<212> TYPE: DNA
<213> ORGANISM: Artificial sequence
<220> FEATURE:
<223> OTHER INFORMATION: Variant: K38S-K57L-G82C-I100V

<400> SEQUENCE: 157
atggaacacg aatggagcta cgaaggtgag aagggtcctg agcattgggc gcagttgaaa      60
ccggagttct tttggtgcaa gctgaagaat caatctccga tcaacattga ctctaagtac     120
aaagtcaaag cgaatctgcc gaagctgaat ctgtattaca aaccgcact tgagagcgag      180 gttgtgaaca atggccacac tattcaaatc aacattaaag aggataacac cctgaattat     240
ctgtgtgaaa agtatcaact gaagcagttt cattttcaca cgccgagcga gcataccgtt     300
gagaagaagt cgtacccgtt ggaaatccac ttcgttcaca aaccgaggat ggtaaaatc      360 ttggtcgtgg gtgtgatggc caaactgggt aagacgaata agagctggaa caagattctg     420
aacgtggctc cggcggaaga aggtgaaaag atcctggaca aaaacctgaa cctgaacaac     480
ctgattccga agataaaacg ttatatgacg tacagcggca gcctgaccac cccaccgtgt     540
acggaaggcg ttcgttggat cgttctgaag aagccgatca gcattagcaa acagcagttg     600
gagaaactga aaagcgtcat ggtcaacccg aataatcgcc cggttcaaga aatcaattcc     660
cgttggatta ttgagggctt ctaa                                             684

<210> SEQ ID NO 158
<211> LENGTH: 227
<212> TYPE: PRT
<213> ORGANISM: Artificial sequence
<220> FEATURE:
<223> OTHER INFORMATION: Variant: K38S-K57L-G82C-I100V

<400> SEQUENCE: 158

Met Glu His Glu Trp Ser Tyr Glu Gly Glu Lys Gly Pro Glu His Trp
```

```
              1               5              10              15
            Ala Gln Leu Lys Pro Glu Phe Phe Trp Cys Lys Leu Lys Asn Gln Ser
                             20                  25                  30

Pro Ile Asn Ile Asp Ser Lys Tyr Lys Val Lys Ala Asn Leu Pro Lys
                             35                  40                  45

Leu Asn Leu Tyr Tyr Lys Thr Ala Leu Glu Ser Glu Val Val Asn Asn
                             50                  55                  60

Gly His Thr Ile Gln Ile Asn Ile Lys Glu Asp Asn Thr Leu Asn Tyr
             65                  70                  75                  80

Leu Cys Glu Lys Tyr Gln Leu Lys Gln Phe His Phe His Thr Pro Ser
                             85                  90                  95

Glu His Thr Val Glu Lys Lys Ser Tyr Pro Leu Glu Ile His Phe Val
                            100                 105                 110

His Lys Thr Glu Asp Gly Lys Ile Leu Val Val Gly Val Met Ala Lys
                            115                 120                 125

Leu Gly Lys Thr Asn Lys Glu Leu Asp Lys Ile Leu Asn Val Ala Pro
                            130                 135                 140

Ala Glu Glu Gly Glu Lys Ile Leu Asp Lys Asn Leu Asn Leu Asn Asn
            145                 150                 155                 160

Leu Ile Pro Lys Asp Lys Arg Tyr Met Thr Tyr Ser Gly Ser Leu Thr
                            165                 170                 175

Thr Pro Pro Cys Thr Glu Gly Val Arg Trp Ile Val Leu Lys Lys Pro
                            180                 185                 190

Ile Ser Ile Ser Lys Gln Gln Leu Glu Lys Leu Lys Ser Val Met Val
                            195                 200                 205

Asn Pro Asn Asn Arg Pro Val Gln Glu Ile Asn Ser Arg Trp Ile Ile
            210                 215                 220

Glu Gly Phe
            225

<210> SEQ ID NO 159
<211> LENGTH: 684
<212> TYPE: DNA
<213> ORGANISM: Artificial sequence
<220> FEATURE:
<223> OTHER INFORMATION: Variant: K38S-K57S-G82C-I100V

<400> SEQUENCE: 159
atggaacacg aatggagcta cgaaggtgag aagggtcctg agcattgggc gcagttgaaa       60
ccggagttct tttggtgcaa gctgaagaat caatctccga tcaacattga ctctaagtac      120
aaagtcaaag cgaatctgcc gaagctgaat ctgtattaca aaaccgcatc tgagagcgag      180
gttgtgaaca atggccacac tattcaaatc aacattaaag aggataacac cctgaattat      240
ctgtgtgaaa agtatcaact gaagcagttt cattttcaca cgccgagcga gcataccgtt      300
gagaagaagt cgtacccgtt ggaaatccac ttcgttcaca aaccgaggga tggtaaaatc      360
ttggtcgtgg gtgtgatggc caaactgggt aagacgaata agagctgga caagattctg       420 aacgtggctc cggcggaaga aggtgaaaag atcctggaca aaaacctgaa cctgaacaac      480
ctgattccga agataaacg ttatatgacg tacagcggca gcctgaccac cccaccgtgt       540
acggaaggcg ttcgttggat cgttctgaag aagccgatca gcattagcaa acagcagttg      600
gagaaactga aaagcgtcat ggtcaacccg aataatcgcc cggttcaaga aatcaattcc      660
cgttggatta ttgagggctt ctaa                                             684
```

```
<210> SEQ ID NO 160
<211> LENGTH: 227
<212> TYPE: PRT
<213> ORGANISM: Artificial sequence
<220> FEATURE:
<223> OTHER INFORMATION: Variant: K38S-K57S-G82C-I100V

<400> SEQUENCE: 160

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Ser Lys Tyr Lys Val Lys Ala Asn Leu Pro Lys
        35                  40                  45

Leu Asn Leu Tyr Tyr Lys Thr Ala Ser Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Cys Glu Lys Tyr Gln Leu Lys Gln Phe His Phe His Thr Pro Ser
                85                  90                  95

Glu His Thr Val Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225

<210> SEQ ID NO 161
<211> LENGTH: 684
<212> TYPE: DNA
<213> ORGANISM: Artificial sequence
<220> FEATURE:
<223> OTHER INFORMATION: Variant: K38S-K57V-G82C-I100V

<400> SEQUENCE: 161
atggaacacg aatggagcta cgaaggtgag aagggtcctg agcattgggc gcagttgaaa      60
ccggagttct tttggtgcaa gctgaagaat caatctccga tcaacattga ctctaagtac     120
aaagtcaaag cgaatctgcc gaagctgaat ctgtattaca aaccgcagt tgagagcgag      180 gttgtgaaca atggccacac tattcaaatc aacattaaag aggataacac cctgaattat     240
ctgtgtgaaa agtatcaact gaagcagttt cattttcaca cgccgagcga gcataccgtt     300
gagaagaagt cgtacccgtt ggaaatccac ttcgttcaca aaccgagga tggtaaaatc      360 ttggtcgtgg gtgtgatggc caaactgggt aagacgaata agagctgga caagattctg      420 aacgtggctc cggcggaaga aggtgaaaag atcctggaca aaaacctgaa cctgaacaac     480
```

```
ctgattccga aagataaacg ttatatgacg tacagcggca gcctgaccac cccaccgtgt    540
acggaaggcg ttcgttggat cgttctgaag aagccgatca gcattagcaa acagcagttg    600
gagaaactga aaagcgtcat ggtcaacccg aataatcgcc cggttcaaga aatcaattcc    660
cgttggatta ttgagggctt ctaa                                           684
```

<210> SEQ ID NO 162
<211> LENGTH: 227
<212> TYPE: PRT
<213> ORGANISM: Artificial sequence
<220> FEATURE:
<223> OTHER INFORMATION: Variant: K38S-K57V-G82C-I100V

<400> SEQUENCE: 162

```
Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Ser Lys Tyr Lys Val Lys Ala Asn Leu Pro Lys
        35                  40                  45

Leu Asn Leu Tyr Tyr Lys Thr Ala Val Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Cys Glu Lys Tyr Gln Leu Lys Gln Phe His Phe His Thr Pro Ser
                85                  90                  95

Glu His Thr Val Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Gly Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225
```

<210> SEQ ID NO 163
<211> LENGTH: 684
<212> TYPE: DNA
<213> ORGANISM: Artificial sequence
<220> FEATURE:
<223> OTHER INFORMATION: Variant: Q18F-K20G-K38S-K57L-G82C-I100V

<400> SEQUENCE: 163

```
atggaacacg aatggagcta cgaaggtgag aagggtcctg agcattgggc gttttttggt    60
ccggagttct tttggtgcaa gctgaagaat caatctccga tcaacattga ctctaagtac   120
aaagtcaaag cgaatctgcc gaagctgaat ctgtattaca aaccgcact tgagagcgag   180
```

```
gttgtgaaca atggccacac tattcaaatc aacattaaag aggataacac cctgaattat    240
ctgtgtgaaa agtatcaact gaagcagttt cattttcaca cgccgagcga gcataccgtt    300
gagaagaagt cgtacccgtt ggaaatccac ttcgttcaca aaaccgagga tggtaaaatc    360
ttggtcgtgg gtgtgatggc caaactgggt aagacgaata agagctgga caagattctg     420 aacgtggctc cggcggaaga aggtgaaaag atcctggaca aaacctgaa cctgaacaac     480 ctgattccga agataaaacg ttatatgacg tacagcggca gcctgaccac cccaccgtgt    540
acggaaggcg ttcgttggat cgttctgaag aagccgatca gcattagcaa acagcagttg    600
gagaaactga aaagcgtcat ggtcaacccg aataatcgcc cggttcaaga aatcaattcc    660
cgttggatta ttgagggctt ctaa                                            684
```

<210> SEQ ID NO 164  
<211> LENGTH: 227  
<212> TYPE: PRT  
<213> ORGANISM: Artificial sequence  
<220> FEATURE:  
<223> OTHER INFORMATION: Variant: Q18F-K20G-K38S-K57L-G82C-I100V
<400> SEQUENCE: 164

```
Met Glu His Glu Trp Ser Tyr Glu Gly Glu Lys Gly Pro Glu His Trp
1               5                   10                  15

Ala Phe Leu Gly Pro Glu Phe Phe Trp Cys Lys Leu Lys Asn Gln Ser
            20                  25                  30

Pro Ile Asn Ile Asp Ser Lys Tyr Lys Val Lys Ala Asn Leu Pro Lys
        35                  40                  45

Leu Asn Leu Tyr Tyr Lys Thr Ala Leu Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Cys Glu Lys Tyr Gln Leu Lys Gln Phe His Phe His Thr Pro Ser
                85                  90                  95

Glu His Thr Val Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225
```

<210> SEQ ID NO 165  
<211> LENGTH: 684  
<212> TYPE: DNA  
<213> ORGANISM: Artificial sequence
<220> FEATURE:
<223> OTHER INFORMATION: Variant: Q18R-K20G-K38S-K57L-G82C-I100V

<400> SEQUENCE: 165

```
atggaacacg aatggagcta cgaaggtgag aagggtcctg agcattgggc gcgtttgggt      60
ccggagttct tttggtgcaa gctgaagaat caatctccga tcaacattga ctctaagtac     120
aaagtcaaag cgaatctgcc gaagctgaat ctgtattaca aaccgcact gagagcgag       180
gttgtgaaca atggccacac tattcaaatc aacattaaag aggataacac cctgaattat    240
ctgtgtgaaa agtatcaact gaagcagttt cattttcaca cgccgagcga gcataccgtt    300
gagaagaagt cgtacccgtt ggaaatccac ttcgttcaca aaaccgagga tggtaaaatc    360
ttggtcgtgg gtgtgatggc caaactgggt aagacgaata agagctgga caagattctg     420
aacgtggctc cggcggaaga aggtgaaaag atcctggaca aaaacctgaa cctgaacaac    480
ctgattccga agataaacg ttatatgacg tacagcggca gcctgaccac cccaccgtgt     540
acggaaggcg ttcgttggat cgttctgaag aagccgatca gcattagcaa acagcagttg    600
gagaaactga aagcgtcat ggtcaacccg aataatcgcc cggttcaaga aatcaattcc     660
cgttggatta ttgagggctt ctaa                                            684
```

<210> SEQ ID NO 166
<211> LENGTH: 227
<212> TYPE: PRT
<213> ORGANISM: Artificial sequence
<220> FEATURE:
<223> OTHER INFORMATION: Variant: Q18R-K20G-K38S-K57L-G82C-I100V

<400> SEQUENCE: 166

```
Met Glu His Glu Trp Ser Tyr Glu Gly Glu Lys Gly Pro Glu His Trp
1               5                   10                  15

Ala Arg Leu Gly Pro Glu Phe Phe Trp Cys Lys Leu Lys Asn Gln Ser
            20                  25                  30

Pro Ile Asn Ile Asp Ser Lys Tyr Lys Val Lys Ala Asn Leu Pro Lys
        35                  40                  45

Leu Asn Leu Tyr Tyr Lys Thr Ala Leu Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Cys Glu Lys Tyr Gln Leu Lys Gln Phe His Phe His Thr Pro Ser
                85                  90                  95

Glu His Thr Val Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
```

Glu Gly Phe
225

<210> SEQ ID NO 167
<211> LENGTH: 684
<212> TYPE: DNA
<213> ORGANISM: Artificial sequence
<220> FEATURE:
<223> OTHER INFORMATION: Variant: Q18W-K20G-K38S-K57L-G82C-I100V

<400> SEQUENCE: 167

```
atggaacacg aatggagcta cgaaggtgag aagggtcctg agcattgggc gtggttgggt      60
ccggagttct tttggtgcaa gctgaagaat caatctccga tcaacattga ctctaagtac     120
aaagtcaaag cgaatctgcc gaagctgaat ctgtattaca aaccgcact tgagagcgag      180
gttgtgaaca atggccacac tattcaaatc aacattaaag aggataacac cctgaattat     240
ctgtgtgaaa agtatcaact gaagcagttt cattttcaca cgccgagcga gcataccgtt     300
gagaagaagt cgtacccgtt ggaaatccac ttcgttcaca aaccgagga tggtaaaatc      360
ttggtcgtgg gtgtgatggc caaactgggt aagacgaata agagctgga caagattctg      420
aacgtggctc cggcggaaga aggtgaaaag atcctggaca aaaacctgaa cctgaacaac     480
ctgattccga agataaacg ttatatgacg tacagcggca gcctgaccac cccaccgtgt      540
acggaaggcg ttcgttggat cgttctgaag aagccgatca gcattagcaa acagcagttg     600
gagaaactga aagcgtcat ggtcaacccg aataatcgcc cggttcaaga aatcaattcc      660
cgttggatta ttgagggctt ctaa                                            684
```

<210> SEQ ID NO 168
<211> LENGTH: 227
<212> TYPE: PRT
<213> ORGANISM: Artificial sequence
<220> FEATURE:
<223> OTHER INFORMATION: Variant: Q18W-K20G-K38S-K57L-G82C-I100V

<400> SEQUENCE: 168

Met Glu His Glu Trp Ser Tyr Glu Gly Glu Lys Gly Pro Glu His Trp
1               5                   10                  15

Ala Trp Leu Gly Pro Glu Phe Phe Trp Cys Lys Leu Lys Asn Gln Ser
            20                  25                  30

Pro Ile Asn Ile Asp Ser Lys Tyr Lys Val Lys Ala Asn Leu Pro Lys
        35                  40                  45

Leu Asn Leu Tyr Tyr Lys Thr Ala Leu Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Cys Glu Lys Tyr Gln Leu Lys Gln Phe His Phe His Thr Pro Ser
                85                  90                  95

Glu His Thr Val Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
            165                 170                 175

Thr Pro Pro Cys Thr Glu Gly Val Arg Trp Ile Val Leu Lys Lys Pro
        180                 185                 190

Ile Ser Ile Ser Lys Gln Gln Leu Glu Lys Leu Lys Ser Val Met Val
            195                 200                 205

Asn Pro Asn Asn Arg Pro Val Gln Glu Ile Asn Ser Arg Trp Ile Ile
        210                 215                 220

Glu Gly Phe
225

<210> SEQ ID NO 169
<211> LENGTH: 684
<212> TYPE: DNA
<213> ORGANISM: Artificial sequence
<220> FEATURE:
<223> OTHER INFORMATION: Variant: Q18R-K20W-K38S-K57L-G82C-I100V

<400> SEQUENCE: 169
atggaacacg aatggagcta cgaaggtgag aagggtcctg agcattgggc gcgtttgtgg      60
ccggagttct tttggtgcaa gctgaagaat caatctccga tcaacattga ctctaagtac     120
aaagtcaaag cgaatctgcc gaagctgaat ctgtattaca aaccgcact tgagagcgag     180 gttgtgaaca atggccacac tattcaaatc aacattaaag aggataacac cctgaattat     240
ctgtgtgaaa agtatcaact gaagcagttt cattttcaca cgccgagcga gcataccgtt     300
gagaagaagt cgtacccgtt ggaaatccac ttcgttcaca aaccgaggga tggtaaaatc     360
ttggtcgtgg gtgtgatggc caaactgggt aagacgaata agagctggaa caagattctg     420
aacgtggctc cggcggaaga aggtgaaaag atcctggaca aaaacctgaa cctgaacaac     480
ctgattccga agataaacg ttatatgacg tacagcggca gcctgaccac cccaccgtgt     540
acggaaggcg ttcgttggat cgttctgaag aagccgatca gcattagcaa acagcagttg     600
gagaaactga aagcgtcat ggtcaacccg aataatcgcc cggttcaaga aatcaattcc     660
cgttggatta ttgagggctt ctaa                                            684

<210> SEQ ID NO 170
<211> LENGTH: 227
<212> TYPE: PRT
<213> ORGANISM: Artificial sequence
<220> FEATURE:
<223> OTHER INFORMATION: Variant: Q18R-K20W-K38S-K57L-G82C-I100V

<400> SEQUENCE: 170

Met Glu His Glu Trp Ser Tyr Glu Gly Glu Lys Gly Pro Glu His Trp
1               5                   10                  15

Ala Arg Leu Trp Pro Glu Phe Phe Trp Cys Lys Leu Lys Asn Gln Ser
            20                  25                  30

Pro Ile Asn Ile Asp Ser Lys Tyr Lys Val Lys Ala Asn Leu Pro Lys
        35                  40                  45

Leu Asn Leu Tyr Tyr Lys Thr Ala Leu Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Cys Glu Lys Tyr Gln Leu Lys Gln Phe His Phe His Thr Pro Ser
                85                  90                  95

Glu His Thr Val Glu Lys Lys Ser Tyr Pro Leu Glu Ile His Phe Val
            100                 105                 110

```
His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
                195                 200                 205

Asn Pro Asn Asn Arg Pro Val Gln Glu Ile Asn Ser Arg Trp Ile Ile
            210                 215                 220

Glu Gly Phe
225

<210> SEQ ID NO 171
<211> LENGTH: 684
<212> TYPE: DNA
<213> ORGANISM: Artificial sequence
<220> FEATURE:
<223> OTHER INFORMATION: Variant: Q18R-K20A-K38S-K57L-G82C-I100V

<400> SEQUENCE: 171
atggaacacg aatggagcta cgaaggtgag aagggtcctg agcattgggc gcgtttggct      60
ccggagttct tttggtgcaa gctgaagaat caatctccga tcaacattga ctctaagtac     120
aaagtcaaag cgaatctgcc gaagctgaat ctgtattaca aaccgcact tgagagcgag      180 gttgtgaaca atgccacac tattcaaatc aacattaaag aggataacac cctgaattat     240
ctgtgtgaaa agtatcaact gaagcagttt cattttcaca cgccgagcga gcataccgtt     300
gagaagaagt cgtacccgtt ggaaatccac ttcgttcaca aaaccgagga tggtaaaatc     360
ttggtcgtgg gtgtgatggc caaactgggt aagacgaata agagctgga caagattctg      420 aacgtggctc cggcggaaga aggtgaaaag atcctggaca aaaacctgaa cctgaacaac     480
ctgattccga agataaaacg ttatatgacg tacagcggca gcctgaccac cccaccgtgt     540
acggaaggcg ttcgttggat cgttctgaag aagccgatca gcattagcaa acagcagttg     600
gagaaactga aagcgtcat ggtcaacccg aataatcgcc cggttcaaga aatcaattcc     660
cgttggatta ttgagggctt ctaa                                            684

<210> SEQ ID NO 172
<211> LENGTH: 227
<212> TYPE: PRT
<213> ORGANISM: Artificial sequence
<220> FEATURE:
<223> OTHER INFORMATION: Variant: Q18R-K20A-K38S-K57L-G82C-I100V

<400> SEQUENCE: 172

Met Glu His Glu Trp Ser Tyr Glu Gly Glu Lys Gly Pro Glu His Trp
1               5                   10                  15

Ala Arg Leu Ala Pro Glu Phe Phe Trp Cys Lys Leu Lys Asn Gln Ser
            20                  25                  30

Pro Ile Asn Ile Asp Ser Lys Tyr Lys Val Lys Ala Asn Leu Pro Lys
        35                  40                  45

Leu Asn Leu Tyr Tyr Lys Thr Ala Leu Glu Ser Glu Val Val Asn Asn
```

```
                50                  55                  60
Gly His Thr Ile Gln Ile Asn Ile Lys Glu Asp Asn Thr Leu Asn Tyr
 65                  70                  75                  80

Leu Cys Glu Lys Tyr Gln Leu Lys Gln Phe His Phe His Thr Pro Ser
                 85                  90                  95

Glu His Thr Val Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225

<210> SEQ ID NO 173
<211> LENGTH: 684
<212> TYPE: DNA
<213> ORGANISM: Artificial sequence
<220> FEATURE:
<223> OTHER INFORMATION: Variant: Q18R-K20R-K38S-K57L-G82C-I100V

<400> SEQUENCE: 173
atggaacacg aatggagcta cgaaggtgag aagggtcctg agcattgggc gcgtttgcgt      60
ccggagttct tttggtgcaa gctgaagaat caatctccga tcaacattga ctctaagtac     120
aaagtcaaag cgaatctgcc gaagctgaat ctgtattaca aaaccgcact tgagagcgag     180
gttgtgaaca atggccacac tattcaaatc aacattaaag aggataacac cctgaattat     240
ctgtgtgaaa agtatcaact gaagcagttt cattttcaca cgccgagcga gcataccgtt     300
gagaagaagt cgtacccgtt ggaaatccac ttcgttcaca aaaccgagga tggtaaaatc     360
ttggtcgtgg gtgtgatggc caaactgggt aagacgaata agagctgga caagattctg     420 aacgtggctc cggcggaaga aggtgaaaag atcctggaca aaaacctgaa cctgaacaac     480
ctgattccga agataaacg ttatatgacg tacagcggca gcctgaccac cccaccgtgt     540
acggaaggcg ttcgttggat cgttctgaag aagccgatca gcattagcaa acagcagttg     600
gagaaactga aaagcgtcat ggtcaacccg aataatcgcc cggttcaaga aatcaattcc     660
cgttggatta ttgagggctt ctaa                                            684

<210> SEQ ID NO 174
<211> LENGTH: 227
<212> TYPE: PRT
<213> ORGANISM: Artificial sequence
<220> FEATURE:
<223> OTHER INFORMATION: Variant: Q18R-K20R-K38S-K57L-G82C-I100V

<400> SEQUENCE: 174
```

```
Met Glu His Glu Trp Ser Tyr Glu Gly Glu Lys Gly Pro Glu His Trp
1               5                  10                 15

Ala Arg Leu Arg Pro Glu Phe Phe Trp Cys Lys Leu Lys Asn Gln Ser
            20                  25                  30

Pro Ile Asn Ile Asp Ser Lys Tyr Lys Val Lys Ala Asn Leu Pro Lys
                35                  40                  45

Leu Asn Leu Tyr Tyr Lys Thr Ala Leu Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Cys Glu Lys Tyr Gln Leu Lys Gln Phe His Phe His Thr Pro Ser
                85                  90                  95

Glu His Thr Val Glu Lys Lys Ser Tyr Pro Leu Glu Ile His Phe Val
                100                 105                 110

His Lys Thr Glu Asp Gly Lys Ile Leu Val Val Gly Val Met Ala Lys
            115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
210                 215                 220

Glu Gly Phe
225

<210> SEQ ID NO 175
<211> LENGTH: 684
<212> TYPE: DNA
<213> ORGANISM: Artificial sequence
<220> FEATURE:
<223> OTHER INFORMATION: Variant: Q18C-K20S-K38S-K57L-G82C-I100V

<400> SEQUENCE: 175
atggaacacg aatggagcta cgaaggtgag aagggtcctg agcattgggc gtgtttgtct      60
ccggagttct tttggtgcaa gctgaagaat caatctccga tcaacattga ctctaagtac     120
aaagtcaaag cgaatctgcc gaagctgaat ctgtattaca aaccgcact  tgagagcgag     180 gttgtgaaca atggccacac tattcaaatc aacattaaag aggataacac cctgaattat     240
ctgtgtgaaa agtatcaact gaagcagttt cattttcaca cgccgagcga gcataccgtt     300
gagaagaagt cgtacccgtt ggaaatccac ttcgttcaca aaaccgagga tggtaaaatc     360
ttggtcgtgg gtgtgatggc caaactgggt aagacgaata agagctgga  caagattctg     420 aacgtggctc cggcggaaga aggtgaaaag atcctggaca aaaacctgaa cctgaacaac     480
ctgattccga agataaacg ttatatgacg tacagcggca gcctgaccac cccaccgtgt     540
acggaaggcg ttcgttggat cgttctgaag aagccgatca gcattagcaa acagcagttg     600
gagaaactga aaagcgtcat ggtcaacccg aataatcgcc cggttcaaga aatcaattcc     660
cgttggatta ttgagggctt ctaa                                            684
```

<210> SEQ ID NO 176
<211> LENGTH: 227
<212> TYPE: PRT
<213> ORGANISM: Artificial sequence
<220> FEATURE:
<223> OTHER INFORMATION: Variant: Q18C-K20S-K38S-K57L-G82C-I100V

<400> SEQUENCE: 176

```
Met Glu His Glu Trp Ser Tyr Glu Gly Glu Lys Gly Pro Glu His Trp
1               5                   10                  15
Ala Cys Leu Ser Pro Glu Phe Phe Trp Cys Lys Leu Lys Asn Gln Ser
            20                  25                  30
Pro Ile Asn Ile Asp Ser Lys Tyr Lys Val Lys Ala Asn Leu Pro Lys
        35                  40                  45
Leu Asn Leu Tyr Tyr Lys Thr Ala Leu Glu Ser Glu Val Val Asn Asn
    50                  55                  60
Gly His Thr Ile Gln Ile Asn Ile Lys Glu Asp Asn Thr Leu Asn Tyr
65                  70                  75                  80
Leu Cys Glu Lys Tyr Gln Leu Lys Gln Phe His Phe His Thr Pro Ser
                85                  90                  95
Glu His Thr Val Glu Lys Lys Ser Tyr Pro Leu Glu Ile His Phe Val
            100                 105                 110
His Lys Thr Glu Asp Gly Lys Ile Leu Val Val Gly Val Met Ala Lys
        115                 120                 125
Leu Gly Lys Thr Asn Lys Glu Leu Asp Lys Ile Leu Asn Val Ala Pro
    130                 135                 140
Ala Glu Glu Gly Glu Lys Ile Leu Asp Lys Asn Leu Asn Leu Asn Asn
145                 150                 155                 160
Leu Ile Pro Lys Asp Lys Arg Tyr Met Thr Tyr Ser Gly Ser Leu Thr
                165                 170                 175
Thr Pro Pro Cys Thr Glu Gly Val Arg Trp Ile Val Leu Lys Lys Pro
            180                 185                 190
Ile Ser Ile Ser Lys Gln Gln Leu Glu Lys Leu Lys Ser Val Met Val
        195                 200                 205
Asn Pro Asn Asn Arg Pro Val Gln Glu Ile Asn Ser Arg Trp Ile Ile
    210                 215                 220
Glu Gly Phe
225
```

<210> SEQ ID NO 177
<211> LENGTH: 684
<212> TYPE: DNA
<213> ORGANISM: Artificial sequence
<220> FEATURE:
<223> OTHER INFORMATION: Variant: Q18C-K20V-K38S-K57L-G82C-I100V

<400> SEQUENCE: 177

```
atggaacacg aatggagcta cgaaggtgag aagggtcctg agcattgggc gtgtttggtt      60
ccggagttct tttggtgcaa gctgaagaat caatctccga tcaacattga ctctaagtac     120
aaagtcaaag cgaatctgcc gaagctgaat ctgtattaca aaccgcact tgagagcgag     180
gttgtgaaca atggccacac tattcaaatc aacattaaag aggataacac cctgaattat     240
ctgtgtgaaa agtatcaact gaagcagttt cattttcaca cgccgagcga gcataccgtt     300
gagaagaagt cgtacccgtt ggaaatccac ttcgttcaca aaccgaggga tgtaaaatc      360
ttggtcgtgg gtgtgatggc caaactgggt aagacgaata agagctgga caagattctg     420
```

```
aacgtggctc cggcggaaga aggtgaaaag atcctggaca aaaacctgaa cctgaacaac      480
ctgattccga agataaacg ttatatgacg tacagcggca gcctgaccac cccaccgtgt       540
acggaaggcg ttcgttggat cgttctgaag aagccgatca gcattagcaa acagcagttg      600
gagaaactga aaagcgtcat ggtcaacccg aataatcgcc cggttcaaga aatcaattcc      660
cgttggatta ttgagggctt ctaa                                             684
```

<210> SEQ ID NO 178
<211> LENGTH: 227
<212> TYPE: PRT
<213> ORGANISM: Artificial sequence
<220> FEATURE:
<223> OTHER INFORMATION: Variant: Q18C-K20V-K38S-K57L-G82C-I100V

<400> SEQUENCE: 178

```
Met Glu His Glu Trp Ser Tyr Glu Gly Glu Lys Gly Pro Glu His Trp
1               5                   10                  15

Ala Cys Leu Val Pro Glu Phe Phe Trp Cys Lys Leu Lys Asn Gln Ser
            20                  25                  30

Pro Ile Asn Ile Asp Ser Lys Tyr Lys Val Lys Ala Asn Leu Pro Lys
        35                  40                  45

Leu Asn Leu Tyr Tyr Lys Thr Ala Leu Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Cys Glu Lys Tyr Gln Leu Lys Gln Phe His Phe His Thr Pro Ser
                85                  90                  95

Glu His Thr Val Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225
```

<210> SEQ ID NO 179
<211> LENGTH: 684
<212> TYPE: DNA
<213> ORGANISM: Artificial sequence
<220> FEATURE:
<223> OTHER INFORMATION: Variant: Q18A-K20T-K38S-K57L-G82C-I100V

<400> SEQUENCE: 179

```
atggaacacg aatggagcta cgaaggtgag aagggtcctg agcattgggc ggctttgact      60
ccggagttct tttggtgcaa gctgaagaat caatctccga tcaacattga ctctaagtac     120
```

-continued

```
aaagtcaaag cgaatctgcc gaagctgaat ctgtattaca aaaccgcact tgagagcgag      180
gttgtgaaca atggccacac tattcaaatc aacattaaag aggataacac cctgaattat      240
ctgtgtgaaa agtatcaact gaagcagttt cattttcaca cgccgagcga gcataccgtt      300
gagaagaagt cgtacccgtt ggaaatccac ttcgttcaca aaaccgagga tggtaaaatc      360
ttggtcgtgg gtgtgatggc caaactgggt aagacgaata agagctgga caagattctg       420 aacgtggctc cggcggaaga aggtgaaaag atcctggaca aaaacctgaa cctgaacaac      480
ctgattccga agataaacg ttatatgacg tacagcggca gcctgaccac cccaccgtgt       540
acggaaggcg ttcgttggat cgttctgaag aagccgatca gcattagcaa acagcagttg      600
gagaaactga aagcgtcat ggtcaacccg aataatcgcc cggttcaaga aatcaattcc       660
cgttggatta ttgagggctt ctaa                                             684
```

<210> SEQ ID NO 180
<211> LENGTH: 227
<212> TYPE: PRT
<213> ORGANISM: Artificial sequence
<220> FEATURE:
<223> OTHER INFORMATION: Variant: Q18A-K20T-K38S-K57L-G82C-I100V

<400> SEQUENCE: 180

```
Met Glu His Glu Trp Ser Tyr Glu Gly Glu Lys Gly Pro Glu His Trp
1               5                   10                  15

Ala Ala Leu Thr Pro Glu Phe Phe Trp Cys Lys Leu Lys Asn Gln Ser
            20                  25                  30

Pro Ile Asn Ile Asp Ser Lys Tyr Lys Val Lys Ala Asn Leu Pro Lys
        35                  40                  45

Leu Asn Leu Tyr Tyr Lys Thr Ala Leu Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Cys Glu Lys Tyr Gln Leu Lys Gln Phe His Phe His Thr Pro Ser
                85                  90                  95

Glu His Thr Val Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225
```

<210> SEQ ID NO 181
<211> LENGTH: 684
<212> TYPE: DNA

```
<213> ORGANISM: Artificial sequence
<220> FEATURE:
<223> OTHER INFORMATION: Variant: G65S

<400> SEQUENCE: 181
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaccgcaaa agagagcgag     180 gttgtgaaca attctcacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaaccgagga tggtaaaatc     360
ttggtcgtgg gtgtgatggc caaactgggt aagacgaata aagagctgga caagattctg     420
aacgtggctc cggcggaaga aggtgaaaag atcctggaca aaaacctgaa cctgaacaac     480
ctgattccga agataaacg ttatatgacg tacagcggca gcctgaccac cccaccgtgt     540
acggaaggcg ttcgttggat cgttctgaag aagccgatca gcattagcaa acagcagttg     600
gagaaactga aagcgtcat ggtcaacccg aataatcgcc cggttcaaga aatcaattcc     660
cgttggatta ttgagggctt ctaa                                              684

<210> SEQ ID NO 182
<211> LENGTH: 227
<212> TYPE: PRT
<213> ORGANISM: Artificial sequence
<220> FEATURE:
<223> OTHER INFORMATION: Variant: G65S

<400> SEQUENCE: 182

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Ser His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205
```

```
Asn Pro Asn Asn Arg Pro Val Gln Glu Ile Asn Ser Arg Trp Ile Ile
    210                 215                 220

Glu Gly Phe
225

<210> SEQ ID NO 183
<211> LENGTH: 684
<212> TYPE: DNA
<213> ORGANISM: Artificial sequence
<220> FEATURE:
<223> OTHER INFORMATION: Variant: K88E

<400> SEQUENCE: 183
atggaacacg aatggagcta cgaaggtgag aagggtcctg agcattgggc gcagttgaaa      60
ccggagttct tttggtgcaa gctgaagaat caatctccga tcaacattga caagaagtac    120
aaagtcaaag cgaatctgcc gaagctgaat ctgtattaca aaccgcaaa agagagcgag     180 gttgtgaaca atggccacac tattcaaatc aacattaaag aggataacac cctgaattat    240
ctgggtgaaa agtatcaact ggagcagttt cattttcaca cgccgagcga agcataccatc   300 gagaagaagt cgtacccgtt ggaaatccac ttcgttcaca aaaccgagga tggtaaaatc    360
ttggtcgtgg gtgtgatggc caaactgggt aagacgaata aagagctgga caagattctg    420
aacgtggctc cggcggaaga aggtgaaaag atcctggaca aaaacctgaa cctgaacaac    480
ctgattccga agataaaacg ttatatgacg tacagcggca gcctgaccac cccaccgtgt    540
acggaaggcg ttcgttggat cgttctgaag aagccgatca gcattagcaa acagcagttg    600
gagaaactga aaagcgtcat ggtcaacccg aataatcgcc cggttcaaga aatcaattcc    660
cgttggatta ttgagggctt ctaa                                            684

<210> SEQ ID NO 184
<211> LENGTH: 227
<212> TYPE: PRT
<213> ORGANISM: Artificial sequence
<220> FEATURE:
<223> OTHER INFORMATION: Variant: K88E

<400> SEQUENCE: 184

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Glu Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160
```

```
Leu Ile Pro Lys Asp Lys Arg Tyr Met Thr Tyr Ser Gly Ser Leu Thr
            165                 170                 175

Thr Pro Pro Cys Thr Glu Gly Val Arg Trp Ile Val Leu Lys Lys Pro
        180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225

<210> SEQ ID NO 185
<211> LENGTH: 684
<212> TYPE: DNA
<213> ORGANISM: Artificial sequence
<220> FEATURE:
<223> OTHER INFORMATION: Variant: K114I

<400> SEQUENCE: 185
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaccgcaaa agagagcgag     180 gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca tcaccgagga tggtaaaatc     360
ttggtcgtgg gtgtgatggc caaactgggt aagacgaata agagctgga caagattctg     420 aacgtggctc cggcggaaga aggtgaaaag atcctggaca aaaacctgaa cctgaacaac     480
ctgattccga agataaaacg ttatatgacg tacagcggca gcctgaccac cccaccgtgt     540
acggaaggcg ttcgttggat cgttctgaag aagccgatca gcattagcaa acagcagttg     600
gagaaactga aaagcgtcat ggtcaacccg aataatcgcc cggttcaaga aatcaattcc     660
cgttggatta ttgagggctt ctaa                                             684

<210> SEQ ID NO 186
<211> LENGTH: 227
<212> TYPE: PRT
<213> ORGANISM: Artificial sequence
<220> FEATURE:
<223> OTHER INFORMATION: Variant: K114I

<400> SEQUENCE: 186

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
```

```
                  100                 105                 110
His Ile Thr Glu Asp Gly Lys Ile Leu Val Val Gly Val Met Ala Lys
            115                 120                 125

Leu Gly Lys Thr Asn Lys Glu Leu Asp Lys Ile Leu Asn Val Ala Pro
        130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225

<210> SEQ ID NO 187
<211> LENGTH: 684
<212> TYPE: DNA
<213> ORGANISM: Artificial sequence
<220> FEATURE:
<223> OTHER INFORMATION: Variant: V122I

<400> SEQUENCE: 187
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaccgcaaa agagagcgag      180 gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaaccgagga tggtaaaatc     360
ttgatcgtgg gtgtgatggc caaactgggt aagacgaata agagctgga caagattctg      420 aacgtggctc cggcggaaga aggtgaaaag atcctggaca aaaacctgaa cctgaacaac     480
ctgattccga agataaaacg ttatatgacg tacagcggca gcctgaccac cccaccgtgt     540
acggaaggcg ttcgttggat cgttctgaag aagccgatca gcattagcaa acagcagttg     600
gagaaactga aaagcgtcat ggtcaacccg aataatcgcc cggttcaaga aatcaattcc     660
cgttggatta ttgagggctt ctaa                                            684

<210> SEQ ID NO 188
<211> LENGTH: 227
<212> TYPE: PRT
<213> ORGANISM: Artificial sequence
<220> FEATURE:
<223> OTHER INFORMATION: Variant: V122I

<400> SEQUENCE: 188

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45
```

Leu Asn Leu Tyr Tyr Lys Thr Ala Lys Glu Ser Glu Val Val Asn Asn
 50                  55                  60

Gly His Thr Ile Gln Ile Asn Ile Lys Glu Asp Asn Thr Leu Asn Tyr
 65                  70                  75                  80

Leu Gly Glu Lys Tyr Gln Leu Lys Gln Phe His Phe His Thr Pro Ser
                 85                  90                  95

Glu His Thr Ile Glu Lys Lys Ser Tyr Pro Leu Glu Ile His Phe Val
            100                 105                 110

His Lys Thr Glu Asp Gly Lys Ile Leu Ile Val Gly Val Met Ala Lys
        115                 120                 125

Leu Gly Lys Thr Asn Lys Glu Leu Asp Lys Ile Leu Asn Val Ala Pro
130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
210                 215                 220

Glu Gly Phe
225

<210> SEQ ID NO 189
<211> LENGTH: 684
<212> TYPE: DNA
<213> ORGANISM: Artificial sequence
<220> FEATURE:
<223> OTHER INFORMATION: Variant: M126L

<400> SEQUENCE: 189
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaaccgcaaa agagagcgag     180
gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaaccgagga tggtaaaatc     360
ttggtcgtgg gtgtgcttgc caaactgggt aagacgaata agagctggac aagattctg      420 aacgtggctc cggcggaaga aggtgaaaag atcctggaca aaaacctgaa cctgaacaac     480
ctgattccga agataaaacg ttatatgacg tacagcggca gcctgaccac cccaccgtgt     540
acggaaggcg ttcgttggat cgttctgaag aagccgatca gcattagcaa acagcagttg     600
gagaaactga aagcgtcat ggtcaacccg aataatcgcc cggttcaaga aatcaattcc     660
cgttggatta ttgagggctt ctaa                                           684

<210> SEQ ID NO 190
<211> LENGTH: 227
<212> TYPE: PRT
<213> ORGANISM: Artificial sequence
<220> FEATURE:
<223> OTHER INFORMATION: Variant: M126L

<400> SEQUENCE: 190

```
Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Leu Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225

<210> SEQ ID NO 191
<211> LENGTH: 684
<212> TYPE: DNA
<213> ORGANISM: Artificial sequence
<220> FEATURE:
<223> OTHER INFORMATION: Variant: G148A

<400> SEQUENCE: 191
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaccgcaaa agagagcgag     180 gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaaccgagga tggtaaaatc     360
ttggtcgtgg gtgtgatggc caaactgggt aagacgaata agagctgga caagattctg     420 aacgtggctc cggcggaaga agctgaaaag atcctggaca aaaacctgaa cctgaacaac     480
ctgattccga agataaacg ttatatgacg tacagcggca gcctgaccac cccaccgtgt     540
acggaaggcg ttcgttggat cgttctgaag aagccgatca gcattagcaa acagcagttg     600
gagaaactga aaagcgtcat ggtcaacccg aataatcgcc cggttcaaga aatcaattcc     660
cgttggatta ttgagggctt ctaa                                            684
```

<210> SEQ ID NO 192
<211> LENGTH: 227
<212> TYPE: PRT
<213> ORGANISM: Artificial sequence
<220> FEATURE:
<223> OTHER INFORMATION: Variant: G148A

<400> SEQUENCE: 192

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Ala Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225

<210> SEQ ID NO 193
<211> LENGTH: 684
<212> TYPE: DNA
<213> ORGANISM: Artificial sequence
<220> FEATURE:
<223> OTHER INFORMATION: Variant: E14D

<400> SEQUENCE: 193
atggaacacg aatggagcta cgaaggtgag aagggtcctg atcattgggc gcagttgaaa        60
ccggagttct tttggtgcaa gctgaagaat caatctccga tcaacattga caagaagtac       120
aaagtcaaag cgaatctgcc gaagctgaat ctgtattaca aaccgcaaa agagagcgag        180 gttgtgaaca atggccacac tattcaaatc aacattaaag aggataacac cctgaattat       240
ctgggtgaaa agtatcaact gaagcagttt cattttcaca cgccgagcga gcataccatc       300
gagaagaagt cgtacccgtt ggaaatccac ttcgttcaca aaaccgagga tggtaaaatc       360
ttggtcgtgg gtgtgatggc caaactgggt aagacgaata agagctgga caagattctg        420

```
aacgtggctc cggcggaaga aggtgaaaag atcctggaca aaaacctgaa cctgaacaac    480
ctgattccga agataaacg ttatatgacg tacagcggca gcctgaccac cccaccgtgt    540
acggaaggcg ttcgttggat cgttctgaag aagccgatca gcattagcaa acagcagttg    600
gagaaactga atctgtcat ggtcaacccg aataatcgcc cggttcaaga aatcaattcc    660
cgttggatta ttgagggctt ctaa                                          684
```

<210> SEQ ID NO 194
<211> LENGTH: 227
<212> TYPE: PRT
<213> ORGANISM: Artificial sequence
<220> FEATURE:
<223> OTHER INFORMATION: Variant: E14D

<400> SEQUENCE: 194

```
Met Glu His Glu Trp Ser Tyr Glu Gly Glu Lys Gly Pro Asp His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225
```

<210> SEQ ID NO 195
<211> LENGTH: 684
<212> TYPE: DNA
<213> ORGANISM: Artificial sequence
<220> FEATURE:
<223> OTHER INFORMATION: Variant: Q18F-K20R-K38S-K57L-G82C-I100V

<400> SEQUENCE: 195

```
atggaacacg aatggagcta cgaaggtgag aagggtcctg agcattgggc gttttttgcgt     60 ccggagttct tttggtgcaa gctgaagaat caatctccga tcaacattga ctctaagtac    120
```

```
aaagtcaaag cgaatctgcc gaagctgaat ctgtattaca aaaccgcact tgagagcgag    180
gttgtgaaca atggccacac tattcaaatc aacattaaag aggataacac cctgaattat    240
ctgtgtgaaa agtatcaact gaagcagttt cattttcaca cgccgagcga gcataccgtt    300
gagaagaagt cgtacccgtt ggaaatccac ttcgttcaca aaaccgagga tggtaaaatc    360
ttggtcgtgg gtgtgatggc caaactgggt aagacgaata agagctgga caagattctg    420 aacgtggctc cggcggaaga aggtgaaaag atcctggaca aaaacctgaa cctgaacaac    480
ctgattccga agataaacg ttatatgacg tacagcggca gcctgaccac cccaccgtgt    540
acggaaggcg ttcgttggat cgttctgaag aagccgatca gcattagcaa acagcagttg    600
gagaaactga aagcgtcat ggtcaacccg aataatcgcc cggttcaaga aatcaattcc    660
cgttggatta ttgagggctt ctaa                                          684
```

<210> SEQ ID NO 196
<211> LENGTH: 227
<212> TYPE: PRT
<213> ORGANISM: Artificial sequence
<220> FEATURE:
<223> OTHER INFORMATION: Variant: Q18F-K20R-K38S-K57L-G82C-I100V

<400> SEQUENCE: 196

```
Met Glu His Glu Trp Ser Tyr Glu Gly Glu Lys Gly Pro Glu His Trp
1               5                   10                  15

Ala Phe Leu Arg Pro Glu Phe Phe Trp Cys Lys Leu Lys Asn Gln Ser
            20                  25                  30

Pro Ile Asn Ile Asp Ser Lys Tyr Lys Val Lys Ala Asn Leu Pro Lys
        35                  40                  45

Leu Asn Leu Tyr Tyr Lys Thr Ala Leu Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Cys Glu Lys Tyr Gln Leu Lys Gln Phe His Phe His Thr Pro Ser
                85                  90                  95

Glu His Thr Val Glu Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225
```

<210> SEQ ID NO 197
<211> LENGTH: 260

```
<212> TYPE: PRT
<213> ORGANISM: Artificial sequence
<220> FEATURE:
<223> OTHER INFORMATION: Variant M6X Enzyme

<400> SEQUENCE: 197

Met Ser His His Trp Gly Tyr Gly Lys His Asn Gly Pro Glu His Trp
1               5                   10                  15

His Lys Asp Phe Pro Ile Ala Lys Gly Glu Arg Gln Ser Pro Val Asp
            20                  25                  30

Ile Asp Thr His Thr Ala Lys Tyr Asp Pro Ser Leu Lys Pro Leu Ser
        35                  40                  45

Val Ser Tyr Asp Gln Ala Thr Ser Leu Arg Ile Leu Asn Asn Gly His
    50                  55                  60

Thr Phe Asn Val Glu Phe Asp Asp Ser Gln Asp Lys Ala Val Leu Lys
65                  70                  75                  80

Gly Gly Pro Leu Asp Gly Thr Tyr Arg Leu Ile Gln Phe His Phe His
                85                  90                  95

Trp Gly Ser His Asp Gly Gln Gly Ser Glu His Thr Val Asp Lys Lys
            100                 105                 110

Lys Tyr Ala Ala Glu Leu His Leu Val His Trp Asn Thr Lys Tyr Gly
        115                 120                 125

Asp Phe Gly Lys Ala Val Gln Gln Pro Asp Gly Leu Ala Val Leu Gly
    130                 135                 140

Ile Phe Leu Lys Val Gly Ser Ala Leu Pro Gly Leu Gln Lys Val Val
145                 150                 155                 160

Asp Val Leu Asp Ser Ile Lys Thr Lys Gly Lys Ser Ala Asp Phe Thr
                165                 170                 175

Asn Phe Asp Pro Arg Gly Leu Leu Pro Glu Ser Leu Asp Tyr Trp Thr
            180                 185                 190

Tyr Pro Gly Ser Leu Thr Thr Pro Pro Leu Leu Glu Cys Val Thr Trp
        195                 200                 205

Ile Val Leu Lys Glu Pro Ile Ser Val Ser Ser Glu Gln Val Ser Lys
    210                 215                 220

Phe Arg Lys Leu Asn Phe Asn Gly Glu Gly Glu Pro Glu Glu Pro Met
225                 230                 235                 240

Val Asp Asn Trp Arg Pro Thr Gln Pro Leu Lys Asn Arg Gln Ile Lys
                245                 250                 255

Ala Ser Phe Lys
            260

<210> SEQ ID NO 198

<400> SEQUENCE: 198

000

<210> SEQ ID NO 199
<211> LENGTH: 684
<212> TYPE: DNA
<213> ORGANISM: Artificial sequence
<220> FEATURE:
<223> OTHER INFORMATION: Variant: Q18T

<400> SEQUENCE: 199
atggaacacg aatggagcta cgaaggtgag aagggtcctg agcattgggc gactttgaaa      60
ccggagttct tttggtgcaa gctgaagaat caatctccga tcaacattga caagaagtac     120
```

| | | |
|---|---|---|
| aaagtcaaag cgaatctgcc gaagctgaat ctgtattaca aaaccgcaaa agagagcgag | 180 | |
| gttgtgaaca atggccacac tattcaaatc aacattaaag aggataacac cctgaattat | 240 | |
| ctgggtgaaa agtatcaact gaagcagttt cattttcaca cgccgagcga gcataccatc | 300 | |
| gagaagaagt cgtacccgtt ggaaatccac ttcgttcaca aaaccgagga tggtaaaatc | 360 | |
| ttggtcgtgg gtgtgatggc caaactgggt aagacgaata aagagctgga caagattctg | 420 | |
| aacgtggctc cggcggaaga aggtgaaaag atcctggaca aaaacctgaa cctgaacaac | 480 | |
| ctgattccga agataaacg ttatatgacg tacagcggca gcctgaccac cccaccgtgt | 540 | |
| acggaaggcg ttcgttggat cgttctgaag aagccgatca gcattagcaa acagcagttg | 600 | |
| gagaaactga aagcgtcat ggtcaacccg aataatcgcc cggttcaaga aatcaattcc | 660 | |
| cgttggatta ttgagggctt ctaa | 684 | |

<210> SEQ ID NO 200
<211> LENGTH: 227
<212> TYPE: PRT
<213> ORGANISM: Artificial sequence
<220> FEATURE:
<223> OTHER INFORMATION: Variant: Q18T

<400> SEQUENCE: 200

```
Met Glu His Glu Trp Ser Tyr Glu Gly Glu Lys Gly Pro Glu His Trp
1               5                   10                  15
Ala Thr Leu Lys Pro Glu Phe Phe Trp Cys Lys Leu Lys Asn Gln Ser
            20                  25                  30
Pro Ile Asn Ile Asp Lys Lys Tyr Lys Val Lys Ala Asn Leu Pro Lys
        35                  40                  45
Leu Asn Leu Tyr Tyr Lys Thr Ala Lys Glu Ser Glu Val Val Asn Asn
    50                  55                  60
Gly His Thr Ile Gln Ile Asn Ile Lys Glu Asp Asn Thr Leu Asn Tyr
65                  70                  75                  80
Leu Gly Glu Lys Tyr Gln Leu Lys Gln Phe His Phe His Thr Pro Ser
                85                  90                  95
Glu His Thr Ile Glu Lys Lys Ser Tyr Pro Leu Glu Ile His Phe Val
            100                 105                 110
His Lys Thr Glu Asp Gly Lys Ile Leu Val Val Gly Val Met Ala Lys
        115                 120                 125
Leu Gly Lys Thr Asn Lys Glu Leu Asp Lys Ile Leu Asn Val Ala Pro
    130                 135                 140
Ala Glu Glu Gly Glu Lys Ile Leu Asp Lys Asn Leu Asn Leu Asn Asn
145                 150                 155                 160
Leu Ile Pro Lys Asp Lys Arg Tyr Met Thr Tyr Ser Gly Ser Leu Thr
                165                 170                 175
Thr Pro Pro Cys Thr Glu Gly Val Arg Trp Ile Val Leu Lys Lys Pro
            180                 185                 190
Ile Ser Ile Ser Lys Gln Gln Leu Glu Lys Leu Lys Ser Val Met Val
        195                 200                 205
Asn Pro Asn Asn Arg Pro Val Gln Glu Ile Asn Ser Arg Trp Ile Ile
    210                 215                 220
Glu Gly Phe
225
```

<210> SEQ ID NO 201
<211> LENGTH: 684
<212> TYPE: DNA

<213> ORGANISM: Artificial sequence
<220> FEATURE:
<223> OTHER INFORMATION: Variant: K20W

<400> SEQUENCE: 201

```
atggaacacg aatggagcta cgaaggtgag aagggtcctg agcattgggc gcagttgtgg      60
ccggagttct tttggtgcaa gctgaagaat caatctccga tcaacattga caagaagtac     120
aaagtcaaag cgaatctgcc gaagctgaat ctgtattaca aaccgcaaa agagagcgag      180
gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaaccgagga tggtaaaatc     360
ttggtcgtgg gtgtgatggc caaactgggt aagacgaata aagagctgga caagattctg     420
aacgtggctc cggcggaaga aggtgaaaag atcctggaca aaacctgaa cctgaacaac      480
ctgattccga agataaacg ttatatgacg tacagcggca gcctgaccac cccaccgtgt     540
acggaaggcg ttcgttggat cgttctgaag aagccgatca gcattagcaa acagcagttg    600
gagaaactga aagcgtcat ggtcaacccg aataatcgcc cggttcaaga aatcaattcc     660
cgttggatta ttgagggctt ctaa                                            684
```

<210> SEQ ID NO 202
<211> LENGTH: 227
<212> TYPE: PRT
<213> ORGANISM: Artificial sequence
<220> FEATURE:
<223> OTHER INFORMATION: Variant: K20W

<400> SEQUENCE: 202

```
Met Glu His Glu Trp Ser Tyr Glu Gly Glu Lys Gly Pro Glu His Trp
  1               5                  10                  15

Ala Gln Leu Trp Pro Glu Phe Phe Trp Cys Lys Leu Lys Asn Gln Ser
             20                  25                  30

Pro Ile Asn Ile Asp Lys Lys Tyr Lys Val Lys Ala Asn Leu Pro Lys
         35                  40                  45

Leu Asn Leu Tyr Tyr Lys Thr Ala Lys Glu Ser Glu Val Val Asn Asn
     50                  55                  60

Gly His Thr Ile Gln Ile Asn Ile Lys Glu Asp Asn Thr Leu Asn Tyr
 65                  70                  75                  80

Leu Gly Glu Lys Tyr Gln Leu Lys Gln Phe His Phe His Thr Pro Ser
                 85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205
```

Asn Pro Asn Asn Arg Pro Val Gln Glu Ile Asn Ser Arg Trp Ile Ile
    210                 215                 220

Glu Gly Phe
225

<210> SEQ ID NO 203
<211> LENGTH: 684
<212> TYPE: DNA
<213> ORGANISM: Artificial sequence
<220> FEATURE:
<223> OTHER INFORMATION: Variant: K150I

<400> SEQUENCE: 203
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaccgcaaa agagagcgag     180 gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaaccgagga tggtaaaatc     360
ttggtcgtgg gtgtgatggc caaactgggt aagacgaata aagagctgga caagattctg     420
aacgtggctc cggcggaaga aggtgaaatc atcctggaca aaaacctgaa cctgaacaac     480
ctgattccga agataaaacg ttatatgacg tacagcggca gcctgaccac cccaccgtgt     540
acggaaggcg ttcgttggat cgttctgaag aagccgatca gcattagcaa acagcagttg     600
gagaaactga aaagcgtcat ggtcaacccg aataatcgcc cggttcaaga aatcaattcc     660
cgttggatta ttgagggctt ctaa                                           684

<210> SEQ ID NO 204
<211> LENGTH: 227
<212> TYPE: PRT
<213> ORGANISM: Artificial sequence
<220> FEATURE:
<223> OTHER INFORMATION: VARIANT: K150I

<400> SEQUENCE: 204

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45

Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Ile Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
            165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
            195                 200                 205

Asn Pro Asn Asn Arg Pro Val Gln Glu Ile Asn Ser Arg Trp Ile Ile
            210                 215                 220

Glu Gly Phe
225

<210> SEQ ID NO 205
<211> LENGTH: 684
<212> TYPE: DNA
<213> ORGANISM: Artificial sequence
<220> FEATURE:
<223> OTHER INFORMATION: Variant: K150N

<400> SEQUENCE: 205

```
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaccgcaaa agagagcgag      180
gttgtgaaca atggccacac tattcaaatc aacattaaag aggataacac cctgaattat     240
ctgggtgaaa agtatcaact gaagcagttt cattttcaca cgccgagcga gcataccatc    300
gagaagaagt cgtacccgtt ggaaatccac ttcgttcaca aaaccgagga tggtaaaatc     360
ttggtcgtgg gtgtgatggc caaactgggt aagacgaata agagctgga caagattctg      420
aacgtggctc cggcggaaga aggtgaaaat atcctggaca aaaacctgaa cctgaacaac     480
ctgattccga agataaaacg ttatatgacg tacagcggca gcctgaccac cccaccgtgt     540
acggaaggcg ttcgttggat cgttctgaag aagccgatca gcattagcaa acagcagttg    600
gagaaactga aaagcgtcat ggtcaacccg aataatcgcc cggttcaaga aatcaattcc     660
cgttggatta ttgagggctt ctaa                                            684
```

<210> SEQ ID NO 206
<211> LENGTH: 227
<212> TYPE: PRT
<213> ORGANISM: Artificial sequence
<220> FEATURE:
<223> OTHER INFORMATION: Variant: K150N

<400> SEQUENCE: 206

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
            35                  40                  45

Leu Asn Leu Tyr Tyr Lys Thr Ala Lys Glu Ser Glu Val Val Asn Asn
        50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
            85                  90                  95

Glu His Thr Ile Glu Lys Lys Ser Tyr Pro Leu Glu Ile His Phe Val

```
              100                 105                 110
His Lys Thr Glu Asp Gly Lys Ile Leu Val Val Gly Val Met Ala Lys
            115                 120                 125

Leu Gly Lys Thr Asn Lys Glu Leu Asp Lys Ile Leu Asn Val Ala Pro
130                 135                 140

Ala Glu Glu Gly Glu Asn Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225

<210> SEQ ID NO 207
<211> LENGTH: 684
<212> TYPE: DNA
<213> ORGANISM: Artificial sequence
<220> FEATURE:
<223> OTHER INFORMATION: Variant: T181M

<400> SEQUENCE: 207
atggaacacg aatggagcta cgaaggtgag aagggtcctg agcattgggc gcagttgaaa      60
ccggagttct tttggtgcaa gctgaagaat caatctccga tcaacattga caagaagtac     120
aaagtcaaag cgaatctgcc gaagctgaat ctgtattaca aaccgcaaa agagagcgag      180 gttgtgaaca atggccacac tattcaaatc aacattaaag aggataacac cctgaattat     240
ctgggtgaaa agtatcaact gaagcagttt cattttcaca cgccgagcga gcataccatc     300
gagaagaagt cgtacccgtt ggaaatccac ttcgttcaca aaaccgagga tggtaaaatc     360
ttggtcgtgg gtgtgatggc caaactgggt aagacgaata agagctgga caagattctg      420 aacgtggctc cggcggaaga aggtgaaaag atcctggaca aaaacctgaa cctgaacaac     480
ctgattccga agataaaacg ttatatgacg tacagcggca gcctgaccac cccaccgtgt     540
atggaaggcg ttcgttggat cgttctgaag aagccgatca gcattagcaa acagcagttg     600
gagaaactga aaagcgtcat ggtcaacccg aataatcgcc cggttcaaga aatcaattcc     660
cgttggatta ttgagggctt ctaa                                            684

<210> SEQ ID NO 208
<211> LENGTH: 227
<212> TYPE: PRT
<213> ORGANISM: Artificial sequence
<220> FEATURE:
<223> OTHER INFORMATION: Variant: T181M

<400> SEQUENCE: 208

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
            20                  25                  30

Pro Ile Asn Ile Asp Lys Lys Tyr Lys Val Lys Ala Asn Leu Pro Lys
        35                  40                  45
```

-continued

```
Leu Asn Leu Tyr Tyr Lys Thr Ala Lys Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
                100                 105                 110

His Lys Thr Glu Asp Gly Lys Ile Leu Val Val Gly Val Met Ala Lys
            115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Met Glu Gly Val Arg Trp Ile Val Leu Lys Lys Pro
            180                 185                 190

Ile Ser Ile Ser Lys Gln Gln Leu Glu Lys Leu Lys Ser Val Met Val
            195                 200                 205

Asn Pro Asn Asn Arg Pro Val Gln Glu Ile Asn Ser Arg Trp Ile Ile
    210                 215                 220

Glu Gly Phe
225
```

What is claimed is:

1. A recombinant carbonic anhydrase polypeptide having carbonic anhydrase activity comprising an amino acid sequence having at least 85% identity to SEQ ID NO: 8 and one or more differences as compared to SEQ ID NO: 8 at residue positions selected from 18, 20, 38, 52, 57, 82, 100, 130, 150, and 181.

2. The recombinant carbonic anhydrase polypeptide of claim 1, comprising one or more amino acid differences as compared to SEQ ID NO: 8 selected from:
   (a) 18A, 18C, 18F, 18L, 18R, 18S, 18T, or 18W;
   (b) 20A, 20G, 20L, 20N, 20R, 20S, 20T, or 20W;
   (c) 38A, 38D, 38G, 38L, 38N, 38P, 38R, 38S, or 38W;
   (d) 52C, 52E, 52G, 52P, or 52T;
   (e) 57A, 57G, 57L, 57N, 57P, 57R, 57S, or 57V;
   (f) 82C or 82E;
   (g) 100A, 100E, 100N, 100S, 100V, or 100Y;
   (h) 130A, 130C, or 130L;
   (i) 150A, 150I, 150N, or 150S; and
   (j) 181Q, 181L, 181M, or 181R.

3. The recombinant carbonic anhydrase polypeptide of claim 2, further comprising an amino acid difference as compared to SEQ ID NO: 8 selected from 14D, 65S, 88E, 114I, 116D, 122I, 126L, 148A, 155I, and 205C.

4. The recombinant carbonic anhydrase polypeptide of claim 1, having at least 90% identity to SEQ ID NO: 8.

5. The recombinant carbonic anhydrase polypeptide of claim 1, having at least 95% identity to SEQ ID NO: 8.

6. The recombinant carbonic anhydrase polypeptide of claim 1 comprising two or more amino acid differences as compared to SEQ ID NO: 8 which are: 18T and 20A; 18R and 20A; 2K, 181M, and 197I; 14D and 18R; 52C, 122I, 150N, and 226S; 65S and 150I; 57R and 130C; 82C and 88E; 82C and 148A; 126L and 130L; 82C and 100V; 38C, 82C, and 100V; 38G, 82C, and 100V; 38R, 82C, and 100V; 38S, 82C, and 100V; 38W, 82C, and 100V; 38S, 57A, 82C, and 100V; 38S, 57G, 82C, and 100V; 38S, 57L, 82C, and 100V; 38S, 57S, 82C, and 100V; 38S, 57V, 82C, and 100V; 18F, 20G, 38S, 57L, 82C, and 100V; 18R, 20G, 38S, 57L, 82C, and 100V; 18W, 20G, 38S, 57L, 82C, and 100V; 18R, 20W, 38S, 57L, 82C, and 100V; 18R, 20A, 38S, 57L, 82C, and 100V; 18R, 20R, 38S, 57L, 82C, and 100V; 18C, 20S, 38S, 57L, 82C, and 100V; 18C, 20V, 38S, 57L, 82C, and 100V; 18A, 20T, 38S, 57L, 82C, and 100V; or 18F, 20R, 38S, 57L, 82C, and 100V.

7. A recombinant carbonic anhydrase polypeptide having carbonic anhydrase activity comprising:
   (a) an amino acid sequence having at least 80% identity to SEQ ID NO: 8; and
   (b) one or more differences as compared to SEQ ID NO: 8 at residue positions selected from 18, 20, 38, 52, 57, 82, 100, 130, 150, and 181, wherein said recombinant carbonic anhydrase polypeptide has improved stability relative to the carbonic anhydrase of SEQ ID NO: 8, following 15 minutes of exposure at 92° C. in 0.3M $Na_2CO_3/NaHCO_3$ pH 10.

8. The recombinant carbonic anhydrase polypeptide claim 7, comprising one or more amino acid differences as compared to SEQ ID NO: 8 selected from:
   (a) 18A, 18C, 18F, 18L, 18R, 18S, 18T, or 18W;
   (b) 20A, 20G, 20L, 20N, 20R, 20S, 20T, or 20W;
   (c) 38A, 38D, 38G, 38L, 38N, 38P, 38R, 38S, or 38W;
   (d) 52C, 52E, 52G, 52P, or 52T;
   (e) 57A, 57G, 57L, 57N, 57P, 57R, 57S, or 57V;
   (f) 82C or 82E;
   (g) 100A, 100E, 100N, 100S, 100V, or 100Y;

(h) 130A, 130C, or 130L;
(i) 150A, 150I, 150N, or 150S; and
(j) 181Q, 181L, 181M, or 181R.

9. The recombinant carbonic anhydrase polypeptide claim 8, further comprising an amino acid difference as compared to SEQ ID NO: 8 selected from 14D, 65S, 88E, 114I, 116D, 122I, 126L, 148A, 155I, and 205C.

10. The recombinant carbonic anhydrase polypeptide claim 7, having at least 85% identity to SEQ ID NO: 8.

11. The recombinant carbonic anhydrase polypeptide claim 7, having at least 90% identity to SEQ ID NO: 8.

12. The recombinant carbonic anhydrase polypeptide claim 7, having at least 95% identity to SEQ ID NO: 8.

13. A recombinant carbonic anhydrase polypeptide having carbonic anhydrase activity comprising
  (1) an amino acid sequence having at least 75% identity to SEQ ID NO: 8;
  (2) an amino acid difference as compared to SEQ ID NO: 8 which is 82C; and
  (3) one or more further amino acid differences as compared to SEQ ID NO: 8 selected from:
    (a) 18A, 18C, 18F, 18L, 18R, 18S, 18T, or 18W;
    (b) 20A, 20G, 20L, 20N, 20R, 20S, 20T, or 20W;
    (c) 38A, 38D, 38G, 38L, 38N, 38P, 38R, 38S, or 38W;
    (d) 52C, 52E, 52G, 52P, or 52T;
    (e) 57A, 57G, 57L, 57N, 57P, 57R, 57S, or 57V;
    (f) 100A, 100E, 100N, 100S, 100V, or 100Y;
    (g) 130A, 130C, or 130L;
    (h) 150A, 150I, 150N, or 150S; and
    (i) 181Q, 181L, 181M, or 181R,
  wherein said recombinant carbonic anhydrase polypeptide has improved stability relative to the carbonic anhydrase of SEQ ID NO: 8, following 15 minutes of exposure at 92° C. in 0.3M $Na_2CO_3$/$NaHCO_3$ pH 10.

14. The recombinant carbonic anhydrase polypeptide of claim 2, having at least 90% identity to SEQ ID NO: 8.

15. The recombinant carbonic anhydrase polypeptide of claim 2, having at least 95% identity to SEQ ID NO: 8.

16. The recombinant carbonic anhydrase polypeptide of claim 7 comprising two or more amino acid differences as compared to SEQ ID NO: 8 which are: 18T and 20A; 18R and 20A; 2K, 181M, and 197I; 14D and 18R; 52C, 122I, 150N, and 226S; 65S and 150I; 57R and 130C; 82C and 88E; 82C and 148A; 126L and 130L; 82C and 100V; 38C, 82C, and 100V; 38G, 82C, and 100V; 38R, 82C, and 100V; 38S, 82C, and 100V; 38W, 82C, and 100V; 38S, 57A, 82C, and 100V; 38S, 57G, 82C, and 100V; 38S, 57L, 82C, and 100V; 38S, 57S, 82C, and 100V; 38S, 57V, 82C, and 100V; 18F, 20G, 38S, 57L, 82C, and 100V; 18R, 20G, 38S, 57L, 82C, and 100V; 18W, 20G, 38S, 57L, 82C, and 100V; 18R, 20W, 38S, 57L, 82C, and 100V; 18R, 20A, 38S, 57L, 82C, and 100V; 18R, 20R, 38S, 57L, 82C, and 100V; 18C, 20S, 38S, 57L, 82C, and 100V; 18C, 20V, 38S, 57L, 82C, and 100V; 18A, 20T, 38S, 57L, 82C, and 100V; or 18F, 20R, 38S, 57L, 82C, and 100V.

17. The recombinant carbonic anhydrase polypeptide of claim 8, having at least 85% identity to SEQ ID NO: 8.

18. The recombinant carbonic anhydrase polypeptide of claim 8, having at least 90% identity to SEQ ID NO: 8.

19. The recombinant carbonic anhydrase polypeptide of claim 13, further comprising an amino acid difference as compared to SEQ ID NO: 8 selected from 14D, 65S, 88E, 114I, 116D, 122I, 126L, 148A, 155I, and 205C.

20. The recombinant carbonic anhydrase polypeptide of claim 13 comprising two or more amino acid differences as compared to SEQ ID NO: 8 which are: 18T and 20A; 18R and 20A; 2K, 181M, and 197I; 14D and 18R; 52C, 122I, 150N, and 226S; 65S and 150I; 57R and 130C; 82C and 88E; 82C and 148A; 126L and 130L; 82C and 100V; 38C, 82C, and 100V; 38G, 82C, and 100V; 38R, 82C, and 100V; 38S, 82C, and 100V; 38W, 82C, and 100V; 38S, 57A, 82C, and 100V; 38S, 57G, 82C, and 100V; 38S, 57L, 82C, and 100V; 38S, 57S, 82C, and 100V; 38S, 57V, 82C, and 100V; 18F, 20G, 38S, 57L, 82C, and 100V; 18R, 20G, 38S, 57L, 82C, and 100V; 18W, 20G, 38S, 57L, 82C, and 100V; 18R, 20W, 38S, 57L, 82C, and 100V; 18R, 20A, 38S, 57L, 82C, and 100V; 18R, 20R, 38S, 57L, 82C, and 100V; 18C, 20S, 38S, 57L, 82C, and 100V; 18C, 20V, 38S, 57L, 82C, and 100V; 18A, 20T, 38S, 57L, 82C, and 100V; or 18F, 20R, 38S, 57L, 82C, and 100V.

* * * * *

UNITED STATES PATENT AND TRADEMARK OFFICE
CERTIFICATE OF CORRECTION

PATENT NO. : 9,968,885 B2  
APPLICATION NO. : 14/439218  
DATED : May 15, 2018  
INVENTOR(S) : Richard Daigle Page 1 of 3

It is certified that error appears in the above-identified patent and that said Letters Patent is hereby corrected as shown below:

In the Specification

Column 2, Line 4-5: Change "methydiethanolamine" to --methyldiethanolamine--.

Column 3, Line 61: Change "X1300;" to --X130C;--.

Column 4, Line 8: Change "1100E, 1100N;" to --I100E, I100N;--.

Column 4, Line 9: Change "1100Y;" to --I100Y;--.

Column 6, Line 8: Change "and or activity and or" to --and/or activity and/or--.

Column 6, Line 10: Change "and or activity and or" to --and/or activity and/or--.

Column 6, Line 11: After "ion" insert --;--.

Column 6, Line 12: Change "and or activity and or" to --and/or activity and/or--.

Column 6, Line 14: Change "and or activity and or" to --and/or activity and/or--.

Column 6, Line 16: Change "and or activity and or" to --and/or activity and/or--.

Column 8, Line 38: Change "N,cyclohexyl" to --N-cyclohexyl--.

Column 9, Line 62-63: Change "N,cyclohexyl" to --N-cyclohexyl--.

Column 13, Line 9: Change "Sulfurihydrogenobium" to --Sulfurihydrogenibium--.

Column 15, Line 64: Change "N,cyclohexyl" to --N-cyclohexyl--.

Signed and Sealed this  
Second Day of October, 2018

Andrei Iancu  
*Director of the United States Patent and Trademark Office*

CERTIFICATE OF CORRECTION (continued)
U.S. Pat. No. 9,968,885 B2

Column 16, Line 52: Change "polymethylmetacrylate," to --polymethylmethacrylate,--

Column 16, Line 58: Change "g/m L." to --g/mL.--.

Column 21, Line 45: After "V)" insert --.--.

Column 21, Line 45: Replace "(vat or V)" with "(val or V)".

Column 22, Line 11: Change "cystein" to --cysteine--.

Column 24, Line 5: After "1×108" insert --M-1s-1;--.

Column 24, Line 11: Change ""CAB"" to --"CA_B"--.

Column 25, Line 42: Change "CA_a," to --CA_A,--.

Column 26, Line 13: Change "Az-Ful" to --Az-Fu1--.

Column 26, Line 17: Change "SspSCA" to --SspCA--.

Column 26, Line 27: Change "CAB" to --CA_B--.

Column 31, Line 6: Change "929° C." to --92° C.--.

Column 31, Line 66: Change "I100V;" to --I100V--.

Column 32, Line 58: Change "I100V;" to --I100V--.

Column 32, Line 59: Change "1100V" to --I100V--.

Column 32, Line 62: Change "I100V;" to --I100V--.

Column 32, Line 66: Change "I100V;" to --I100V--.

Column 35, Line 6: Change "Y520-" to --Y52C- --.

Column 35, Line 13: Change "G820-" to --G82C- --.

In the Claims

Column 265, Line 65: Claim 6, change "1971;" to --197I;--.

Column 266, Line 56: Claim 8, after "polypeptide" insert --of--.

Column 267, Line 4: Claim 9, after "polypeptide" insert --of--.

CERTIFICATE OF CORRECTION (continued)
U.S. Pat. No. 9,968,885 B2

Column 267, Line 8: Claim 10, after "polypeptide" insert --of--.

Column 267, Line 10: Claim 11, after "polypeptide" insert --of--.

Column 267, Line 12: Claim 12, after "polypeptide" insert --of--.

Column 267, Line 23: Claim 13, change "20W," to --20W;--.

Column 267, Line 24: Claim 13, change "38W," to --38W;--.

Column 267, Line 25: Claim 13, change "52T," to --52T;--.

Column 267, Line 26: Claim 13, change "57V," to --57V;--.

Column 267, Line 27: Claim 13, change "100Y," to --100Y;--.

Column 267, Line 28: Claim 13, change "130L," to --130L;--.

Column 268, Line 1: Claim 16, change "1971;" to --197I;--.

Column 268, Line 27: Claim 20, change "1971;" to --197I;--.